United States Patent
Deo et al.

(10) Patent No.: US 6,270,765 B1
(45) Date of Patent: *Aug. 7, 2001

(54) THERAPEUTIC COMPOUNDS COMPRISED OF ANTI-FC RECEPTOR ANTIBODIES

(75) Inventors: Yashwant M. Deo, Audubon, PA (US); Joel Goldstein, Edison; Robert Graziano, Frenchtown, both of NJ (US); Chezian Somasundaram, Allentown, PA (US)

(73) Assignee: Medarex, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/188,082

(22) Filed: Nov. 6, 1998

Related U.S. Application Data

(63) Continuation of application No. 08/661,052, filed on Jun. 7, 1996, now Pat. No. 5,837,243, which is a continuation-in-part of application No. 08/484,172, filed on Jun. 7, 1995.

(51) Int. Cl.[7] .................. A61K 39/395; A61K 38/00; A61K 39/00; C12P 21/08
(52) U.S. Cl. ...................... 424/136.1; 424/134.1; 424/135.1; 424/178.1; 424/192.1; 424/193.1; 424/277.1; 435/69.1; 514/12; 530/387.3
(58) Field of Search ............ 424/136.1, 277.1, 424/184.1, 192.1, 135.1, 134.1, 178.1, 193.1; 530/387.3; 512/12; 435/69.1

(56) References Cited

FOREIGN PATENT DOCUMENTS

| | | | |
|---|---|---|---|
| WO 91 05871 | 5/1991 | (WO) . | |
| WO 91/03493 | 3/1992 | (WO) | ............ C07K/15/28 |
| WO 92 05793 | 4/1992 | (WO) . | |
| WO 94/10332 | 5/1994 | (WO) | ............ C12P/21/08 |
| WO 95/09917 | 4/1995 | (WO) | ............ C12N/15/13 |

OTHER PUBLICATIONS

Jung, Gundram, et al., (1991), "Target Cell–Induced T cell Activation with Bi– and Trispecific Antibody Fragments", *Eur. J. Immunol.*, vol. 21, pp. 2431–2435.

Fanger, M. et al. (1994) "Production and Use Of Anti–FcR Bispecific Antibodies" *Immunomethods* 4(1): 72–81.

Repp, R. et al. (1994) "G–CSF Stimulated Neutrophils As Effector Cells In Immunotherapy With A Bispecific Antibody to FcgammaRI and To HER–2/neu (MDX210): Pre-clinical Studies", *Immunobiology*, 191 (2–3): 250–251.

Mabondzo, A. et al. (1994) "Antibody–Dependent Cellular Cytotoxicity and Neutralization of Human Immunodeficiency Virus Type 1 By High Affinity Cross–Linking of gp41 to Human Macrophage Fc IgG Receptor Using Bispecific Antibody" *Journal of General Virology*, 75 (6): 1451–1456.

Chen, J. et al. (1995) "An Immunoconjugate of Lys3–Bombesin and Monoclonal Antibody 22 Can Specifically INduce FcgammaRI (CD64)–Dependent Monocyte– and Neutrophil–Mediated Lysis of Small Cell Carcinoma of the Lung Cells" *Clinical Cancer Research*, 1 (4): 425–434.

Graziano, R. et al. (1995) "Construction and Characterization of a Humanized Anti–Gamma–Ig Receptor Type I (Fcgamma RI) Monoclonal Antibody" *The Journal of Immunology*, 155 (10): 4996–5002.

*Primary Examiner*—Geetha P. Bansal
(74) *Attorney, Agent, or Firm*—Lahive & Cockfield, LLP; Jane E. Remillard; Peter W. Dini

(57) ABSTRACT

Multispecific multivalent molecules which are specific to an Fc receptor (FcR), and therapeutic uses and therapeutic uses and methods for making the molecules are described.

9 Claims, 29 Drawing Sheets h22 HINGE REGION:
[A]
-ACT CAC ACA TGC CCA CCG TGC CCA——CH2——CH3  SEQ ID NO:1
 T   H   T   C   P   P   C   P
[B]
                                    —BamHI—
-ACT CAC ACA TGC CCA CCG TGA GGA TCC-    SEQ ID NO:2
 T   H   T   C   P   P   *
[C]
                                                                            SEQ ID NO:3
               —XhoI—             —NotI—     —BamHI—
-ACT CAC ACA TGC TCG AGC CTT CAC GGC GGC CGC TGA GGA TCC
 T   H   T   C   S   S   L   H   G   G   R   *
FIG. 1

```
          10          20          30          40          50
           *           *           *           *           *
   .EVQLVESGGG  VVQPGRSLRL  SCSSSGFIFS  DNYMYWVRQA  PGKGLEWVAT
          60          70          80          90         100
           *           *           *           *           *
    ISDGGSYTYY  PDSVKGRFTI  SRDNSKNTLF  LQMDSLRPED  TGVYFCARGY
         110         120         130         140         150
           *           *           *           *           *
    YRYEGAMDYW  GQGTPVTVSS  ASTKGPSVFP  LAPSSKSTSG  GTAALGCLVK
         160         170         180         190         200
           *           *           *           *           *
    DYFPERVTVS  WNSGALTSGV  HTFPAVLQSS  GLYSLSSVVT  VPSSSLGTQT
         210         220         230         240         250
           *           *           *  ⇐|⇒       *           *
    YICNVNHKPS  NTKVDKKVEP  KSCDKTHTCS  TTSTTGTSHL  VKCAEKEKTF
                                     H22Fd | HEREGULIN β2 EGF DOMAIN
         260         270         280         290         300
           *           *           *           *           *
    CVNGGECFMV  KDLSNPSRYL  CKCPNEFTGD  RCQNYVMASF  YKAEELYQKR
   SEQ ID NO: 4
```

FIG. 10

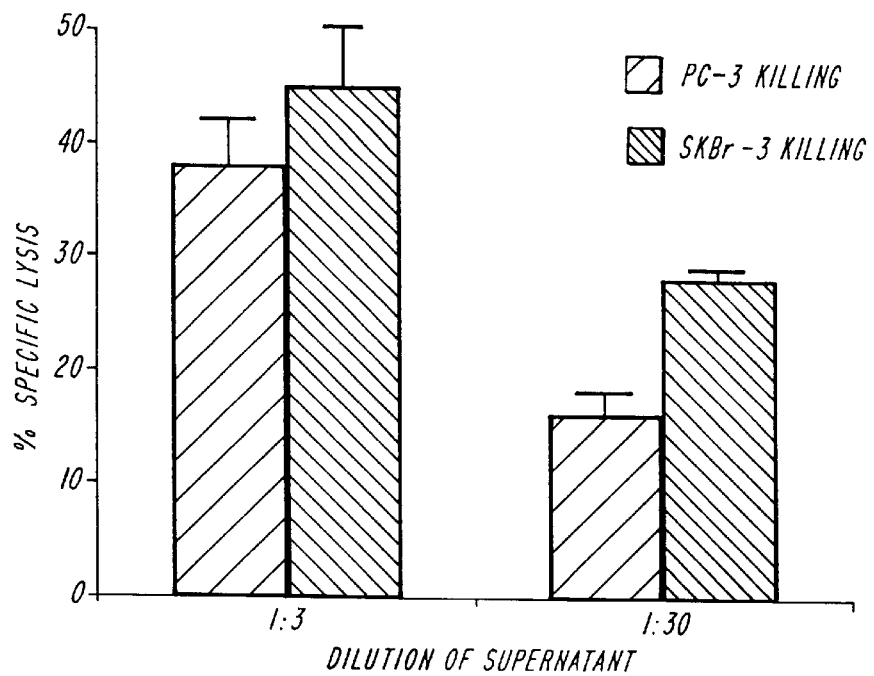

FIG. 11

A. Synthetic Oligonucleotides coding wildtype (TT830) and mutant (TT833S) TT peptides:

TT830:QYIKANSKFIGITEL *(SEQ. ID. NO: 6)*

5'-TCG AGC CAG TAC ATC AAG GCG AAT TCC AAG TTC ATC GGC ATC ACC GAG CTC TGA-3' *(SEQ. ID. NO: 7)*
3'-CG GTC ATG TAG TTC CGC TTA AGG TTC AAG TAG CCG TAG TGG CTC GAG ACT CCG-5' *(SEQ. ID. NO: 8)*

TT833S:QYISANSKFIGITEL *(SEQ. ID. NO: 9)*

5'-TCG AGC CAG TAC ATC AGC GCG AAT TCC AAG TTC ATC GGC ATC ACC GAG CTC TGA-3' *(SEQ. ID. NO: 10)*
3'-CG GTC ATG TAG TCG CGC TTA AGG TTC AAG TAG CCG TAG TGG CTC GAG ACT CCG-5' *(SEQ. ID. NO: 11)*

B. Final H22 chimeric constructs

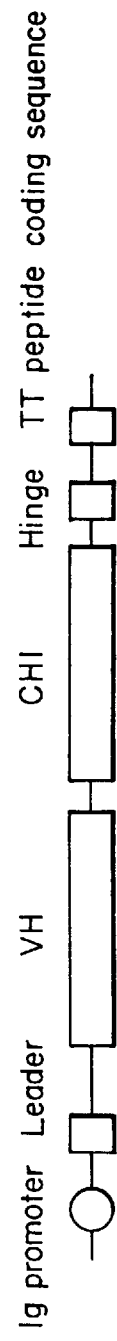

Ig promoter  Leader  VH  CH1  Hinge  TT peptide coding sequence

*FIG. 24*

SEQ ID NO:13

```
AAGCTTCACC ATG GGA TGG AGC TGT ATC ATC CTC TTC TTG GTG GCC ACA      49
           Met Gly Trp Ser Cys Ile Ile Leu Phe Leu Val Ala Thr
           1               5                   10
           SIGNAL SEQUENCE →|→ H22 VH
GCT ACC GGT GTC CAC TCC GAT ATC CAA CTG GTG GAG AGC GGT GGA GGT      97
Ala Thr Gly Val His Ser Asp Ile Gln Leu Val Glu Ser Gly Gly Gly
    15              Gly→ 20    ↖Val         25

GTT GTG CAA CCT GGC CGG TCC CTG CGC CTG TCC TGC TCC TCG TCT GGC     145
Val Val Gln Pro Gly Arg Ser Leu Arg Leu Ser Cys Ser Ser Ser Gly
30                      35                  40                  45

TTC ATT TTC AGT GAC AAT TAC ATG TAT TGG GTG AGA CAG GCA CCT GGA     193
Phe Ile Phe Ser Asp Asn Tyr Met Tyr Trp Val Arg Gln Ala Pro Gly
                    50                  55                  60

AAA GGT CTT GAG TGG GTT GCA ACC ATT AGT GAT GGT GGT AGT TAC ACC     241
Lys Gly Leu Glu Trp Val Ala Thr Ile Ser Asp Gly Gly Ser Tyr Thr
                65                  70                  75

TAC TAT CCA GAC AGT GTG AAG GGA AGA TTT ACA ATA TCG AGA GAC AAC     289
Tyr Tyr Pro Asp Ser Val Lys Gly Arg Phe Thr Ile Ser Arg Asp Asn
            80                  85                  90

AGC AAG AAC ACA TTG TTC CTG CAA ATG GAC AGC CTG AGA CCC GAA GAC     337
Ser Lys Asn Thr Leu Phe Leu Gln Met Asp Ser Leu Arg Pro Glu Asp
        95                  100                 105

ACC GGG GTC TAT TTT TGT GCA AGA GGC TAC TAT AGG TAC GAG GGG GCT     385
Thr Gly Val Tyr Phe Cys Ala Arg Gly Tyr Tyr Arg Tyr Glu Gly Ala
110             115                 120                 125
                                             H22 VH →|→ LINKER
ATG GAC TAC TGG GGC CAA GGG ACC CCG GTC ACC GTG AGC TCA GGA GGT     433
Met Asp Tyr Trp Gly Gln Gly Thr Pro Val Thr Val Ser Ser Gly Gly
                130                 135                 140
                                    LINKER →|→ H22 VL
GGC GGC TCC GGA GGT GGA GGC AGC GGA GGG GGC GGA TCC GAC ATC CAG     481
Gly Gly Ser Gly Gly Gly Gly Ser Gly Gly Gly Gly Ser Asp Ile Gln
            145                 150                 155

CTG ACC CAG AGC CCA AGC AGC CTG AGC GCC AGC GTG GGT GAC AGA GTG     529
Leu Thr Gln Ser Pro Ser Ser Leu Ser Ala Ser Val Gly Asp Arg Val
        160                 165                 170

ACC ATC ACC TGT AAG TCC AGT CAA AGT GTT TTA TAC AGT TCA AAT CAG     577
Thr Ile Thr Cys Lys Ser Ser Gln Ser Val Leu Tyr Ser Ser Asn Gln
    175                 180                 185

AAG AAC TAC TTG GCC TGG TAC CAG CAG AAG CCA GGT AAG GCT CCA AAG     625
Lys Asn Tyr Leu Ala Trp Tyr Gln Gln Lys Pro Gly Lys Ala Pro Lys
190                 195                 200                 205
```

*FIG. 39A*

```
CTG CTG ATC TAC TGG GCA TCC ACT AGG GAA TCT GGT GTG CCA AGC AGA ㉕ 673
Leu Leu Ile Tyr Trp Ala Ser Thr Arg Glu Ser Gly Val Pro Ser Arg
            210                 215                 220

TTC AGC GGT AGC GGT AGC GGT ACC GAC TTC ACC TTC ACC ATC AGC AGC     721
Phe Ser Gly Ser Gly Ser Gly Thr Asp Phe Thr Phe Thr Ile Ser Ser
            225                 230                 235

CTC CAG CCA GAG GAC ATC GCC ACC TAC TAC TGC CAT CAA TAC CTC TCC     769
Leu Gln Pro Glu Asp Ile Ala Thr Tyr Tyr Cys His Gln Tyr Leu Ser
            240                 245                 250
                                        H22 VL→ →Linker tMCS
TCG TGG ACG TTC GGC CAA GGG ACC AAG GTG GAA ATC AAA TCT AGC TGC     817
Ser Trp Thr Phe Gly Gln Gly Thr Lys Val Glu Ile Lys Ser Ser Cys
            255                 260                 265
                        Linker tmcs→  →c-myc tag
TCG AGC GGA GGC GGG GGT AGC GAT ATC GCG GCC GCA GAA CAG AAA CTC     865
Ser Ser Gly Gly Gly Gly Ser Asp Ile Ala Ala Ala Glu Gln Lys Leu
270         275                 280                 285
        c-myc tag→              →Hi5-6 tail
ATC TCA GAA GAG GAT CTG AAT GGC GCC GCA CAT CAC CAT CAT CAC CAT     913
Ile Ser Glu Glu Asp Leu Asn Gly Ala Ala His His His His His His
            290                 295                 300
TGATTCTAGA
                                                                    923
```

*FIG. 39B*

SEQ ID NO:15

```
AAGCTTCACC ATG GGA TGG AGC TGT ATC ATC CTC TTC TTG GTG GCC ACA              49
           Met Gly Trp Ser Cys Ile Ile Leu Phe Leu Val Ala Thr
           1               5                       10
        Signal Sequence →|→ H22 VH
GCT ACC GGT GTC CAC TCC GAT ATC CAA CTG GTG GAG AGC GGT GGA GGT              97
Ala Thr Gly Val His Ser Asp Ile Gln Leu Val Glu Ser Gly Gly Gly
15                       Gly     20      Val              25

GTT GTG CAA CCT GGC CGG TCC CTG CGC CTG TCC TGC TCC TCG TCT GGC              145
Val Val Gln Pro Gly Arg Ser Leu Arg Leu Ser Cys Ser Ser Ser Gly
30                   35                  40                  45

TTC ATT TTC AGT GAC AAT TAC ATG TAT TGG GTG AGA CAG GCA CCT GGA              193
Phe Ile Phe Ser Asp Asn Tyr Met Tyr Trp Val Arg Gln Ala Pro Gly
                 50                  55                  60

AAA GGT CTT GAG TGG GTT GCA ACC ATT AGT GAT GGT GGT AGT TAC ACC              241
Lys Gly Leu Glu Trp Val Ala Thr Ile Ser Asp Gly Gly Ser Tyr Thr
            65                  70                  75

TAC TAT CCA GAC AGT GTG AAG GGA AGA TTT ACA ATA TCG AGA GAC AAC              289
Tyr Tyr Pro Asp Ser Val Lys Gly Arg Phe Thr Ile Ser Arg Asp Asn
        80                  85                  90

AGC AAG AAC ACA TTG TTC CTG CAA ATG GAC AGC CTG AGA CCC GAA GAC              337
Ser Lys Asn Thr Leu Phe Leu Gln Met Asp Ser Leu Arg Pro Glu Asp
    95                  100                 105

ACC GGG GTC TAT TTT TGT GCA AGA GGC TAC TAT AGG TAC GAG GGG GCT              385
Thr Gly Val Tyr Phe Cys Ala Arg Gly Tyr Tyr Arg Tyr Glu Gly Ala
110             115                 120                 125
                                          H22 VH →|→ Linker
ATG GAC TAC TGG GGC CAA GGG ACC CCG GTC ACC GTG AGC TCA GGA GGT              433
Met Asp Tyr Trp Gly Gln Gly Thr Pro Val Thr Val Ser Ser Gly Gly
            130                 135                 140

GGC GGC TCC GGA GGT GGA GGC AGC GGA GGG GGC GGA TCC GAC ATC CAG              481
Gly Gly Ser Gly Gly Gly Gly Ser Gly Gly Gly Gly Ser Asp Ile Gln
            145                 150                 155

CTG ACC CAG AGC CCA AGC AGC CTG AGC GCC AGC GTG GGT GAC AGA GTG              529
Leu Thr Gln Ser Pro Ser Ser Leu Ser Ala Ser Val Gly Asp Arg Val
            160                 165                 170

ACC ATC ACC TGT AAG TCC AGT CAA AGT GTT TTA TAC AGT TCA AAT CAG              577
Thr Ile Thr Cys Lys Ser Ser Gln Ser Val Leu Tyr Ser Ser Asn Gln
175             180                 185

AAG AAC TAC TTG GCC TGG TAC CAG CAG AAG CCA GGT AAG GCT CCA AAG              625
Lys Asn Tyr Leu Ala Trp Tyr Gln Gln Lys Pro Gly Lys Ala Pro Lys
190                 195                 200                 205
```

FIG. 40A

```
CTG CTG ATC TAC TGG GCA TCC ACT AGG GAA TCT GGT GTG CCA AGC AGA   673
Leu Leu Ile Tyr Trp Ala Ser Thr Arg Glu Ser Gly Val Pro Ser Arg
            210                 215                 220

TTC AGC GGT AGC GGT AGC GGT ACC GAC TTC ACC TTC ACC ATC AGC AGC   721
Phe Ser Gly Ser Gly Ser Gly Thr Asp Phe Thr Phe Thr Ile Ser Ser
            225                 230                 235

CTC CAG CCA GAG GAC ATC GCC ACC TAC TAC TGC CAT CAA TAC CTC TCC   769
Leu Gln Pro Glu Asp Ile Ala Thr Tyr Tyr Cys His Gln Tyr Leu Ser
            240                 245                 250
                                          H22 HL→|→Linker
TCG TGG ACG TTC GGC CAA GGG ACC AAG GTG GAA ATC AAA|TCT AGC TGC   817
Ser Trp Thr Phe Gly Gln Gly Thr Lys Val Glu Ile Lys|Ser Ser Cys
            255                 260                 265
           Linker→|→MFE-23 VH
TCG AGC GGA GGC GGG GGT AGC|GAT ATC AAA CTG CAG CAG TCT GGG GCA   865
Ser Ser Gly Gly Gly Gly Ser|Asp Ile Lys Leu Gln Gln Ser Gly Ala
270             275    Gly↗  ↖Val 280                285

GAA CTT GTG AGG TCA GGG ACC TCA GTC AAG TTG TCC TGC ACA GCT TCT   913
Glu Leu Val Arg Ser Gly Thr Ser Val Lys Leu Ser Cys Thr Ala Ser
            290                 295                 300

GGC TTC AAC ATT AAA GAC TCC TAT ATG CAC TGG TTG AGG CAG GGG CCT   961
Gly Phe Asn Ile Lys Asp Ser Tyr Met His Trp Leu Arg Gln Gly Pro
            305                 310                 315

GAA CAG GGC CTG GAG TGG ATT GGA TGG ATT GAT CCT GAG AAT GGT GAT  1009
Glu Gln Gly Leu Glu Trp Ile Gly Trp Ile Asp Pro Glu Asn Gly Asp
            320                 325                 330

ACT GAA TAT GCC CCG AAG TTC CAG GGC AAG GCC ACT TTT ACT ACA GAC  1057
Thr Glu Tyr Ala Pro Lys Phe Gln Gly Lys Ala Thr Phe Thr Thr Asp
            335                 340                 345

ACA TCC TCC AAC ACA GCC TAC CTG CAG CTG AGC AGC CTG ACA TCT GAG  1105
Thr Ser Ser Asn Thr Ala Tyr Leu Gln Leu Ser Ser Leu Thr Ser Glu
350             355                 360                 365

GAC ACT GCC GTC TAT TAT TGT AAT GAG GGG ACT CCG ACT GGG CCG TAC  1153
Asp Thr Ala Val Tyr Tyr Cys Asn Glu Gly Thr Pro Thr Gly Pro Tyr
            370                 375                 380
                                              MFE-23 VH→|→Linker
TAC TTT GAC TAC TGG GGC CAA GGG ACC ACG GTC ACC GTC TCC TCA|GGT  1201
Tyr Phe Asp Tyr Trp Gly Gln Gly Thr Thr Val Thr Val Ser Ser|Gly
            385                 390                 395
                                            Linker→|→MFE-23 VL
GGA GGC GGT TCA GGC GGA GGT GGC TCT GGC GGT GGC GGA TCA|GAA AAT  1249
Gly Gly Gly Ser Gly Gly Gly Gly Ser Gly Gly Gly Gly Ser|Glu Asn
            400                 405                 410
```

*FIG. 40B*

```
GTG CTC ACC CAG TCT CCA GCA ATC ATG TCT GCA TCT CCA GGG GAG AAG      1297
Val Leu Thr Gln Ser Pro Ala Ile Met Ser Ala Ser Pro Gly Glu Lys
    415             420             425

GTC ACC ATA ACC TGC AGT GCC AGC TCA AGT GTA AGT TAC ATG CAC TGG      1345
Val Thr Ile Thr Cys Ser Ala Ser Ser Ser Val Ser Tyr Met His Trp
430             435             440             445

TTC CAG CAG AAG CCA GGC ACT TCT CCC AAA CTC TGG ATT TAT AGC ACA      1393
Phe Gln Gln Lys Pro Gly Thr Ser Pro Lys Leu Trp Ile Tyr Ser Thr
                450             455             460

TCC AAC CTG GCT TCT GGA GTC CCT GCT CGC TTC AGT GGC AGT GGA TCT      1441
Ser Asn Leu Ala Ser Gly Val Pro Ala Arg Phe Ser Gly Ser Gly Ser
            465             470             475

GGG ACC TCT TAC TCT CTC ACA ATC AGC CGA ATG GAG GCT GAA GAT GCT      1489
Gly Thr Ser Tyr Ser Leu Thr Ile Ser Arg Met Glu Ala Glu Asp Ala
        480             485             490

GCC ACT TAT TAC TGC CAG CAA CGG AGT AGT TAC CCA CTC ACG TTC GGT      1537
Ala Thr Tyr Tyr Cys Gln Gln Arg Ser Ser Tyr Pro Leu Thr Phe Gly
    495             500             505
                                    MFE-23 VL→|→Linker
GCT GGC ACC AAG CTG GAG CTG AAA CGG GCG GCA GGC TCG AGC GGA GGC      1585
Ala Gly Thr Lys Leu Glu Leu Lys Arg Ala Ala Gly Ser Ser Gly Gly
510             515             520             525
            Linker→|→c-myc tag
GGG GGT AGC GAT ATC GCG GCC GCA GAA CAG AAA CTC ATC TCA GAA GAG      1633
Gly Gly Ser Asp Ile Ala Ala Ala Glu Gln Lys Leu Ile Ser Glu Glu
            530             535             540
c-myc→|       |→His-6 tail
GAT CTG AAT GGC GCC GCA CAT CAC CAT CAT CAC CAT TGATTCTAGA          1679
Asp Leu Asn Gly Ala Ala His His His His His His
            545             550
```

FIG. 40C

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..24

(xi) SEQUENCE DESCRIPTION: SEQ ID NO: 1:

```
ACT CAC ACA TGC CCA CCG TGC CCA                          24
Thr His Thr Cys Pro Pro Cys Pro
 1               5
```

(2) INFORMATION FOR SEQ ID NO: 2:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..19

(xi) SEQUENCE DESCRIPTION: SEQ ID NO: 2:

```
ACT CAC ACA TGC CCA CCG T GAGGATCC                          27
Thr His Thr Cys Pro Pro
 1               5
```

(2) INFORMATION FOR SEQ ID NO: 3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..34

(xi) SEQUENCE DESCRIPTION: SEQ ID NO: 3:

```
ACT CAC ACA TGC TCG AGC CTT CAC GGC GGC CGC T GAGGATCC      42
Thr His Thr Cys Ser Ser Leu His Gly Gly Arg
 1               5                   10
```

(2) INFORMATION FOR SEQ ID NO: 4:

(i) SEQUENCE CHARACTERISTICS:
        (A) LENGTH: 300 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 4:

```
Glu Val Gln Leu Val Glu Ser Gly Gly Gly Val Val Gln Pro Gly Arg
 1               5                  10                  15

Ser Leu Arg Leu Ser Cys Ser Ser Gly Phe Ile Phe Ser Asp Asn
                20                  25                  30

Tyr Met Tyr Trp Val Arg Gln Ala Pro Gly Lys Gly Leu Glu Trp Val
            35                  40                  45

Ala Thr Ile Ser Asp Gly Gly Ser Tyr Thr Tyr Tyr Pro Asp Ser Val
        50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Gly Tyr Tyr Arg Tyr Glu Gly Ala Met Asp Tyr Trp Gly Gln
            100                 105                 110

Gly Thr Pro Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Arg Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Ser Thr Thr Ser Thr Thr Gly Thr Ser His Leu
225                 230                 235                 240

Val Lys Cys Ala Glu Lys Glu Lys Thr Phe Cys Val Asn Gly Gly Glu
                245                 250                 255

Cys Phe Met Val Lys Asp Leu Ser Asn Pro Ser Arg Tyr Leu Cys Lys
                260                 265                 270

Cys Pro Asn Glu Phe Thr Gly Asp Arg Cys Gln Asn Tyr Val Met Ala
                275                 280                 285

Ser Phe Tyr Lys Ala Glu Glu Leu Tyr Gln Lys Arg
                290                 295                 300

(2) INFORMATION FOR SEQ ID NO: 5:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 5:

Gln Arg Leu Gly Asn Gln Trp Ala Val Gly His Leu Met Gly
1               5                   10

(2) INFORMATION FOR SEQ ID NO: 6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 6:

Gln Tyr Ile Lys Ala Asn Ser Lys Phe Ile Gly Ile Thr Glu Leu
1               5                   10                  15

(2) INFORMATION FOR SEQ ID NO: 7:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

TCGAGCCAGT ACATCAAGGC GAATTCCAAG TTCATCGGCA TCACCGAGCT CTGA        54
```

(2) INFORMATION FOR SEQ ID NO: 8:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CGGTCATGTA GTTCCGCTTA AGGTTCAAGT AGCCGTAGTG GCTCGAGACT CCG      53

(2) INFORMATION FOR SEQ ID NO: 9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 9:

```
Gln Tyr Ile Ser Ala Asn Ser Lys Phe Ile Gly Ile Thr Glu Leu
 1               5                  10                  15
```

(2) INFORMATION FOR SEQ ID NO: 10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

TCGAGCCAGT ACATCAGCGC GAATTCCAAG TTCATCGGCA TCACCGAGCT CTGA      54

(2) INFORMATION FOR SEQ ID NO: 11:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CGGTCATGTA GTCGCGCTTA AGGTTCAAGT AGCCGTAGTG GCTCGAGACT CCG      53

(2) INFORMATION FOR SEQ ID NO: 12:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 12:

```
Phe Asn Asn Phe Thr Val Ser Phe Trp Leu Arg Val Pro Lys Val Ser
 1               5                  10                  15
```

```
Ala Ser His Leu Glu
        20
```

(2) INFORMATION FOR SEQ ID NO: 13:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 11..911

(xi) SEQUENCE DESCRIPTION: SEQ ID NO: 13:

```
AAGCTTCACC ATG GGA TGG AGC TGT ATC ATC CTC TTC TTG GTG GCC ACA        49
           Met Gly Trp Ser Cys Ile Ile Leu Phe Leu Val Ala Thr
            1               5                  10

GCT ACC GGT GTC CAC TCC GAT ATC CAA CTG GTG GAG AGC GGT GGA GGT       97
Ala Thr Gly Val His Ser Asp Ile Gln Leu Val Glu Ser Gly Gly Gly
 15                  20                  25

GTT GTG CAA CCT GGC CGG TCC CTG CGC CTG TCC TGC TCC TCG TCT GGC      145
Val Val Gln Pro Gly Arg Ser Leu Arg Leu Ser Cys Ser Ser Ser Gly
 30                  35                  40                  45

TTC AGT TTC AGT GAC AAT TAC ATG TAT TGG GTG AGA CAG GCA CCT GGA      193
Phe Ile Phe Ser Asp Asn Tyr Met Tyr Trp Val Arg Gln Ala Pro Gly
                 50                  55                  60

AAA GGT CTT GAG TGG GTT GCA ACC ATT AGT GAT GGT GGT AGT TAC ACC      241
Lys Gly Leu Glu Trp Val Ala Thr Ile Ser Asp Gly Gly Ser Tyr Thr
             65                  70                  75

TAC TAT CCA GAC AGT GTG AAG GGA AGA TTT ACA ATA TCG AGA GAC AAC      289
Tyr Tyr Pro Asp Ser Val Lys Gly Arg Phe Thr Ile Ser Arg Asp Asn
         80                  85                  90

AGC AAG AAC ACA TTG TTC CTG CAA ATG GAC AGC CTG AGA CCC GAA GAC      337
Ser Lys Asn Thr Leu Phe Leu Gln Met Asp Ser Leu Arg Pro Glu Asp
 95                 100                 105

ACC GGG GTC TAT TTT TGT GCA AGA GGC TAC TAT AGG TAC GAG GGG GCT      385
Thr Gly Val Tyr Phe Cys Ala Arg Gly Tyr Tyr Arg Tyr Glu Gly Ala
110                 115                 120                 125

ATG GAC TAC TGG GGC CAA GGG ACC CCG GTC ACC GTG AGC TCA GGA GGT      433
Met Asp Tyr Trp Gly Gln Gly Thr Pro Val Thr Val Ser Ser Gly Gly
                130                 135                 140

GGC GGC TCC GGA GGT GGA GGC AGC GGA GGG GGC GGA TCC GAC ATC CAG      481
Gly Gly Ser Gly Gly Gly Gly Ser Gly Gly Gly Gly Ser Asp Ile Gln
            145                 150                 155

CTG ACC CAG AGC CCA AGC AGC CTG AGC GCC AGC GTG GGT GAC AGA GTG      529
Leu Thr Gln Ser Pro Ser Ser Leu Ser Ala Ser Val Gly Asp Arg Val
        160                 165                 170

ACC ATC ACC TGT AAG TCC AGT CAA AGT GTT TTA TAC AGT TCA AAT CAG      577
Thr Ile Thr Cys Lys Ser Ser Gln Ser Val Leu Tyr Ser Ser Asn Gln
175                 180                 185

AAG AAC TAC TTG GCC TGG TAC CAG CAG AAG CCA GGT AAG GCT CCA AAG      625
Lys Asn Tyr Leu Ala Trp Tyr Gln Gln Lys Pro Gly Lys Ala Pro Lys
190                 195                 200                 205

CTG CTG ATC TAC TGG GCA TCC ACT AGG GAA TCT GGT GTG CCA AGC AGA      673
Leu Leu Ile Tyr Trp Ala Ser Thr Arg Glu Ser Gly Val Pro Ser Arg
                210                 215                 220

TTC AGC GGT AGC GGT AGC GGT ACC GAC TTC ACC TTC ACC ATC AGC AGC      721
Phe Ser Gly Ser Gly Ser Gly Thr Asp Phe Thr Phe Thr Ile Ser Ser
            225                 230                 235
```

```
CTC CAG CCA GAG GAC ATC GCC ACC TAC TAC TGC CAT CAA TAC CTC TCC    769
Leu Gln Pro Glu Asp Ile Ala Thr Tyr Tyr Cys His Gln Tyr Leu Ser
            240                 245                 250

TCG TGG ACG TTC GGC CAA GGG ACC AAG GTG GAA ATC AAA TCT AGC TGC    817
Ser Trp Thr Phe Gly Gln Gly Thr Lys Val Glu Ile Lys Ser Ser Cys
        255                 260                 265

TCG AGC GGA GGC GGG GGT AGC GAT ATC GCG GCC GCA GAA CAG AAA CTC    865
Ser Ser Gly Gly Gly Gly Ser Asp Ile Ala Ala Ala Glu Gln Lys Leu
270                 275                 280                 285

ATC TCA GAA GAG GAT CTG AAT GGC GCC GCA CAT CAC CAT CAT CAC CAT    913
Ile Ser Glu Glu Asp Leu Asn Gly Ala Ala His His His His His His
                290                 295                 300
```

(2) INFORMATION FOR SEQ ID NO: 14:

(i) SEQUENCE CHARACTERISTICS:
        (A) LENGTH: 301 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Gly Trp Ser Cys Ile Ile Leu Phe Leu Val Ala Thr Ala Thr Gly
 1               5                  10                  15

Val His Ser Asp Ile Gln Leu Val Glu Ser Gly Gly Gly Val Val Gln
                20                  25                  30

Pro Gly Arg Ser Leu Arg Leu Ser Cys Ser Ser Ser Gly Phe Ile Phe
            35                  40                  45

Ser Asp Asn Tyr Met Tyr Trp Val Arg Gln Ala Pro Gly Lys Gly Leu
         50                  55                  60

Glu Trp Val Ala Thr Ile Ser Asp Gly Gly Ser Tyr Thr Tyr Tyr Pro
 65                  70                  75                  80

Asp Ser Val Lys Gly Arg Phe Thr Ile Ser Arg Asp Asn Ser Lys Asn
                 85                  90                  95

Thr Leu Phe Leu Gln Met Asp Ser Leu Arg Pro Glu Asp Thr Gly Val
                100                 105                 110

Tyr Phe Cys Ala Arg Gly Tyr Tyr Arg Tyr Glu Gly Ala Met Asp Tyr
            115                 120                 125

Trp Gly Gln Gly Thr Pro Val Thr Val Ser Ser Gly Gly Gly Gly Ser
130                 135                 140

Gly Gly Gly Gly Ser Gly Gly Gly Ser Asp Ile Gln Leu Thr Gln
145                 150                 155                 160

Ser Pro Ser Ser Leu Ser Ala Ser Val Gly Asp Arg Val Thr Ile Thr
                165                 170                 175

Cys Lys Ser Ser Gln Ser Val Leu Tyr Ser Ser Asn Gln Lys Asn Tyr
            180                 185                 190

Leu Ala Trp Tyr Gln Gln Lys Pro Gly Lys Ala Pro Lys Leu Leu Ile
        195                 200                 205

Tyr Trp Ala Ser Thr Arg Glu Ser Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys His Gln Tyr Leu Ser Ser Trp Thr
                245                 250                 255

Phe Gly Gln Gly Thr Lys Val Glu Ile Lys Ser Ser Cys Ser Ser Gly
            260                 265                 270
```

```
Gly Gly Gly Ser Asp Ile Ala Ala Ala Glu Gln Lys Leu Ile Ser Glu
            275                 280                 285

Glu Asp Leu Asn Gly Ala Ala His His His His His
    290                 295                 300

(2) INFORMATION FOR SEQ ID NO: 15:

(i) SEQUENCE CHARACTERISTICS:
        (A) LENGTH: 1679 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 11..1667

(xi) SEQUENCE DESCRIPTION: SEQ ID NO: 15:

AAGCTTCACC ATG GGA TGG AGC TGT ATC ATC CTC TTC TTG GTG GCC ACA          49
           Met Gly Trp Ser Cys Ile Ile Leu Phe Leu Val Ala Thr
             1               5                  10

GCT ACC GGT GTC CAC TCC GAT ATC CAA CTG GTG GAG AGC GGT GGA GGT         97
Ala Thr Gly Val His Ser Asp Ile Gln Leu Val Glu Ser Gly Gly Gly
 15                  20                  25

GTT GTG CAA CCT GGC CGG TCC CTG CGC CTG TCC TGC TCC TCG TCT GGC         145
Val Val Gln Pro Gly Arg Ser Leu Arg Leu Ser Cys Ser Ser Ser Gly
 30                  35                  40                  45

TTC ATT TTC AGT GAC AAT TAC ATG TAT TGG GTG AGA CAG GCA CCT GGA         193
Phe Ile Phe Ser Asp Asn Tyr Met Tyr Trp Val Arg Gln Ala Pro Gly
                 50                  55                  60

AAA GGT CTT GAG TGG GTT GCA ACC ATT AGT GAT GGT GGT AGT TAC ACC         241
Lys Gly Leu Glu Trp Val Ala Thr Ile Ser Asp Gly Gly Ser Tyr Thr
         65                  70                  75

TAC TAT CCA GAC AGT GTG AAG GGA AGA TTT ACA ATA TCG AGA GAC AAC         289
Tyr Tyr Pro Asp Ser Val Lys Gly Arg Phe Thr Ile Ser Arg Asp Asn
         80                  85                  90

AGC AAG AAC ACA TTG TTC CTG CAA ATG GAC AGC CTG AGA CCC GAA GAC         337
Ser Lys Asn Thr Leu Phe Leu Gln Met Asp Ser Leu Arg Pro Glu Asp
 95                 100                 105

ACC GGG GTC TAT TTT TGT GCA AGA GGC TAC TAT AGG TAC GAG GGG GCT         385
Thr Gly Val Tyr Phe Cys Ala Arg Gly Tyr Tyr Arg Tyr Glu Gly Ala
110                 115                 120                 125

ATG GAC TAC TGG GGC CAA GGG ACC CCG GTC ACC GTG AGC TCA GGA GGT         433
Met Asp Tyr Trp Gly Gln Gly Thr Pro Val Thr Val Ser Ser Gly Gly
                130                 135                 140

GGC GGC TCC GGA GGT GGA GGC AGC GGA GGG GGC GGA TCC GAC ATC CAG         481
Gly Gly Ser Gly Gly Gly Gly Ser Gly Gly Gly Gly Ser Asp Ile Gln
                145                 150                 155

CTG ACC CAG AGC CCA AGC AGC CTG AGC GCC AGC GTG GGT GAC AGA GTG         529
Leu Thr Gln Ser Pro Ser Ser Leu Ser Ala Ser Val Gly Asp Arg Val
                160                 165                 170

ACC ATC ACC TGT AAG TCC AGT CAA AGT GTT TTA TAC AGT TCA AAT CAG         577
Thr Ile Thr Cys Lys Ser Ser Gln Ser Val Leu Tyr Ser Ser Asn Gln
175                 180                 185

AAG AAC TAC TTG GCC TGG TAC CAG CAG AAG CCA GGT AAG GCT CCA AAG         625
Lys Asn Tyr Leu Ala Trp Tyr Gln Gln Lys Pro Gly Lys Ala Pro Lys
190                 195                 200                 205

CTG CTG ATC TAC TGG GCA TCC ACT AGG GAA TCT GGT GTG CCA AGC AGA         673
Leu Leu Ile Tyr Trp Ala Ser Thr Arg Glu Ser Gly Val Pro Ser Arg
                210                 215                 220
```

```
TTC AGC GGT AGC GGT AGC GGT ACC GAC TTC ACC TTC ACC ATC AGC AGC      721
Phe Ser Gly Ser Gly Ser Gly Thr Asp Phe Thr Phe Thr Ile Ser Ser
            225                 230                 235

CTC CAG CCA GAG GAC ATC GCC ACC TAC TAC TGC CAT CAA TAC CTC TCC      769
Leu Gln Pro Glu Asp Ile Ala Thr Tyr Tyr Cys His Gln Tyr Leu Ser
            240                 245                 250

TCG TGG ACG TTC GGC CAA GGG ACC AAG GTG GAA ATC AAA TCT AGC TGC      817
Ser Trp Thr Phe Gly Gln Gly Thr Lys Val Glu Ile Lys Ser Ser Cys
            255                 260                 265

TCG AGC GGA GGC GGG GGT AGC GAT ATC AAA CTG CAG CAG TCT GGG GCA      865
Ser Ser Gly Gly Gly Gly Ser Asp Ile Lys Leu Gln Gln Ser Gly Ala
270                 275                 280                 285

GAA CTT GTG AGG TCA GGG ACC TCA GTC AAG TTG TCC TGC ACA GCT TCT      913
Glu Leu Val Arg Ser Gly Thr Ser Val Lys Leu Ser Cys Thr Ala Ser
                290                 295                 300

GGC TTC AAC ATT AAA GAC TCC TAT ATG CAC TGG TTG AGG CAG GGG CCT      961
Gly Phe Asn Ile Lys Asp Ser Tyr Met His Trp Leu Arg Gln Gly Pro
            305                 310                 315

GAA CAG GGC CTG GAG TGG ATT GGA TGG ATT GAT CCT GAG AAT GGT GAT     1009
Glu Gln Gly Leu Glu Trp Ile Gly Trp Ile Asp Pro Glu Asn Gly Asp
            320                 325                 330

ACT GAA TAT GCC CCG AAG TTC CAG GGC AAG GCC ACT TTT ACT ACA GAC     1057
Thr Glu Tyr Ala Pro Lys Phe Gln Gly Lys Ala Thr Phe Thr Thr Asp
            335                 340                 345

ACA TCC TCC AAC ACA GCC TAC CTG CAG CTG AGC AGC CTG ACA TCT GAG     1105
Thr Ser Ser Asn Thr Ala Tyr Leu Gln Leu Ser Ser Leu Thr Ser Glu
350                 355                 360                 365

GAC ACT GCC GTC TAT TAT TGT AAT GAG GGG ACT CCG ACT GGG CCG TAC     1153
Asp Thr Ala Val Tyr Tyr Cys Asn Glu Gly Thr Pro Thr Gly Pro Tyr
                370                 375                 380

TAC TTT GAC TAC TGG GGC CAA GGG ACC ACG GTC ACC GTC TCC TCA GGT     1201
Tyr Phe Asp Tyr Trp Gly Gln Gly Thr Thr Val Thr Val Ser Ser Gly
            385                 390                 395

GGA GGC GGT TCA GGC GGA GGT GGC TCT GGC GGT GGC GGA TCA GAA AAT     1249
Gly Gly Gly Ser Gly Gly Gly Gly Ser Gly Gly Gly Gly Ser Glu Asn
            400                 405                 410

GTG CTC ACC CAG TCT CCA GCA ATC ATG TCT GCA TCT CCA GGG GAG AAG     1297
Val Leu Thr Gln Ser Pro Ala Ile Met Ser Ala Ser Pro Gly Glu Lys
            415                 420                 425

GTC ACC ATA ACC TGC AGT GCC AGC TCA AGT GTA AGT TAC ATG CAC TGG     1345
Val Thr Ile Thr Cys Ser Ala Ser Ser Ser Val Ser Tyr Met His Trp
430                 435                 440                 445

TTC CAG CAG AAG CCA GGC ACT TCT CCC AAA CTC TGG ATT TAT AGC ACA     1393
Phe Gln Gln Lys Pro Gly Thr Ser Pro Lys Leu Trp Ile Tyr Ser Thr
            450                 455                 460

TCC AAC CTG GCT TCT GGA GTC CCT GCT CGC TTC AGT GGC AGT GGA TCT     1441
Ser Asn Leu Ala Ser Gly Val Pro Ala Arg Phe Ser Gly Ser Gly Ser
            465                 470                 475

GGG ACC TCT TAC TCT CTC ACA ATC AGC CGA ATG GAG GCT GAA GAT GCT     1489
Gly Thr Ser Tyr Ser Leu Thr Ile Ser Arg Met Glu Ala Glu Asp Ala
            480                 485                 490

GCC ACT TAT TAC TGC CAG CAA CGG AGT AGT TAC CCA CTC ACG TTC GGT     1537
Ala Thr Tyr Tyr Cys Gln Gln Arg Ser Ser Tyr Pro Leu Thr Phe Gly
            495                 500                 505

GCT GGC ACC AAG CTG GAG CTG AAA CGG GCG GCA GGC TCG AGC GGA GGC     1585
Ala Gly Thr Lys Leu Glu Leu Lys Arg Ala Ala Gly Ser Ser Gly Gly
510                 515                 520                 525

GGG GGT AGC GAT ATC GCG GCC GCA GAA CAG AAA CTC ATC TCA GAA GAG     1633
Gly Gly Ser Asp Ile Ala Ala Ala Glu Gln Lys Leu Ile Ser Glu Glu
```

```
                    530             535             540
GAT CTG AAT GGC GCC GCA CAT CAC CAT CAT CAC CAT TGATTCTAGA          1679
Asp Leu Asn Gly Ala Ala His His His His His His
            545             550
```

(2) INFORMATION FOR SEQ ID NO: 16:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Gly Trp Ser Cys Ile Ile Leu Phe Leu Val Ala Thr Ala Thr Gly
 1               5                  10                  15

Val His Ser Asp Ile Gln Leu Val Glu Ser Gly Gly Val Val Gln
            20                  25                  30

Pro Gly Arg Ser Leu Arg Leu Ser Cys Ser Ser Gly Phe Ile Phe
            35                  40                  45

Ser Asp Asn Tyr Met Tyr Trp Val Arg Gln Ala Pro Gly Lys Gly Leu
 50                  55                  60

Glu Trp Val Ala Thr Ile Ser Asp Gly Gly Ser Tyr Thr Tyr Tyr Pro
 65                  70                  75                  80

Asp Ser Val Lys Gly Arg Phe Thr Ile Ser Arg Asp Asn Ser Lys Asn
                85                  90                  95

Thr Leu Phe Leu Gln Met Asp Ser Leu Arg Pro Glu Asp Thr Gly Val
                100                 105                 110

Tyr Phe Cys Ala Arg Gly Tyr Tyr Arg Tyr Glu Gly Ala Met Asp Tyr
            115                 120                 125

Trp Gly Gln Gly Thr Pro Val Thr Val Ser Ser Gly Gly Gly Gly Ser
130                 135                 140

Gly Gly Gly Gly Ser Gly Gly Gly Gly Ser Asp Ile Gln Leu Thr Gln
145                 150                 155                 160

Ser Pro Ser Ser Leu Ser Ala Ser Val Gly Asp Arg Val Thr Ile Thr
                165                 170                 175

Cys Lys Ser Ser Gln Ser Val Leu Tyr Ser Ser Asn Gln Lys Asn Tyr
            180                 185                 190

Leu Ala Trp Tyr Gln Gln Lys Pro Gly Lys Ala Pro Lys Leu Leu Ile
            195                 200                 205

Tyr Trp Ala Ser Thr Arg Glu Ser Gly Val Pro Ser Arg Phe Ser Gly
210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys His Gln Tyr Leu Ser Ser Trp Thr
                245                 250                 255

Phe Gly Gln Gly Thr Lys Val Glu Ile Lys Ser Ser Cys Ser Ser Gly
            260                 265                 270

Gly Gly Gly Ser Asp Ile Lys Leu Gln Gln Ser Gly Ala Glu Leu Val
            275                 280                 285

Arg Ser Gly Thr Ser Val Lys Leu Ser Cys Thr Ala Ser Gly Phe Asn
        290                 295                 300

Ile Lys Asp Ser Tyr Met His Trp Leu Arg Gln Gly Pro Glu Gln Gly
305                 310                 315                 320

Leu Glu Trp Ile Gly Trp Ile Asp Pro Glu Asn Gly Asp Thr Glu Tyr
```

-continued

```
                         325                     330                     335
Ala Pro Lys Phe Gln Gly Lys Ala Thr Phe Thr Thr Asp Thr Ser Ser
                340                     345                     350

Asn Thr Ala Tyr Leu Gln Leu Ser Ser Leu Thr Ser Glu Asp Thr Ala
            355                     360                     365

Val Tyr Tyr Cys Asn Glu Gly Thr Pro Thr Gly Pro Tyr Tyr Phe Asp
        370                     375                     380

Tyr Trp Gly Gln Gly Thr Thr Val Thr Val Ser Ser Gly Gly Gly Gly
385                     390                     395                 400

Ser Gly Gly Gly Gly Ser Gly Gly Gly Gly Ser Glu Asn Val Leu Thr
                405                     410                     415

Gln Ser Pro Ala Ile Met Ser Ala Ser Pro Gly Glu Lys Val Thr Ile
                420                     425                     430

Thr Cys Ser Ala Ser Ser Ser Val Ser Tyr Met His Trp Phe Gln Gln
            435                     440                     445

Lys Pro Gly Thr Ser Pro Lys Leu Trp Ile Tyr Ser Thr Ser Asn Leu
    450                     455                     460

Ala Ser Gly Val Pro Ala Arg Phe Ser Gly Ser Gly Ser Gly Thr Ser
465                     470                     475                 480

Tyr Ser Leu Thr Ile Ser Arg Met Glu Ala Glu Asp Ala Ala Thr Tyr
                485                     490                     495

Tyr Cys Gln Gln Arg Ser Ser Tyr Pro Leu Thr Phe Gly Ala Gly Thr
                500                     505                     510

Lys Leu Glu Leu Lys Arg Ala Ala Gly Ser Ser Gly Gly Gly Gly Ser
            515                     520                     525

Asp Ile Ala Ala Ala Glu Gln Lys Leu Ile Ser Glu Glu Asp Leu Asn
    530                     535                     540

Gly Ala Ala His His His His His His
545                 550
```

THERAPEUTIC COMPOUNDS COMPRISED OF ANTI-FC RECEPTOR ANTIBODIES

This application is a continuation application of Ser. No. 08/661,052 filed on Jun. 7, 1996, U.S. Pat. No. 5,837,243, which in turn is a continuation-in-part application of Ser. No. 08/484,172 filed on Jun. 7, 1995. The contents of all of the aforementioned application(s) are hereby incorporated by reference.

BACKGROUND OF THE INVENTION

Immunoglobulins (Igs) are composed of two heavy and two light chains, each of which contains an $NH_2$-terminal antigen-binding variable domain and a COOH-terminal constant domain responsible for the effector functions of antibodies. The COOH-terminal domains of Ig heavy chains form the Fc region and are involved in triggering cellular activities through interaction with specific receptors known as Fc receptors (FcRs). Fc receptors for all Ig classes, or isotypes, (e.g., IgG (FcγR), IgE (FcεR), IgA (FcαR), IgM (FcμR) and IgD (FcδR) have been identified. The different biological activities of antibodies of different isotypes are based in part on their ability to bind to different FcR expressed on different immune (effector) cells (Fridman, W. H. (Sept. 1991) The FASEB Journal Vol. 5. 2684–2690). Murine antibodies, which are directed against FcRs have been made (See e.g. U.S. Pat. No. 4,954,617 entitled Monoclonal Antibodies To Fc Receptors for Immunoglobulin G on Human Mononuclear Phagocytes and International Patent Application Publication No. WO 91/05871 entitled Monoclonal Antibody Specific For IgA Receptor).

Murine monoclonal antibodies can be useful as human therapeutics and can be produced free of contamination by human pathogens such as the hepatitis or human immunodeficiency virus. However, use of murine monoclonal antibodies in some human therapies, have resulted in the development of an immune response to the "foreign" murine proteins. This response has been termed a human anti-mouse antibody or HAMA response (Schroff, R. et al. (1985), *Cancer Res.*, 45, 879–885) and is a condition which causes serum sickness in humans and results in rapid clearance of the murine antibodies from an individual's circulation. The immune response in humans has been shown to be against both the variable and the constant regions of murine immunoglobulins.

Recombinant DNA technology can be used to alter antibodies, for example, by substituting specific immunoglobulin regions from one species with immunoglobulin regions from another species. Neuberger et al. (Patent Cooperation Treaty Patent Application No. PCT/GB85/00392) describes a process whereby the complementary heavy and light chain variable domains of an Ig molecule from one species may be combined with the complementary heavy and light chain Ig constant domains from another species. This process may be used to substitute the murine constant region domains to create a "chimeric" antibody which may be used for human therapy. A chimeric antibody produced as described by Neuberger et al. has a human Fc region for efficient stimulation of antibody mediated effector functions, such as complement fixation, but still has the potential to elicit an immune response in humans against the murine ("foreign") variable regions.

Winter (British Patent Application Number GB2188538A) describes a process for altering antibodies by substituting the complementarity determining regions (CDRs) with those from another species. This process may be used to substitute the CDRs from the murine variable region domains of a monoclonal antibody with desirable binding properties (for instance to a human pathogen) into human heavy and light chain Ig variable region domains. These altered Ig variable regions may then be combined with human Ig constant regions to create antibodies which are totally human in composition except for the substituted murine CDRs. The "reshaped" or "humanized" antibodies described by Winter elicit a considerably reduced immune response in humans compared to chimeric antibodies because of the considerably less murine components. Further, the half life of the altered antibodies in circulation should approach that of natural human antibodies. However, as stated by Winter, merely replacing the CDRs with complementary CDRs from another antibody which is specific for an antigen such as a viral or bacterial protein, does not always result in an altered antibody which retains the desired binding capacity. In practice, some amino acids in the framework of the antibody variable region interact with the amino acid residues that make up the CDRs so that amino acid substitutions into the human Ig variable regions are likely to be required to restore antigen binding.

Bispecific molecules, (e.g., heteroantibodies) comprising an anti-Fc receptor portion and an anti-target portion have been formulated and used therapeutically, e.g., for treating cancer (e.g. breast or ovarian) or pathogenic infections (e.g., HIV) (See, e.g., International Patent Application Publication No. WO 91/05871 entitled Bispecific Heteroantibodies With Dual Effector Functions; and International Patent Application Publication No. WO 91/00360 entitled Bispecific Reagents for AIDS Therapy). In addition, bispecific molecules, which recognize antigens and antigen presenting cells can be administered to a subject to stimulate an immune response (See, e.g., International Patent Application Publication No. WO 92/05793 entitled Targeted Immunostimulation With Bispecific Reagents).

SUMMARY OF THE INVENTION

In one aspect, the invention features multispecific, multivalent molecules, which minimally comprise an anti-Fc receptor portion, an anti-target portion and optionally an anti-enhancement factor (anti-EF) portion. In preferred embodiments, the anti-Fc receptor portion is an antibody fragment (e.g., Fab or (Fab')$_2$ fragment), the anti-target portion is a ligand or antibody fragment and the anti-EF portion is an antibody directed against a surface protein involved in cytotoxic activity. In a particularly preferred embodiment, the recombinant anti-FcR antibodies, fragments or ligand are "humanized" (e.g., have at least a portion of a complementarity determining region (CDR) derived from a non-human antibody (e.g., murine) with the remaining portion(s) being human in origin).

In another aspect, the invention features methods for generating multispecific molecules. In one embodiment, both specificities are encoded in the same vector and are expressed and assembled in a host cell. In another embodiment, each specificity is generated recombinantly and the resulting proteins or peptides are conjugated to one another via sulfhydryl bonding of the C-terminus hinge regions of the heavy chain. In a particularly preferred embodiment, the hinge region is modified to contain only one sulfhydryl residue, prior to conjugation.

Recombinant antibodies and multispecific molecules generated therefrom can be engineered to have increased affinity and specificity. Further, humanized antibodies are typically less immunogenic when administered to a human. Other features and advantages of the present invention will become better understood by reference to the following Detailed Description and Claims.

BRIEF DESCRIPTION OF THE DRAWINGS

FIG. 1 is a diagram showing the nucleotide and amino acid residue sequences of a portion of the hinge region of a humanized Fcγ RI antibody, H22. [A] that was altered to produce a truncated single-sulfhydryl version [B] and then altered further to engineer two unique cloning sites [C]. Underlined nucleotides indicate changes from the previous sequence. Overlined nucleotides are the recognition sequences for the indicated restriction sites.

FIG. 10 shows the amino acid sequence of the H22Fd-HRG fusion protein.

FIG. 11 is a histogram indicating the percentage of specific PC-3 or SKBr-3 tumor cell killing resulting from incubation of these cells with interferon-γ-treated monocytes and a 1:3 or 1:30 dilution of supernatant from myeloma cells expressing an H22-heregulin fusion protein.

FIG. 24, panel A, shows the amino acid sequence of oligonucleotides encoding the wildtype (TT830) and mutant (TT833) tetanus toxin peptides. Panel B is a diagram of an H22Fd-TT fusion protein.

FIGS. 39(A–B) shows the nucleic acid sequence of the single chain humanized anti-Fc$\gamma$RI antibody and the amino acid sequence encoded by the nucleic acid.

FIGS. 40(A–C) shows the nucleic acid sequence of the single chain bispecific molecule having one binding specificity for the Fc$\gamma$RI and one binding specificity for CEA and the amino acid sequence encoded by the nucleic acid.

DETAILED DESCRIPTION

Multispecific Molecules

Figure 2:
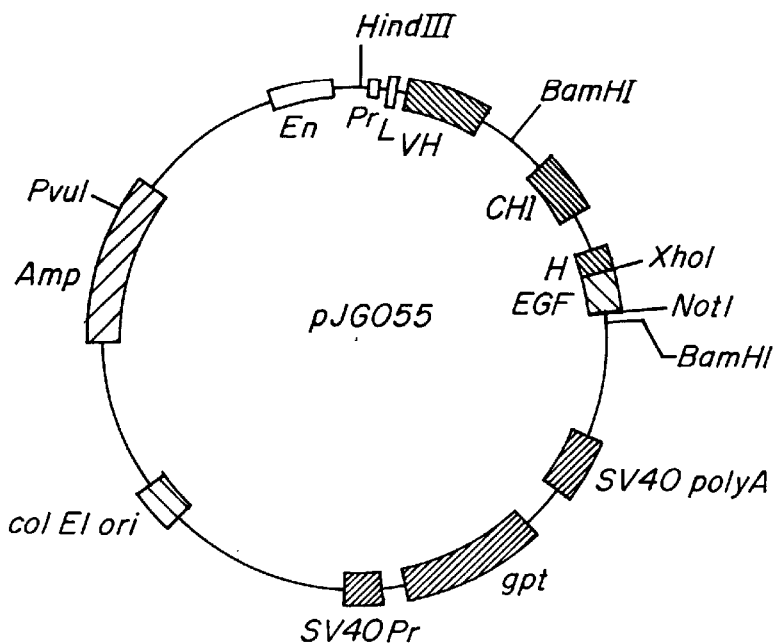
FIG. 2 is a schematic representation of the heavy chain-EGF fusion expression construct pJG055.

The instant invention relates to recombinant multispecific molecules. Multispecific molecules can include bispecific molecules comprised of an anti-Fc receptor portion and an anti-target portion, wherein at least one of said portions is constructed using recombinant DNA techniques. Multispecific molecules can also include molecules, which are comprised of more than one anti-Fc receptor portion or anti-target portion; or molecules comprised of at least one anti-Fc receptor, one anti-target portion and additionally a portion or portions that recognize another molecule, wherein at least one of said portions is constructed using recombinant DNA techniques.

An "anti-Fc receptor portion" refers to an antibody, a functional antibody fragment (e.g., Fab fragment) or a ligand that recognizes and binds an Fc receptor on an effector cell. Preferred antibodies for use in the subject invention bind the Fc receptor on an effector cell at a site which is not bound by endogenous immunoglobulin. Most preferably, the anti-Fc receptor portion binds a human Fc$\gamma$R (i.e., Fc$\gamma$RI, Fc$\gamma$RII or Fc$\gamma$RIII). Preferred humanized anti-Fc$\gamma$R monoclonal antibodies are described in PCT application WO 94/10332 and U.S. Pat. No. 4,954,617, the teachings of which are fully incorporated herein by reference).

An "effector cell", as used herein refers to an immune cell. Specific effector cells express specific Fc receptors and carry out specific immune functions. For example, monocytes, macrophages, neutrophils and dendritic cells, which express Fc$\gamma$RI are involved in both specific killing of target cells and presenting antigens to other components of the immune system. The expression of a particular FcR on an effector cell can be regulated by humoral factors such as cytokines. For example, expression of Fc$\gamma$RI has been found to be up-regulated by interferon gamma (IFN-$\gamma$). This enhanced expression increases the cytotoxic activity of Fc$\gamma$RI cells against targets.

The recombinant antibodies or antibody fragments, which specifically bind to an Fc receptor are preferably "humanized" i.e. derived from a human antibody, but having at least a portion of a complementarity determining region (CDR) derived from a non-human antibody. The portion being selected to provide specificity of the humanized antibody for a human Fc receptor. The humanized antibody has CDRs derived from a non-human antibody and the remaining portions of the antibody molecule are human.

The antibody may be whole, i.e. having heavy and light chains or any fragment thereof, e.g., Fab or (Fab')$_2$ fragment. The antibody further may be a light chain or heavy chain dimer, or any minimal fragment thereof such as a Fv or a single chain construct as described in Ladner et al. (U.S. Pat. No. 4,946,778, issued Aug. 7, 1990), the contents of which is expressly incorporated by reference.

The humanized antibody or fragment may be any human antibody capable of retaining non-human CDRs. The preferred human antibody is derived from known proteins NEWM and KOL for heavy chain variable regions (VHs) and REI for Ig kappa chain, variable regions (VKs).

The portion of the non-human CDR inserted into the human antibody is selected to be sufficient for allowing binding of the humanized antibody to the Fc receptor. A sufficient portion may be selected by inserting a portion of the CDR into the human antibody and testing the binding capacity of the created humanized antibody using the enzyme linked immunosorbent assay (ELISA).

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor. A non-human CDR derived from a murine monoclonal antibody (mab), mab 22, is described in International Patent Application Publication No. WO 94/10332, the contents of which are fully incorporated herein by reference. The mab 22 antibody is specific to the Fc receptor and further is described in U.S. Pat. No. 4,954,617, issued Sep. 4, 1988, the contents of which are also expressly incorporated by reference. The humanized mab 22 antibody producing cell line was deposited at the American Type Culture Collection on Nov. 4, 1992 under the designation HA022CL1 and has the accession no. CRL 11177.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Patent Application Publication Number: WO 94/10332 entitled, Humanized Antibodies to Fc Receptors for Immunoglobulin G on Human Mononuclear Phagocytes.

In addition to an anti-Fc receptor portion, the claimed multispecific molecules can comprise an "anti-target portion", i.e. an antibody, a functional antibody fragment or a ligand that recognizes and binds a pathogen (e.g., virus, bacteria, fungi), a pathogen infected cell, a cancer or tumor cell (e.g., breast, ovarian, prostate, etc.) or other unwanted cell in a subject (e.g., a human or animal) or an antigen or modified form thereof. Additionally, the target portion may comprise or be directed against an antigen. A preferred embodiment contains an antigen that can be used to stimulate the immune system, for example, in instances of chronic infection, to deplete antigen in the circulation, and to treat tumors. A particularly preferred embodiment has an antigen that is attached to a multivalent molecule containing an anti-FcR antibody.

In a specific embodiment of the invention, the multispecific molecule contains a ligand. The ligand can be any ligand that interacts with a molecule. In a preferred embodiment, the ligand binds a protein, e.g., a surface protein on a target cell, such as a cancer cell. Preferred ligands include ligands to receptors, such as growth or differentiation factors. For example, a multivalent molecule can comprise an epidermal growth factor, or at least a portion or modified form that is capable of interacting with a receptor, e.g., an epidermal growth factor receptor. In another preferred embodiment of the invention, the ligand is a small peptide, such as bombesin, gastrin-releasing peptide (GRP), litorin, neuromedin B, or neuromedin C. The sequences of the peptides can be found, e.g., in U.S. Pat. No. 5,217,955, the content of which is incorporated herein by reference. The ligand can also be a modified form of any of these peptides. The modification can increase binding to the receptor, decrease binding, or not affect the binding to a receptor. The modification of the ligand can also transform an agonist into an antagonist, such that the ligand inhibit rather than stimulate cell proliferation. The modification of the ligand can be an addition, a deletion, a substitution, or a modification of at least one amino acid.

In a specific embodiment of the invention, a multivalent or bispecific molecule comprises an antigen. As used herein, the term "antigen" means any natural or synthetic immunogenic substance, a fragment or portion of an immunogenic substance, a peptidic epitope, or a hapten.

In one embodiment of the invention, a bi- or multispecific molecule is employed to target an antigen to the cell to enhance the processes of internalization and presentation by these cells, and utlimately, to stimulate an immune response therein. In a specific embodiment, the bispecific binding agent specifically binds the antigen (either directly, to an epitope of the antigen, or indirectly, to an epitope attached to the antigen) and, at the same time, binds a surface receptor of an antigen-presenting cell which can internalize antigen for processing and presentation. In another embodiment, the antigen is linked to the multi- or bispecific molecule and at the same time binds a surface receptor of an antigen-presenting cell. The receptor-binding component of these bi- or multispecific molecule (and thus the bi- or multispecific molecule, itself) binds the receptor of the antigen-presenting cell. In some instances, binding of the molecule occurs without the molecule substantially being blocked by the natural ligand for the receptor. As a result, targeting of the antigen to the receptor will not be prevented by physiological levels of the ligand and the targeted receptor will remain capable of binding the ligand and functioning.

One type of antigen can be an allergen. An "allergen" refers to a substance that can induce an allergic or asthmatic response in a susceptible subject. The list of allergens is enormous and can include pollens, insect venoms, animal dander dust, fungal spores and drugs (e.g. penicillin). Examples of natural, animal and plant allergens include proteins specific to the following genuses: Canine (*Canisfamiliaris*); Dermatophagoides (e.g *Dermatophagoides farinae*); Felis (*Felis domesticus*); Ambrosia (*Ambrosia artemiisfolia;* Lolium (e.g. *Lolium perenne* or *Lolium multiflorum*); Cryptomeria (*Cryptomeriajaponica*) Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*) Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

Many allergens are found in airborne pollens of ragweed, grasses, or trees, or in fungi, animals, house dust, or foods. As a class, they are relatively resistant to proteolytic digestion. Preferable allergens are those which bind to IgE on mast cells and basophils, thereby causing a type I anaphylaxis hypersensitivity reaction. When at least one specificity of the multivalent agent is for an epitope of the high affinity Fc receptor that is outside the ligand binding domain for IgG, this bispecific binding agent can decrease hypersensitivity in a subject. This is accomplished when the bispecific binding agent competes for an IgE-binding allergen before the allergen binds to IgE on a mast cell or basophil, thereby reducing the possibility of a type I hypersensitivity reaction. In addition, as a result of directing allergen to FcγR, a state of T cell tolerance to the allergen may be induced which interferes with IgE-mediated type I reactions. Tolerance can be accomplished by inducing IgG which competes with IgE for binding to allergen using doses of allergen substantially lower than those currently used.

In some cases, it may be desirable to couple a substance which is weakly antigenic or nonantigenic in its own right (such as a hapten) to a carrier molecule, such as a large immunogenic protein (e.g., a bacterial toxin) for administration. In these instances, the bispecific binding reagent can be made to bind an epitope of the carrier to which the substance is coupled, rather than an epitope of the substance itself.

The antigen that can be linked either directly, or indirectly, to a multi- or bispecific molecule of the invention can be soluble or particulate; it may carry B cell epitopes, T cell epitopes or both. The antigen can be bacterial, viral or parasitic in origin. Often, the antigen will comprise a component of the surface structure of a pathogenic organism. For example, the antigen can comprise a viral surface structure such as an envelope glycoprotein of human immunodeficiency virus (HIV) or the surface antigen of hepatitis virus. In addition, the antigen can be associated with a diseased cell, such as a tumor cell, against which an immune response may be raised for treatment of the disease. The antigen can comprise a tumor-specific or tumor-associated antigen, such as the Her-2/new proto-oncogene product which is expressed on human breast and ovarian cancer cells (Slamon et al. (1989) *Science* 244:707).

The cells of a subject can be exposed in vitro or in vivo to the multivalent molecules of the invention. The multivalent molecule can be used to target an antigen to antigen-presenting cells in culture. Immunocompetent cells are separated and purified from patient blood. The cells are then exposed to a multivalent molecule comprising the antigen or the cells can be exposed to the antigen together with a multivalent molecule having a binding specificity for the antigen. Targeted antigen-presenting cells will process the antigen and present fragments on their surface. After stimulation, the cells can be returned to the patient.

The method of this invention can be used to enhance or reinforce the immune response to an antigen. For example, the method is valuable for the treatment of chronic infections, such as hepatitis and AIDS, where the unaided immune system is unable to overcome the infection. It can also be used in the treatment of the acute stages of infection when reinforcement of immune response against the invading organism may be necessary.

The method can be used to reduce the dose of antigen required to obtain a protective or therapeutic immune response or in instances when the host does not respond or responds minimally to the antigen. Although generally desirable, the lowering of effective dose can be especially desirable when the antigen is toxic to the host such as is the case for allergies. Methods and uses for using bi- or multi-specific molecules comprising an antigen or comprising an ligand, e.g., an antibody interacting with an antigen, are further described in the published PCT application PCT/US91/07283.

In another embodiment of the invention, a multispecific molecule comprises an antigen that has been modified, such that its effect on T cell activation is modified upon presentation of the modified antigen to the T cell by an antigen presenting cell. Allan et al. have in fact shown that substitution of one or more amino acids of a peptide that stimulates T cells, e.g., stimulates T cell proliferation, can result in an antigen which fails to stimulate the T cell or which induces anergy in the T cell. Such modified peptides are termed Altered Peptide Ligands (APL). Accordingly, such APLs can be linked to bispecific or multispecific molecules having at least one binding specificity for the FcγRI. Upon phagocytosis of these molecules by antigen presenting cells and presentation to T cells, the proliferation of the T cells may be inhibited or anergized. Accordingly, administration to a subject of a multispecific molecule comprising (a) at least one altered peptide of an antigen which normally stimulates T cells, but which upon modification induces anergy of the T cells, and (b) at least one anti-FcγRI antibody will result in induction of tolerance of the subject to the antigen. Thus, such multi- or bispecific molecules can be used to tolerize a subject to a variety of antigens, e.g., auto-antigens. Thus, depending on the antigen used, the methods of the invention provide methods for increasing an immune response, i.e., by using an antigen which stimulates T cells, and the invention also provides methods for reducing an immune response, either by inhibiting T cell stimulation or by inducing anergy of the T cells.

The multispecific, multivalent molecules of the invention may also include an "anti-enhancement factor (anti-EF) portion". The "anti-enhancement factor portion" can be an antibody, functional antibody fragment or a ligand that binds to an antigen and thereby results in an enhancement of the effect of the anti-$F_c$ receptor portion or the anti-target portion. The "anti-enhancement factor portion" can bind an $F_c$ receptor or a target. A multivalent molecule comprising an anti-target portion that binds to one target cell antigen and an anti-enhancement factor portion that binds to a different target antigen is particularly useful where the target cell undergoes antigen modulation or antigenic variation (e.g., as has been described for certain parasites (such as trypanosomes). Alternatively, the anti-enhancement factor portion can bind an entity that is different from the entity to which the anti-target or anti-$F_c$ receptor portion binds. For example, the anti-enhancement factor portion can bind a cytotoxic T-cell (e.g. via CD2, CD3, CD8, CD28, CD4, CD40, ICAM-1 or other immune cell that results in an increased immune response against the target).

Methods for Making Multispecific Molecules

The multispecific molecules described above can be made by a number of methods. For example, both specificities can be encoded in the same vector and expressed and assembled in the same host cell. This method is particularly useful where the multi-specific molecule is a ligand×fab fusion protein as described in the following Example 2. A bispecific molecule of the invention can also be a single chain bispecific molecule, such as a single chain bispecific antibody, a single chain bispecific molecule comprising one single chain antibody and a ligand, or a single chain bispecific molecule comprising two ligands. Multivalent molecules can also be single chain molecules or may comprise at least two single chain molecules. Methods for preparing bi- or multivalent antibodies are for example described in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the single chain molecules to their specific targets can be confirmed by bispecific ELISA as described in the Examples herein.

Alternatively, each specificity of a multi specific molecule can be generated separately and the resulting proteins or peptides conjugated to one another. For example, two humanized antibodies can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

The bispecific molecules of the present invention can be prepared by conjugating the anti-FcR and anti-target portions using methods described in the following Example or those well-known in the art. For example, a variety of coupling or cross-linking agents can be used for covalent conjugation. Examples of cross-linking agents include protein A, carbodiimide, N-succinimidyl-S-acetyl-thioacetate (SATA), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, MA et al. (1985) Proc. Natl. Acad. Sci. USA 82:8648). Other methods include those described by Paulus (Behring Ins. Mitt. (1985) No. 78, 118–132); Brennan et al. (Science (1985) 229:81–83), and Glennie et al. (J. Immunol. (1987) 139: 2367–2375). Preferred conjugating agents are SATA and sulfo-SMCC, both available from Pierce Chemical Co. (Rockford, Ill.).

Therapeutic Uses for Multispecific Molecules

Based on their ability to bind FcR bearing immune cells and specific target cells, a specific multispecific molecule can be administered to a subject to treat or prevent a variety of diseases or conditions, including: cancer (e.g., breast, ovarian, small cell carcinoma of the lung), pathogenic infections (e.g., viral (such as HIV)), protozoan (such as Toxoplasma gondii), fungal (such as candidiasis); an autoimmunity (e.g. immune thrombocytopenia purpura and systemic lupus). The multispecific multivalent can also be administered prophylactically to vaccinate a subject against infection by a target cell.

For use in therapy, an effective amount of an appropriate multispecific molecule can be administered to a subject by any mode that allows the molecules to exert their intended therapeutic effect. Preferred routes of administration include oral and transdermal (e.g., via a patch). Examples of other routes of administration include injection (subcutaneous, intravenous, parenteral, intraperitoneal, intrathecal, etc.). The injection can be in a bolus or a continuous infusion.

A multispecific molecule can be administered in conjunction with a pharmaceutically acceptable carrier. As used herein, the phrase "pharmaceutically acceptable carrier" is intended to include substances that can be coadministered with a multispecific molecule and allows the molecule to perform its intended function. Examples of such carriers include solutions, solvents, dispersion media, delay agents, emulsions and the like. The use of such media for pharmaceutically active substances are well known in the art. Any other conventional carrier suitable for use with the molecules falls within the scope of the instant invention.

The language "effective amount" of a multispecific molecules refers to that amount necessary or sufficient to realize a desired biologic effect. For example, an effective amount of a multispecific molecule, in which the anti-target portion recognizes a pathogenic cell could be that amount necessary to eliminate a tumor, cancer, or bacterial, viral or fungal infection. The effective amount for any particular application can vary depending on such factors as the disease or condition being treated, the particular multispecific molecule being administered, the size of the subject, or the severity of the disease or condition. One of ordinary skill in the art can empirically determine the effective amount of a particular multispecific molecule without necessitating undue experimentation.

The following invention is further illustrated by the following examples, which should not be construed as further limiting. The contents of all references, pending patent applications and published patents, cited throughout this application are hereby expressly incorporated by reference.

EXAMPLES

Example 1

Production of Bispecific Antibody Comprising Murine or Humanized Antibodies Specific for an Fc Receptor and an Anti-her 2 neu Antibody Monoclonal Antibodies The anti-FcγRI monoclonal antibodies (mAbs), M22, M32.2 and 197 were purified from hybridoma supernatant by ion exchange chromatography and DZ33, a human anti-HIV-1 IgG1 mAb, was purified from hybridoma supernatant by protein A affinity chromatography (Pharmacia, Piscataway, N.J.) and gel filtration. M32.2 was deposited at the American Type Culture Collection, 10801 University Blvd., Manassas, Va. 20110-2209, USA on Jul. 1, 1987 and has been designated with ATCC Accession No. HB9469.

Cell Lines

The murine myeloma NSO (ECACC 85110503) is a non-Ig synthesizing line and was used for the expression of recombinant mAbs. NSO cells were cultivated in DMEM plus 10% fetal bovine serum (FBS, Gibco, Paisley, U.K.). SKBR-3 is a human breast carcinoma cell line which overexpresses the HER2/neu protooncogene (ATCC, Rockville, Md.) and was cultivated in Iscove's Modified Dulbecco's Medium (IMDM, Gibco, Grand Island, N.Y.). U937 is a monocytoid cell line that expresses FcγRI and was obtained from ATCC and grown in RPM-1640 plus 10% FBS (Gibco, Grand Island, N.Y.).

Cloning Murine Immunoglobulin V Region Genes

Cytoplasmic RNA from the murine hybridoma 22 was prepared as described in Favaloro et al. (Favaloro, J. R. Treisman and R. Kamen (1982) Transcription maps of polyoma-specific RNA: analysis by two-dimensional SI gel mapping. Meth. Enzvmol. 65:718). The Ig V region cDNAs were made from RNA via reverse transcription initiated from primers CG1FOR and CK2FOR as described in International Patent Application Publication Number WO 94/10332 entitled, Humanized Antibodies to Fc Receptors for Immunoglobulin G on Human Mononuclear Phagocytes. The cDNA synthesis was performed under standard conditions using 100 U MMLV reverse transcriptase (Life Technologies, Paisley, UK). The $V_H$ and $V_K$ cDNAs were amplified by PCR, (Orlandi, R., D. H. Güssow, P. T. Jones and G. Winter (1989) (Cloning immunoglobulin variable domains for expression by the polymerase chain reaction), Proc. Natl. Acad. Sci. USA 86:3833), using the cDNA primers in concert with SH2BACK and VK7BACK as described in International Patent Application Publication Number WO 94/10332. Amplified $V_H$ and $V_K$ DNA were purified, cloned into M13, and sequenced by the dideoxy method using T7 DNA polymerase (Pharmacia, Piscataway, N.J.).

Construction of Chimeric Antibody Genes

To facilitate cloning of murine V region DNA into expression vectors, restriction sites were placed in close proximity to the termini of both M22 V region genes. For $V_H$, a 5' PstI site and a 3' BstEII site were introduced into a cloned murine $V_H$ gene by PCR using VH1BACK and VH1FOR (Id.). For $V_K$ a 5' PvuII site and a 3' Bgl II site were introduced into a cloned murine $V_K$ gene by PCR using primers VK1BACK and VK1FOR (Id.). In some instances, these primers changed one or more amino acids from those naturally occurring. These V region genes (ChVH and ChVK) were cut with the appropriate restriction enzymes and cloned into M13VHPCR1 and M13VKPCR1 (Id.) which contain an Ig promoter, signal sequence and splice sites. The DNA were excised from Ml 3 as HindIII-BamHI fragments and cloned into the expression vectors pSVgpt and pSVhyg containing human IgG1, (Takahashi, N. et al., (1982), Structure of human immunoglobulin gamma genes: implications for evolution of a gene family, *Cell,* 29:671), and human kappa constant, (Hieter, R. A. et al., (1980) Cloned human and mouse kappa immunoglobulin constant and J region genes conserve homology in functional segments, *Cell* 22:197), region genomic DNA.

Construction of Humanized Antibody Genes

Two humanized heavy chains were constructed and were based on human $V_H$s of NEWM, (Poljak, R. J. et al., Amino acid sequence of the $V_H$ region of a human mycloma immunoglobulin, (IgG New), *Biochemistry,* 16:3412), and KOL,(Marquat, M. et al., (1980) Crystallographic refinement and atomic models of the intact immunoglobulin molecule Kol and its antigen-binding fragment at 3.0A and 1.9A resolution, *J. Mol. Biol.* 141:369. The humanized light chain was derived from the human Bence-Jones protein REI, (Epp, 0. et al, (1974) Crystal and molecular structure of a dimer composed of the vandible portion of the Bence-Jones protein REI, *Eur. J. Biochem.* 45:513), with some framework region (FR) changes. The modifications were made to make the VK domain more typical of human subgroup I, and included replacement of Thr39, Leu104, Gln105 and Thr7 107 with Lys39, Val104, Glu105 and Lys107. In addition, Met4 was changed to Leu4 to accommodate a PvuII restriction site.

DNA containing the NEWM $V_H$ and REI $V_\kappa$ FRs with irrelevant CDRs were cloned into the vectors M13VHPCR1 and M13VKPCR1(Favaloro et al. Supra). DNA encoding the KOL $V_H$ was constructed by a series of sequential PCRs, using oligodeoxyribonucleotides encoding KOL FR amino acids and irrelevant CDRs. The constructs were then cloned into M13VHPCR1.

Oligodeoxyribonucleotides were synthesized to encode the mAB M22 CDRs which were flanked by nucleotides corresponding to the human FRs. For the humanized $V_H$ based on NEWM, the primers included murine FR amino acids Phe27, Ile28 and Arg71 since these were likely to influence antigen binding, (Chothia, C. and A. M. Lesk (1987), Canonical structures for the hypervariable regions of immunoglobulins, *J. Mol. Biol.,* 196:90 1; Tramontano, A. et al., (1990), Framework residue 71 is a major determinant of the position and conformation of the second hypervariable region in $V_H$ domains of immunoglobulins, *J. Mol. Biol,* 215:175). For the humanized $V_H$, murine amino acid Phe71was similarly included as a residue capable of affecting affinity, (Foote, J. and G. Winter, (1992), Antibody framework residues affecting the conformation of the hypervariable loops, *J. Mol. Biol.* 224:487. No murine FR residues were included in the KOL $V_H$. Oligodeoxyribonucleotides were 5'-phosphorylated and with the M13 universal forward primer annealed to the human V region genes cloned in M13 in reactions containing M13 ssDNA template. The DNA was extended and ligated with 2.5 U T7 DNA polymerase (United States Biochemicals, Cleveland, Ohio) and 0.5 U T4 DNA ligase (Gibco BRL, Grand Island, N.Y.). The mutated strand was preferentially amplified from the extension/ligation mixture using Ml 3 reverse sequencing primer with 1 U Vent DNA polymerase (New England Biolabs, Beverly, Mass.) and was then amplified by PCR using both M13 forward and reverse primers. Product DNA was cut with BamHI and HindIII, cloned into M13 and triple CDR-grafted mutants identified by DNA sequencing.

M13 clones containing the humanized V regions were sequenced in their entirety to ensure the absence of spurious mutations. RF DNA from the confirmed clones was digested with HindIII and BamHI, cloned into pSVgpt or pSVhyg and human IgGI or human kappa constant regions added exactly as described for the construction of the chimeric antibody genes.

Expression and Purification of Recombinant mAbs

Heavy (5 µg) and light (10 µg) chain expression vectors were digested with PvuI, ethanol precipitated and dissolved in 50 µl water. NSO cells (1–2×10$^7$) were harvested by centrifugation, resuspended in 0.5 ml DMEM and mixed with the DNA in a 0.4 cm electroporation cuvette. After 5 min. on ice the cells were given a single pulse of 170 V, 960 µF (GenePulser, Bio-Rad, Melville, N.Y.) and incubated further for 15 min. on ice. The cells were allowed to recover in DMEM for 24–48 hours. The medium was then made selective by the addition of mycophenolic acid (0.8 ug/ml) and xanthine (250 µg/ml). Aliquots of 200 µl were distributed into 96-well plates. After a further 10–12 days, cells from the wells containing the highest levels of antibody measured by ELISA were selected and cloned by limiting dilution.

Antibodies were purified from overgrown cultures by protein A affinity chromatography (Boehringer Mannheim, Lewes, U.K.) Concentrations were determined by measuring $A_{280nm}$ and confirmed by ELISA and SDS-PAGE.

ELISA for Measurement of Antibody Binding

The wells of a microtiter plate were coated with goat anti-human IgM antibodies (Sera-Lab, Crawley Down, U.K.) in 50 mM bicarbonate buffer, pH 9.6. The plate was blocked with 1% BSA and followed by the addition of a soluble fusion protein consisting of the extracellular domain of human FcγRI and human IgM heavy chain (sFcγRI-µ) obtained from transiently transfected COS cells (the expression vector was kindly provided by Dr. Brian Seed, Massachusetts General Hospital, Boston, Mass.). Recombinant 22 or control mAbs were then added in the presence of excess (2.2 µg/well) human IgG1 antibodies (Sigma, St. Louis, Mo.) that contained λ light chains to block the non-specific binding of the test mAbs via their Fc portion. Bound 22 mAbs were detected with peroxidase-labeled goat anti-human kappa chain antibodies (Sera-Lab, Crawley Down, U.K.) and o-phenylenediamine.

Fluoresceination of Antibodies

The pH of mAb solution was adjusted to 9.3 by the addition of 0.1 M $Na_2CO_3$. Fluorescein iso-thiocyanate (FITC) (Sigma, St. Louis, Mo.) was dissolved in DMSO at a concentration of 2mg/ml. Forty µg of FITC was added for each milligram of mAb and incubated for two hours at room temperature. The fluoresceinated mAb was separated from the free FITC by G-25 chromatography.

Preparation of Blood Cells

Buffy coats were prepared from heparinized whole venous blood. Whole blood was diluted with RPMI containing 5% dextran at a ratio of 2.5:1 (v/v). The erythrocytes were allowed to sediment for 45 minutes on ice, then the cells in the supernatant were transferred to a new tube and pelleted by centrifugation. The residual erythrocytes were removed by hypotonic lysis. The remaining lymphocytes, monocytes and neutrophils were kept on ice until use in binding assays. For some experiments, neutrophils were separated from mononuclear cells by ficoll hypaque (Pharmacia, Piscataway, N.J.) gradient separation. To up-regulate FcγRI, neutrophils and mononuclear cells were treated with cytokines. Cultures of mononuclear cells were incubated at 37° C., 5% $CO_2$ for 48 hours in teflon dishes at $4\times10^6$ cells/ml of RPMI containing 2.5% normal human serum type AB (Sigma, St. Louis, Mo.) and 500 IRU/ml IFN-γ (R&D Systems, Minneapolis, Minn.). Neutrophils were cultured for 48 hours (37° C., 5% $CO_2$) in AIM V media (Gibco, Grand Island, N.Y.) with 50 ng/ml G-CSF (Kindly provided by R. Repp, U. of Erlanger, Germany) and 500 IRU/ml IFN-γ.

Flow Cytometry

Cell binding assays were performed using 96-well microtiter plates as previously described, (Guyre, P. M. et al., Monoclonal antibodies that bind to distinct epitopes on FcγR are able to trigger receptor function. *J. Immunol.*, 143:1650). Briefly, cells were washed in PBS, pH 7.4 containing 2 mg/ml BSA and 0.05% $NaN_3$ (PBA), and adjusted to $2.0\times10^7$ cells/ml with PBA. FITC-labeled and unconjugated antibodies were prepared in PBA.

Cells (25 μl), antibody (25 μl) and human serum (25 μl), or human IgG (10 mg/ml, Sigma, St. Louis, Mo.) (25 μl), or PBA (25 μl) were added to the microtiter plate, and left on ice for 45–60 minutes. Unbound antibody was removed from the wells by washing the cells 3 times with PBA. The cells were fixed with 1% paraformaldehyde. Cell associated fluorescence was analyzed on a Becton Dickinson FACScan.

BsAb Coupling Procedure

BsAb were constructed using the method of Glennie et al, (Glennie, M. J. et al., (1987), Preparation and performance of bispecific F(ab' gamma)², antibody containing thioether-linked Fab' gamma fragments, *J.Immunol.*, 139:2367). mAbs 22 (both murine and humanized) and 520C9 (anti-HER2/neu) antibodies were produced by in vitro cultivation of the respective hybridoma cells. The antibodies were separately digested with pepsin to F(ab')₂, and subsequently reduced to Fab' by addition of 10 mM mercaptoethanolamine (MEA) for 30 minutes at 30° C. The Fab' fragments were applied to a Sephadex G-25 column equilibrated in 50 mM Na Acetate, 0.5 mM EDTA, pH 5.3 (4° C.). Ortho-phenylenedimaleimide (o-PDM, 12 mM) dissolved in dimethyl formamide and chilled in a methanol/ice bath was added (one half volume) to the murine 22 Fab' in the case of M 22x520C9, and to 520C9 Fab' in the case of H 22x520C9 and incubated for 30 minutes on ice.

The Fab'-maleimide was then separated from free o-PDM on Sephadex G-25 equilibrated in 50 mM Na Acetate, 0.5 mM EDTA, pH 5.3 (4° C.). For preparation of the BsAbs, the M22 Fab'-maleimide was added to the 520C9 Fab' or the 520C9 Fab'-maleimide was added to H22 Fab' at a 1:1 molar ratio. The reactants were concentrated under nitrogen to the starting volume using a Diaflo membrane in an Amicon chamber (all at 4° C.). After 18 hours the pH was adjusted to 8.0 with 1M Tris-HC1 , pH 8.0. The mixture was then reduced with 10 mM MEA (30 minutes, 30° C.) and alkylated with 25 mM iodoacetamide. The bispecific F(ab')₂ was separated from unreacted Fab's and other products by a Superdex 200 (Pharmacia, Piscataway, N.J.) column equilibrated in PBS.

Antibody Dependent Cellular Cytotoxicity (ADCC)

The HER2/neu over-expressing human breast carcinoma cells, SKBR-3, were used as targets for lysis by cytokine activated neutrophils (see preparation of blood cells). Targets were labeled with 100 μCi of $^{51}$Cr for 1 hour prior to combining with neutrophils and antibodies in a U-bottom microtiter plate. After incubation for 5 hours at 37° C. supernatants were collected and analyzed for radioactivity. Cytotoxicity was calculated by the formula: % lysis= (experimental CPM–target leak CPM/detergent lysis CPM– target leak CPM)x100%. Specific lysis=% lysis with antibody–% lysis without antibody. Assays were performed in triplicate.

Superoxide Induction

U937 cells were used for measuring the ability of H22 to trigger a superoxide burst via FcγRI, (Pfefferkom, L. C. and G. R. Yeaman (1994), Association of IgA-Fc receptors (FcxR) with FcεRIγ2 subunits in U937 cells, *J. Immunol.* 153:3228; Hallet, H. B. and A. K. Campbell (1983). Two distinct mechanisms for stimulating of oxygen - radical production in polymorphonuclear leucocytes, *Biochem J.* 216:459). U937 cells were cultured for five days in RPMI-1640 (Gibco, Grand Island, N.Y.) with 10% FBS (Hyclone, Logan, Utah) in the presence of 100 U/ml IFN-γ (Genentech, S. San Francisco, Calif.) to induce differentiation and increased expression of FcγRI. On the day of the experiment, these differentiated cells were incubated for 20 minutes in fresh RPMI-1640 with 10% FBS at 37° C. The cells were then pelleted and resuspended at a concentration of $3\times10^6$ cells/ml in PBS supplemented with 1 mM $CaCl_2$, 1 mM $MgCl_2$, 11 mM glucose, and 100 μg/ml BSA (Sigma, St. Louis, Mo.). To trigger the release of superoxide, 100μl of cells were added to 100 μl of a reaction solution containing 0.1 mM luminol (Sigma, St. Louis, Mo.), 0.5 mM sodium vanadate (Sigma, St. Louis, Mo.), and either mAb M22, H22, or 197 and placed in the luminometer at 22° C. Measurements of the spontaneous production of superoxide were made every 30 to 40 seconds starting immediately following the addition of the cells to the reaction solution in the luminometer. To compare the superoxide triggered by crosslinking FcγRI with M22, H22 or 197, each mAb was used at a concentration of 10 μg/ml. The production of superoxide in mV/sec was monitored for 20 minutes. MAb M22, M32.2 and 197 were added at various concentrations to establish the dose-responsiveness of superoxide production.

Results

Murine Ig V Region Genes

Ig V region cDNAs were prepared from M22 hybridoma RNA using primers specific for murine heavy and kappa constant regions and were amplified by PCR with the additional use of a series of primers based on sequences of known signal and/or 5' sequences of mature V regions. PCR products of the expected sizes for $V_H$ and $V_K$ were obtained using the SH2BACK/CG1FOR and VK7BACK/CK2FOR primer combinations. Amplified DNA was digested with appropriate restriction enzymes, cloned into M13 and the sequence in both directions determined from at least 24 independent clones. The deduced amino acid sequences are shown in SEQ.ID Nos. 29 and 30. The 4 N-terminal residues of $V_K$ are encoded by the VKBACK primer.

The M22 $V_H$ and $V_K$ are members of murine heavy chain subgroup IIID and kappa subgroup I, (Kabat, E. A. et al., (1991), *Sequences of Proteins of Immunological Interest*, 5th Ed., U.S. Department of Health and Human Services), respectively. Apart from the residue at L97, the amino acid sequence of the M22 $V_\kappa$ is identical to that from the murine anti-IgG mAb A17 (Shlomchik, M. et al., Variable region sequences of murine IgM anti-IgG monoclonal autoantibodies (rheumatoid factors). II Comparison of hybridonias derived bylipopolysaccharide stimulation and secondary protein immunization, *J. Exp. Med.* 165:970).

Humanized mAbs and Initial Characterization of their Binding

M22 $V_H$FR showed greater homology (79%) to KOL (human subgroup III) than to NEWM (57%) (human subgroup II). To see how this difference might affect binding, heavy chains were constructed based either on NEWM $V_H$ including the murine residues Phe27, Ile28 and Arg71, or on KOL $V_H$ with no murine FR amino acids. Both humanized $V_H$ were partnered with the same REI-derived humanized light chain.

The affinity of the humanized mAbs was initially assessed by ELISA measuring the binding to FcγRI/IgM heavy chain fusion protein. The data showed that the KOL $V_H$/REI $V_\kappa$ mAb had the same binding as the chimeric mAb whereas the NEWM $V_H$/REI $V_\kappa$ mAb exhibited an approximate 5- fold lower affinity. The low binding of a nonspecific human IgG1 mAb showed that >95% of binding of the humanized mAbs was via the Fv portion rather than through the Fc domain.

While additional changes to the NEWM FR would be expected to restore binding affinity these could create novel epitopes which might provoke an unwanted immunological response. The KOL $V_H$/REI $V_\kappa$ mAb, designated H22, was therefore chosen for further examination of its binding characteristics.

Functional Characterization of mAbH22

A series of binding experiments were performed to establish the specificity and isotype of the H22 antibody. Peripheral blood leukocytes stained with fluorescein-conjugated M22 or H22 demonstrated specific binding to monocytes with approximately $10^4$ binding sites per cell. In contrast, lymphocytes or unstimulated neutrophils had little or no specific binding (Table 1):

TABLE 1

Specific Binding of H22 to Monocytes

| Antibody | Monocytes | Lymphocytes | PMNs |
|---|---|---|---|
| M22 | 10,000[a] | <1000 | <1000 |
| H22 | 10,500 | <1000 | <1000 |

[a]Antibody sites per cell, average of duplicates

To demonstrate that the H22 binds to FcγRI at the same site as M22 and that it also binds as a ligand at the Fc binding domain, competition experiments with two anti-FcγRI murine mAb (M22 and M32.2) and a human IgG1 mAb were performed. Unconjugated H22 and M22 competed equivalently for either the binding of fluoresceinated M22 or fluoresceinated H22 in the presence of excess human IgG which saturated the Fc binding sites on FcγRI. As expected, the anti-FcγRI antibody M32.2 which binds to a different site on FcγRI than M22 (Guyre, P. M. et al., *J. Immunol.* 143:1650) was also unable to compete with the M22-FITC. In addition, the inhibition of H22-FITC by H22 and not by an irrelevant human IgG 1 mAb confirmed the specificity of FcγRI binding via the V regions of H22.

H22, but not M22, was able to compete for Fc mediated binding to FcγRI by a fluorosceinated human IgG1. This experiment demonstrated that the Fc portion of H22 but not M22 bound to the Fc binding domain of FcγRI. This is consistent with the ability of the Fc portion of human IgG1 antibodies, but not murine IgG1, to bind FcγRI with high affinity.

Since the humanization of M22 was primarily to increase its immunotherapeutic potential, the binding activity of H22 to monocytes and cytokine-activated neutrophlils was determined in the presence of human serum. H22-FITC bound with similar affinity to FcγRI on monocytes in the presence or absence of human serum. In contrast, the Fc-mediated binding of an irrelevant human IgG-FITC was completely inhibited by human serum. Likewise, H22-FITC bound with similar affinity to IFN-γ-treated neutrophils in the absence and in the presence of human serum. Collectively, the data demonstrated that H22 binds both via its V regions to a site distinct from the Fc binding domain and via its Fc region to the ligand binding domain of FcγRI. The former binding activity effectively overcomes antibody blockade of human IgG1.

Functional Activity of H22 BsAb

The foremost application of anti-FcγRI antibodies for immunotherapy is the development of BsAbs which link FcγRI-bearing effector cells to a tumor cell, a virus, or a virally-infected cell. Such BsAb have been developed with M22; therefore, a comparison was made of the ability of the M22 anti-tumor BsAb (520C9×M22) and a corresponding H22 BsAb (520C9×H22) to mediate cytotoxicity. These BsAbs consisted of H22 or M22 Fab' chemically conjugated to the Fab' of an anti-HER2/neu antibody (520C9), and thus were specific for the effector cell trigger molecule FcγRI and the tumor antigen.

Comparison of M22-derived and H22-derived BsAbs was done by ADCC assays. M22- and H22-derived BsAbs mediated the killing of HER2/neu overexpressing SKBR-3 cells. Both the murine and humanized BsAbs exhibited similar levels of lysis of antigen bearing target cells. In addition, both BsAb retained ADCC activity in the presence of human serum, while excess M22 F(ab')$_2$ resulted in complete inhibition of killing. Taken together these results show that the H22 BsAb-induced lysis is mediated through the M22 epitope and that the ADCC is FcγRI specific.

Finally, the ability of H22 and M22 to stimulate superoxide production by the monocyte-like cell line U937 was evaluated. M22, which binds to the FcγRI only by its V regions, induced a very low level oxygen burst, presumably because it is unable to cross-link the receptor efficiently. However, H22, which can cross-link FcγRI by binding as a ligand via its Fc domain and, additionally, as an antibody via its Fv, induced a more substantial release of superoxide.

Example 2

Generation of a Functional H22-Epidermal Growth Factor Fusion Protein

Materials and Methods

Expression Vectors and Cloning

Expression vectors for the genomic clones of the heavy (pSVgpt) and light (pSVhyg) chains of H22 are as described in International Patent Application Publication Number: WO 94/10332 entitled, Humanized Antibodies to Fc Receptors for Immunoglobulin G on Human Mononuclear Phagocytes. For the Fab-ligand fusion construct, it was unnecessary to alter the light chain. For the heavy chain, however, the CH2 and CH3 domains had to be removed and replaced with the coding sequences of the ligands. The heavy chain vector contains two BamHI sites, one in the intron between VH and CH1, and the other just downstream of CH3. Using the BamHI restriction sites, DNA encoding the constant domains were replaced by a truncated version encoding only CH1 and most of the hinge. To do this, the polymerase chain reaction (PCR) was utilized to engineer the new C-terminus of the heavy chain fragment with the alterations shown in FIG. 1.

The construct shown in FIG. 1 [C], consisting of a translation termination codon downstream of the cloning restriction sites, XhoI and NotI, and upstream of a BamHI site which was used to clone the new PCR generated CHI fragment downstream of VH, was used to generate the fusion protein constructs. The cloning sites, which are located downstream of most of the hinge in order to retain flexibility between the Fd and ligand domains, was used to insert DNA encoding EGF or other ligands. Also, the single Cys residue has been retained from the previous construct to allow conjugation for the formation of dimeric molecules.

DNA encoding the ligands were amplified by PCR to have a XhoI site on the N-terminus and a NotI site on the C-terminus of the coding region, and then inserted in the proper reading frame into the same sites of the newly engineered H22 heavy chain truncated fragment described above. cDNA encoding epidermal growth factor (EGF) was obtained from the ATCC (#59957). Only DNA encoding the 53 amino acid residues of mature EGF out of the approximately 1200 residue precursor was cloned beginning with Asn 971 and ending with Arg 1023 (Bell, G. I., Fong, N. M., Stempien, M. M., Wormsted, M A., Caput, D., Ku. L., Urdea, M. S., Rall, L. B. & Sanchez-Pescador, R. Human Epidermal Growth Factor Precurser: cDNA Sequence, Expression In Vitro and Gene Organization. Nucl. Acids Res. 14: 8427–8446,1986.).

Expression

The murine myeloma NSO (ECACC 85110503) is a non-Ig synthesizing line and was used for expression of the fusion proteins. The final expression vector, a pSVgpt construct with DNA encoding H22 Fd fused in frame to EGF (shown in FIG. 2) was transfected by electroporation using a BioRad Gene Pulser to NS0 which had been previously transfected with the pSVhyg construct containing DNA encoding H22 light chain. These polypeptides were expressed by an Ig promoter and Ig enhancer present in the vectors, and secreted by the mAb 22 heavy chain signal peptide located on the N-terminus of the constructs. One or two days after transfection, mycophenolic acid and xanthine were added to the media to select for cells that took up the DNA. Individual growing colonies were isolated and subcloned after binding activity was demonstrated by ELISA.

Purification

Cells expressing the H22-EGF fusion protein were subcloned and expanded.

Figure 3:
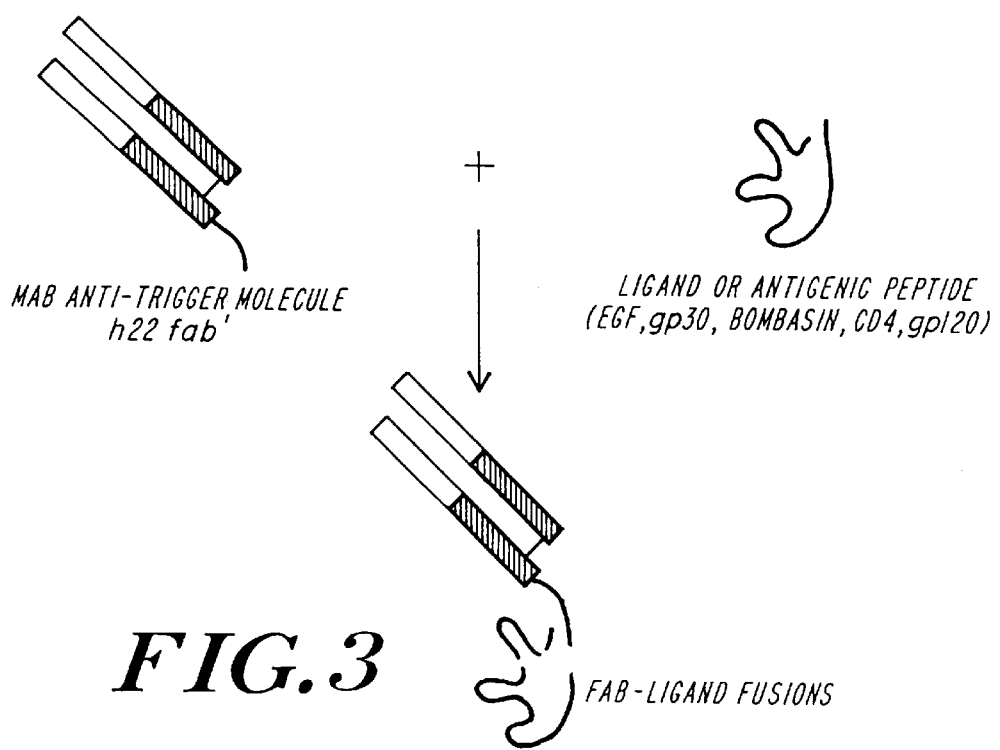
FIG. 3 is a schematic representation of the generation of anti-Fc receptor-ligand bispecific molecules.

The fusion protein-expressing clone was expanded and grown in spinner cultures and the supernatant was clarified and concentrated. Small scale purification was performed by affinity chromatography on an anti-human kappa chain affinity column (Sterogene. Carlsbad, Calif.). The purified protein was analyzed by SDS-PAGE on a 5–15% acrylamide gradient gel under nonreducing conditions. FIG. 3 is a schematic representation of the generation of anti-Fc receptor-ligand fusion proteins.

Bispecific flow cytometry

Figure 4:
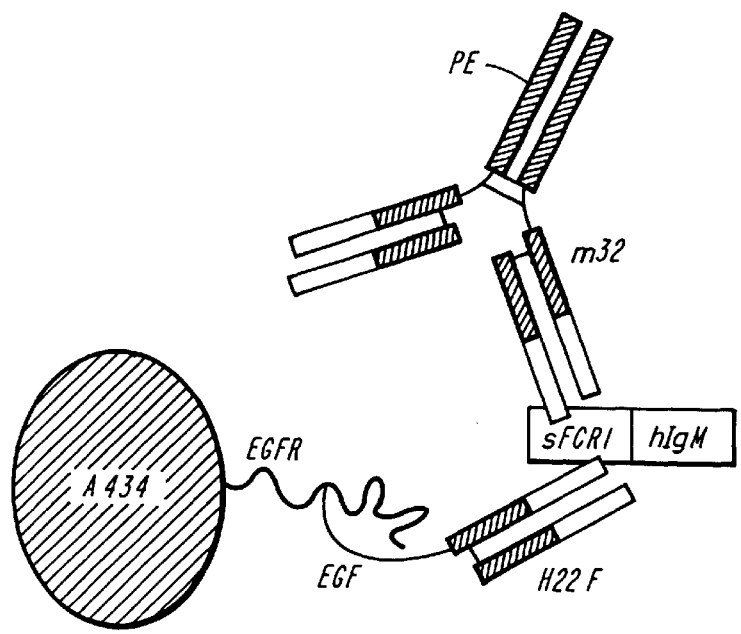
FIG. 4 is a schematic representation of the flow cytometric assay used for testing the activity of the humanized Fc γ receptor-epidermal growth factor fusion protein.

To show that the fusion protein is capable of binding both FcγRI and EGFR simultaneously, a flow cytometric assay has been developed (FIG. 4). In this assay different concentrations of H22-EGF fusion protein or the bispecific antibody, BsAb H447 (H22÷H425, a humanized version of the murine monoclonal antibody M425, which binds EGFR at the ligand binding site (E. Merck) was incubated with A431 cells, a cell line which expresses the EGF receptor (EGFR) (ATCC, Rockville, Md.). After washing, a supernatant containing a fusion protein consisting of the extracellular domain of FcγRI and the Fc portion of human IgM was added. Finally, a Phycoerythrin (PE)-labeled mAb (32.2), that binds FcγRI at a site that is distinct from that bound by mAb 22, was added. The cells were then analyzed by FACSCAN. Alternatively, binding to EGFR was blocked by excess (100 μg/ml) whole murine mAb 425 (E. Merck), and binding of bsAb or fusion protein was detected by PE-labeled anti-human IgG.

ADCC

ADCC mediated by the fusion protein was determined using a $^{51}Cr$ killing assay. The EGFR overexpressing cell line, A431, was used as targets for lysis by human monocytes cultured in γ-interferon (IFN-γ) for 24 hours. Targets were labeled with 100 μCi of $^{51}Cr$ for 1 hour prior to combining with effector cells and antibodies in a U-bottom microtiter plate. After incubation for 5 hours at 37° C. supernatants were collected and analyzed for radioactivity. Cytotoxicity was calculated by the formula: % lysis= (experimental CPM−target leak CPM/detergent lysis CPM− target leak CPM)×100%. Specific lysis=% lysis with antibody−% lysis without antibody. The ability of the fusion protein to mediate ADCC was compared with that of the respective BsAb. The assay was also performed in the presence of 25% human serum to demonstrate that IgG or other factors found in human serum will not inhibit fusion protein-mediated ADCC.

Results

Purification

NS0 cells expressing the H22 kappa chain were transfected with the H22-EGF heavy chain construct and clones selected for resistance to mycophenolic acid and xanthine were expanded and the fusion protein was affinity-purified from the supernatant on an anti-human kappa column (Sterogene, Carlsbad, Calif.). The purified protein was analysed by SDS-PAGE. The purified protein migrated at an apparent molecular weight of 50–55 kDa, indicating that the fusion protein is expressed as a monomer, not a disulfide-linked dimer. In addition, a band was seen at an apparent molecular weight of 25 kDa and is probably free light chain.

cl Binding Specificity

Figure 5:
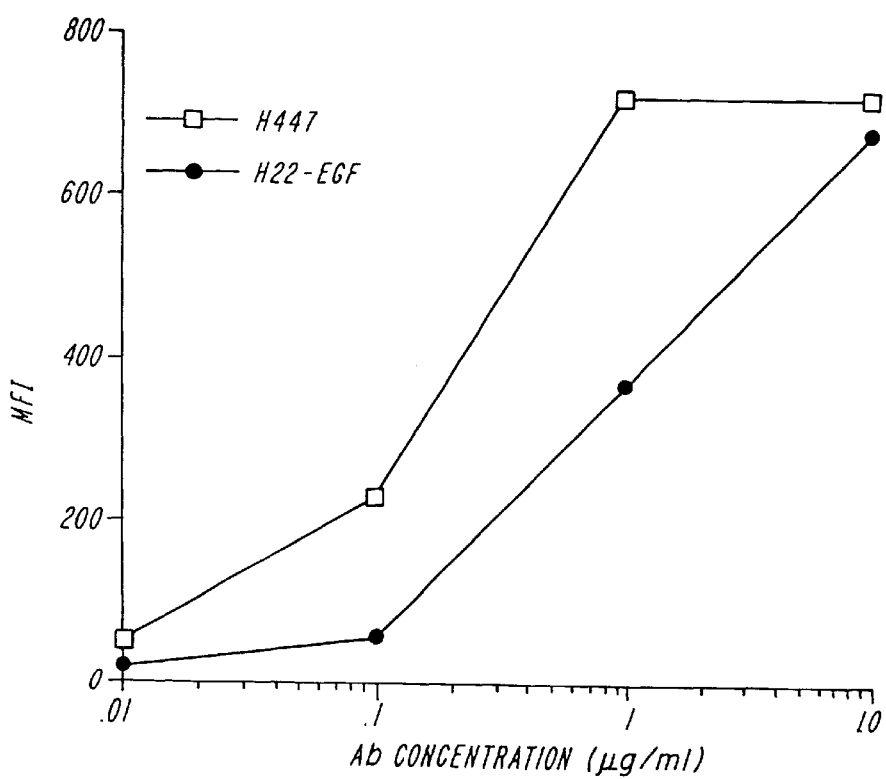
FIG. 5 is a graph, which plots Mean Fluorescence Intensity (MFI) an indication of the binding of various concentrations of epidermal growth factor (EGF) fusion protein (H22-EGF fusion) and the fully humanized bispecific (BsAb) H447 to EGF receptor (EGFR) expressing 1483 cells.

To demonstrate that the fusion protein could bind FcγRI and EGFR simultaneously a bispecific FACS assay was devised. FIG. 5 shows that both the chemically-linked, fully-humanized BsAb H447 (H22 (anti-FcγRI)×H425), which was made as described in the following Example 3, and the H22-EGF fusion protein bound EGFR on A431 cells and soluble FcγRI simultaneously in a dose-dependent fashion.

Figure 6:
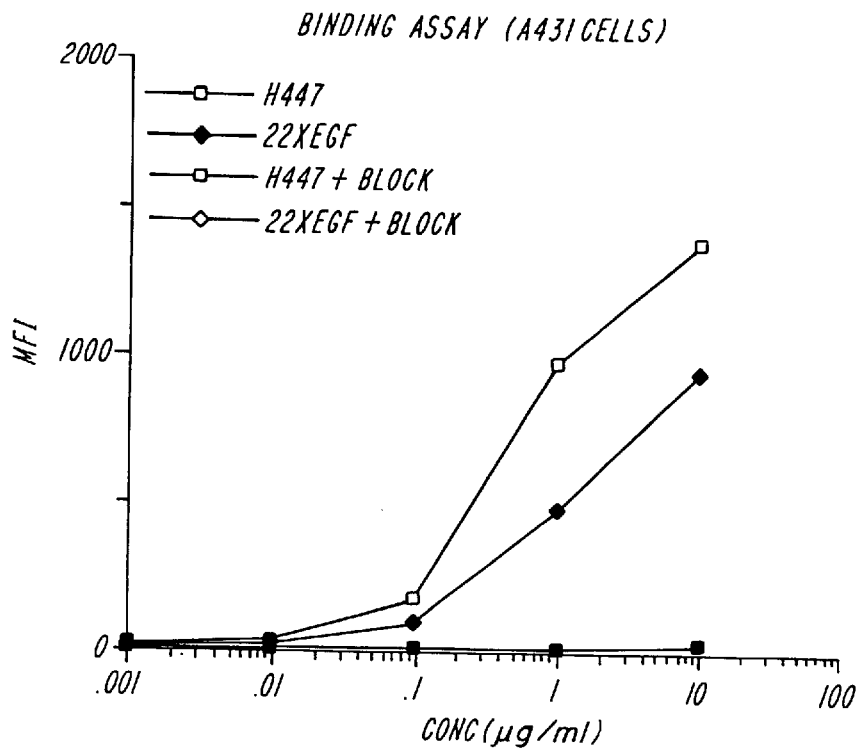
FIG. 6 is a graph, which plots the binding of various concentrations of the EGF fusion protein or the BsAb H447 to A431 cells in the presence and absence of murine antibody M425, which binds EGFR.

The EGFR-specificity of the fusion protein was demonstrated by the ability of the murine mAb, M425, which binds EGFR at the ligand binding site, to inhibit fusion protein or H22×H425 binding. Various concentrations of either the BsAb H447, or of the H22-EGF fusion protein were incubated with A431 cells in either the presence or absence of an excess of M425. FIG. 6 shows that binding of both the BsAb and the fusion protein were inhibited by M425, demonstrating the specificity of the fusion protein for EGFR.

ADCC

Figure 7:
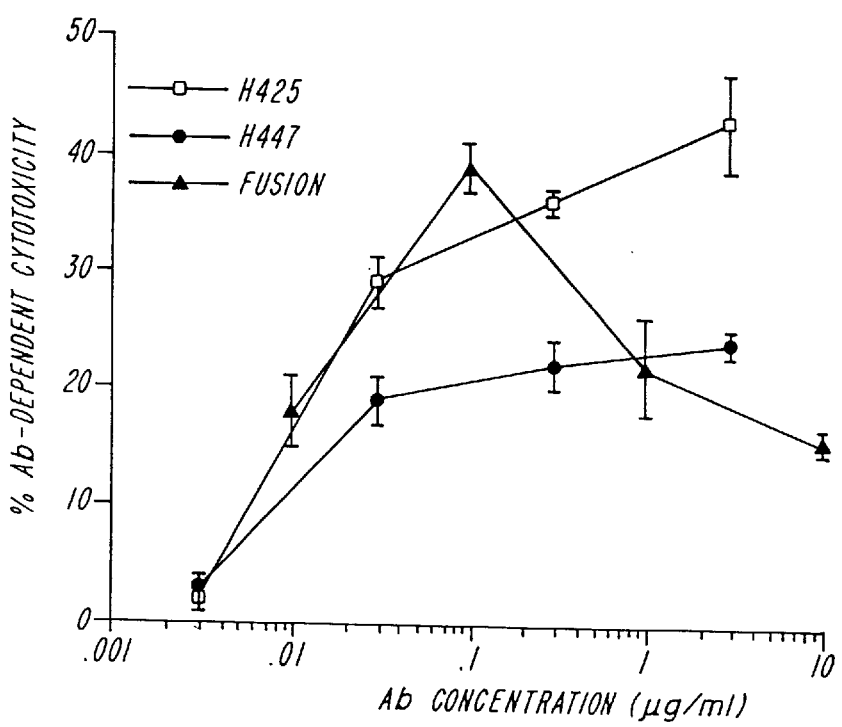
FIG. 7 is a graph, which plots the antibody dependent cytotoxicity (ADCC) resulting from the binding of various concentrations of the EGF fusion protein, BsAb H447 or the H425 antibody to A431 cells.
Figure 8:
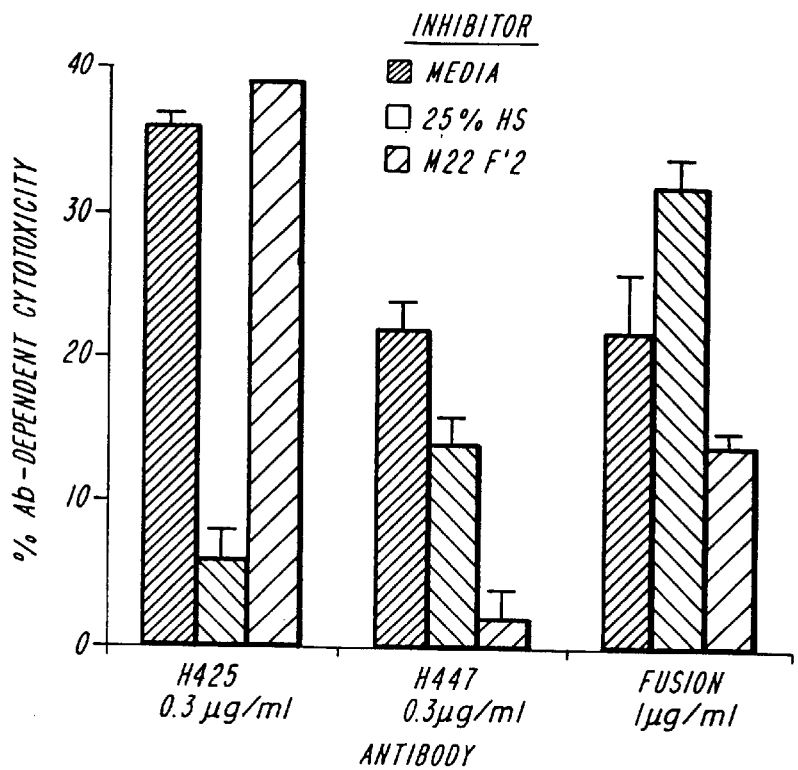
FIG. 8 is a bar graph which plots the ADCC resulting from the binding of EGF fusion protein, BsAb H447 or the H425 antibody in the presence of media alone, media containing 25% human serum (HS) or media containing a fab fragment of the Fcγ receptor antibody m22.

The ability of the fusion protein to mediate ADCC was analyzed using A431 cells as targets. Human monocytes cultured for 24 hours in the presence of IFN-γ were used as effector cells. FIG. 7 demonstrates the whole antibody, H425, the BsAb H447 (H22×H425) and the fusion protein mediated dose-dependent lysis of A431 cells. FIG. 8 demonstrates that while ADCC mediated by the whole antibody is inhibited by 25% human serum (25% HS), ADCC mediated by the fusion protein was not inhibited by human serum and, in this particular experiment, fusion protein-mediated ADCC was enhanced by human serum. These results support the clinical utility of these molecules by demonstrating that the fusion protein was capable of killing EGFR-overexpressing cells, even in the presence of FcγRI-expressing effector cells as would be present in vivo.

Growth Inhibitory Properties of H22-EGF Fusion Proteins

Although EGF acts to stimulate growth of normal cells that express receptors for it, EGF also can act to inhibit growth of tumor cells that over-express EGF-R (Barnes, D. W. (1982) *J. Cell Biol.* 93:1, MacLeod, C. L. et al. (1986) *J. Cell. Physiol.* 127:175). The ability of EGF and the H22-EGF fusion protein to inhibit the growth of A431 cells was examined as follows.

$2 \times 10^4$ A431 cells were added to six well plates in complete media alone or in media containing various concentration of either EGF, H22-EGF, the Fab fragment of H22, or the F(ab')$_2$ fragment of H425. Viable cells were counted after seven days using a hemocytometer. The analyses were performed in duplicate and reported as means +/− standard deviations.

Figure 9:
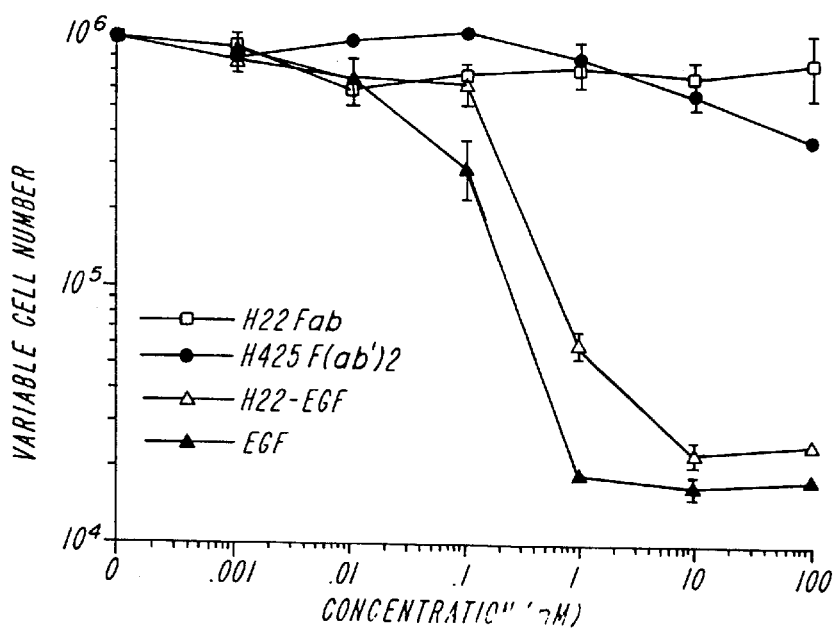
FIG. 9 is a schematic diagram representing the number of viable A431 cells cultured in the presence of various amounts of EGF, H22-EGF, the Fab fragment of H22 (H22 Fab), or the F(ab')₂ fragment of H425 (H425 F(ab')2).

The results are presented in FIG. 9. These results indicate that EGF and H22-EGF significantly inhibited cell growth in a dose dependent fashion. On the contrary, the F(ab')2 fragment of H425 which had some inhibitory activity only at high concentrations and the Fab fragment of H22 had no growth inhibiting activity.

Thus, H22-EGF is able to bind to both FcγRI and EGF-R simultaneously, indicating that the molecule had folded properly and had maintained the flexibility required to bind both receptors at the same time. Furthermore, H22-EGF inhibited proliferation of the EGF-R expressing tumor cell line, A431, indicating that, similar to EGF, the H22-EGF fusion protein is capable of signaling through the EGF-R. H22-EGF also mediates potent killing of A431 cells in the presence of FcγRI expressing effector cells. Thus, H22-EGF mediates both cytotoxic and cytostatic effects on EGF-R expressing cells. Administration of H22-EGF to a subject having a tumor will result in recruitment of the body's natural cytotoxic effector cells to mediate killing of the tumor cells by potentially three different modes—cytotoxicity, growth inhibition, and phagocytosis. Furthermore, in addition to cell mediated cytotoxicity of the tumor cells, the effector cells recruited by H22-EGF may also further augment anti-tumor immunity by secreting inflammatory cytokines and/or by processing and presenting tumor antigens to tumor specific T cells.

Example 3

H22-Heregulin (H22-gp30) Fusion Protein Mediates Tumor Cell Killing

Heregulin (HRG) is a ligand for the HER3 and HER4 molecules. Both of these receptors may form heterodimers with HER2, a molecule which is overexpressed in some breast cancer cells. The affinity of HRG for HER3 and HER4 increases significantly when these molecules from heterodimers with HER2. This example demonstrates that a bispecific molecule, comprising heregulin and a binding specificity for the FcγRI inhibits growth of a tumor cell line and mediates fusion protein dependent cytotoxicity of these cells in the presence of FcγRI-bearing cytotoxic effector cells.

The H22-heregulin fusion protein was constructed in the same manner as the H22-EGF fusion protein described in Example 2. Briefly, genomic DNA encoding the Fd fragment of humanized anti-FcγRI mAb, H22, was fused to cDNA encoding the EGF domain of the β2 form of HRG. The amino acid sequence of the H22-HRG fusion protein (SEQ ID NO:4) is shown in FIG. 10. This fusion protein comprises amino acids 171–239 of the heregulin β2 shown in U.S. Pat. No. 5,367,060. Other portions of heregulin β2, as well as portions of other heregulin molecules, such as those disclosed in U.S. Pat. No. 5,367,060 can also be used. The resulting H22Fd-HRG expressing vector was transfected into a myeloma cell line previously transfected with a vector containing DNA encoding the H22 kappa light chain. The resultant fusion protein was expressed predominantly as a monomer, even though the protein contains a free Cys residue in the hinge region of the H22 Fab component. Flow cytometry showed that this fusion protein was able to bind to the HER2 overexpressing tumor cell line, SKBR-3, as well as to FcγR-expressing cells.

To test the biological activity of the H22Fd-HRG fusion protein, supernatant from the myeloma cells expressing this fusion protein was diluted three fold or thirty fold and added to PC-3 cells or SKBR-3 tumor cells expressing HER2, HER3, and HER4 in the presence of IFN-treated monocytes at a ratio of 100:1 monocytes to target tumor cells. The monocytes were treated with IFN-γ and the target cells were labeled with $^{51}$Cr as described in Example 2. The % of specicific lysis was calculated as indicated in Example 2. The results are presented in FIG. 11. The results indicate that about 45% of SKBR3 cells and up to about 49% of PC-3 cells are lysed upon incubation of the cells with the supernatant diluted 3 fold.

This fusion protein inhibits growth of SKBR-3 tumor cells and mediates fusion protein dependent cytotoxicity of these cells in the presence of FcγRI-bearing cytotoxic effector cells. Thus, the results of this example show that an anti-FcγRI-heregulin fusion protein can mediate anti-tumor cytotoxic activities under physiologic conditions and indicate that such a fusion protein will have therapeutic utility in the treatment of various cancers.

Example 4

H22-Bombesin Fusion Protein Mediates Tumor Cell Killing

The H22-bombesin fusion protein was constructed similarly to the H22-EGF fusion protein described above.

However, since bombesin is a short peptide (14 amino acid residues), instead of amplifying cDNA encoding bombesin using PCR technology, DNA oligomers encoding the sense and anti-sense strands of bombesin were hybridized to create the coding region. The amino acid sequence of the bombesin peptide fused to the carboxyl end of the heavy chain of the H22 antibody is the following:

-Gln-Arg-Leu-Gly-Asn-Gln-Trp-Ala-Val-Gly-His-Leu-Met-Gly
(SEQ ID NO:5)

which corresponds to amino acids 2–14 of bombesin (Anastasi et al. (1971) *Experientia* 27:166) and contains an additional glycine residue at the carboxyl end of the peptide. The oligomers had overlapping ends that did not hybridize but instead created sticky ends for a XhoI site on the N-terminus and a NotI site on the C-terminus such that it could be cloned into the H22 heavy chain expression vector described above.

Figure 12:
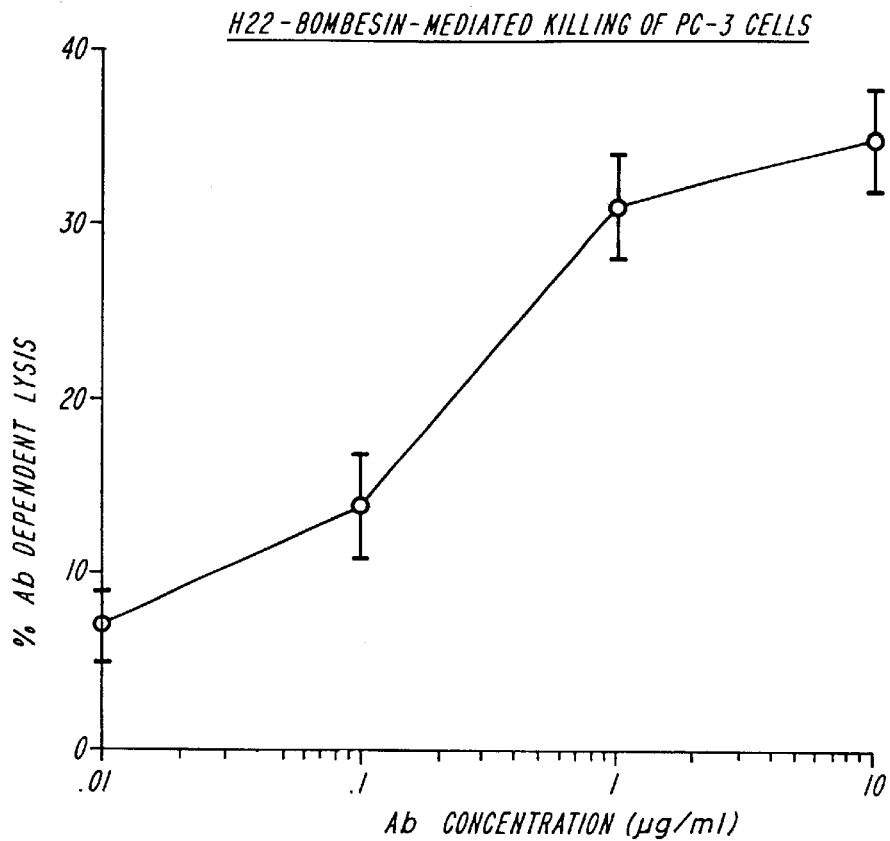
FIG. 12 is a diagram indicating the percentage of PC-3 tumor cell lysis in the presence of monocytes and in the presence of various concentrations of H22-bombesin fusion protein concentrations.

The biological activity of the H22-bombesin fusion protein on tumor cell killing was investigated as described above for the H22-EGF and H22-heregulin fusion proteins. Briefly, PC-3 tumor cells bearing bombesin receptors were labeled with $^{51}$Cr and incubated with monocytes and various concentrations of H22-fusion protein, and fusion protein dependent lysis was determined as described above. The results, shown in FIG. 12, indicate that the target cells are lysed and that the level of target cell lysis increases proportionally with the amount of fusion protein added to the assay.

Fusion proteins having H22 as one binding entity and CD4 (AIDS Repository) or gp120 (AIDS Repository) as a second binding entity were also produced.

Example 5

Production of Bispecific Antibodies From Modified Humanized Antibody Fragments

Materials and Methods

Expression Vectors and Cloning

Expression vectors for the genomic clones of the heavy (pSVgpt) and light (pSVhyg) chains of H22 were as described in International Patent Application Publication Number: WO 94/10332 entitled, HumanizedAntibodies to Fc Receptorsfor Immunoglobulin G on Human Mononuclear Phagocytes. For the Fab' construct, it was unnecessary to alter the light chain. For the heavy chain, however, the CH2 and CH3 domains had to be removed and replaced with a termination codon. The heavy chain vector contains two BamHI sites, one in the intron between VH and CH1, and the other just downstream of CH3. Using the BamHI restriction sites, DNA encoding the constant domains were replaced by a truncated version encoding only CH1 and most of the hinge. To do this, The polymerase chain reaction (PCR) was utilized to engineer the new C-terminus of the heavy chain fragment with the alterations shown in FIG. 1. FIG. 1 [B] shows the alterations for generation of a truncated single-sulfhydryl version.

Expression

The murine myeloma NSO (ECACC 85110503) is a non-Ig synthesizing line and was used for expression of the modified H22 antibody. The final expression vector, a pSVgpt construct with DNA encoding H22 Fd was cotransfected with the pSVhyg construct containing DNA encoding H22 light chain by electroporation using a BioRad Gene Pulser. These polypeptides were expressed by an Ig promoter and Ig enhancer present in the vectors, and secreted by the mAb 22 heavy chain signal peptide located on the N-terminus of the constructs. One or two days after transfection, mycophenolic acid and xanthine were added to the media to select for cells that took up the DNA. Individual growing colonies were isolated and subcloned after FcγRI binding activity was demonstrated.

Purification

The single sulfhydryl form of the H22 antibody and the whole H425 (anti-EGFR) antibody were produced by in vitro cultivation of the respective transfected NSO cells. The H425 was purified by protein A affinity chromatography. The single sulfydryl form of the antibody H22 was purified by ion exchange chromatography using Q-Sepharose followed by SP-Sepharose (Pharmacia, Piscataway, N.J.). The purity of the single sulfhydryl form of the H22 antibody was assessed by SDS-PAGE.

Generation of Bispecific Antibody BsAb)

BsAb was constructed using the method of Glernie et al. (Glennie, M. J. et al., (1987), Preparation and performance of bispecific F(ab' gamma)$^2$, antibody containing thioether-linked Fab' gamma fragments, *J. Immunol.*, 139:2367). The F(ab')$_2$ of H425 was generated by limited pepsin proteolysis in 0.1 M citrate buffer, pH 3.5 and the F(ab')$_2$ purified by ion exchange chromatography. The mAbs were reduced by addition of 20 mM mercaptoethanolamine (MEA) for 30 minutes at 30° C. The Fab' fragments were applied to a Sephadex G-25 column equilibrated in 50 mM sodium acetate, 0.5 mM EDTA, pH 5.3 (4° C.). Ortho-phenylenedimaleimide (o-PDM, 12 mM) dissolved in dimethyl formamide and chilled in a methanol/ice bath was added (one half volume) to the H22 Fab' and incubated for 30 minutes on ice. The Fab'-maleimide was then separated from free o-PDM on Sephadex G-25 equilibrated in 50 mM Na Acetate, 0.5 mM EDTA, pH 5.3 (4° C.). For preparation of the BsAbs, the H22 Fab'-maleimide was added to the H425 Fab' at a 1.2:1 molar ratio. The reactants were concentrated under nitrogen to the starting volume using a Diaflo membrane in an Amicon chamber (all at 4° C.). After 18 hours the pH was adjusted to 8.0 with 1 M Tris-HCl, pH 8.0. The mixture was then reduced with 10 mM MEA (30 minutes, 30° C.) and alkylated with 25 mM iodoacetamide. The bispecific F(ab')$_2$ was separated from unreacted Fab's and other products by a Superdex 200 (Pharmacia, Piscataway, N.J.) column equilibrated in PBS.

Bispecific Flow Cytometry

Figure 13:
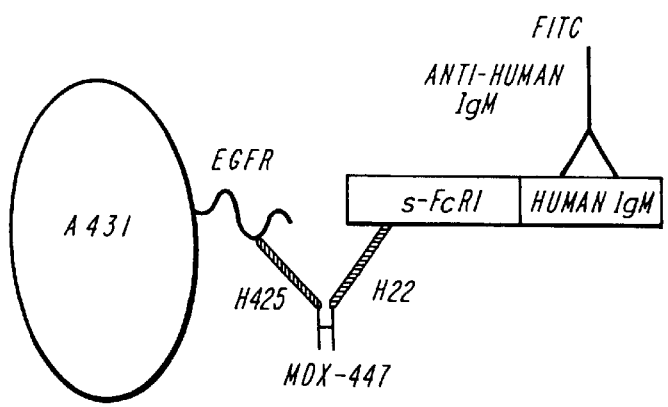
FIG. 13 is a schematic representation of the flow cytometric assay used for testing the activity of BsAb 447 generated either by the o-PDM or the DTNB method.

To show that BsAb generated by the o-PDM method as well as that generated by the DTNB method are capable of binding both FcγRI and EGFR simultaneously, a flow cytometric assay has been developed (FIG. 13). In this assay different concentrations of the two BsAbs were incubated with A431 cells, a cell line which expresses the EGF receptor (EGFR). After washing, a supernatant containing a fusion protein consisting of the extracellular domain of FcγRI and the Fc portion of human IgM was incubated with the cells. Finally, the cells were incubated with a FITC-labeled anti-human IgM-specific antibody. The cells were then analyzed by FACSCAN.

ADCC

BsAb-mediated ADCC was determined using a $^{51}$Cr killing assay. The EGFR overexpressing cell line, A431, was used as targets for lysis by human monocytes cultured in γ-interferon for 24 hours. Targets were labeled with 100 μCi of $^{51}$Cr for 1 hour prior to combining with effector cells and antibody in a flat-bottomed microtier plate. After incubation for 16 hours at 37° C. supernatants were collected and analyzed for radioactivity. Cytotoxicity was calculated by the formula: % lysis=(experimental CPM−target leak CPM/ detergent lysis CPM−target leak CPM)×100%. Ab-dependent lysis=% lysis with antibody−% lysis without antibody.

Results

Purification

NSO cells were cotransfected with the truncated H22 heavy chain construct and the intact kappa chain construct. Clones selected for resistance to mycophenolic acid and xanthine were expanded and the protein was purified from the supernatant by Q-Sepharose followed by SP-Sepharose ion exchange chromatography. The purified protein was analyzed by SDS-PAGE. The purified protein migrated at an apparent molecular weight of 50 kDa, indicating that the protein is expressed as a monomer, not a disulfide-linked dimer.

Construction and characterization of a BsAb Composed of Single Sulfhydryl H22 Linked to Fab' of H425 (anti-EGFR)

Figure 14:
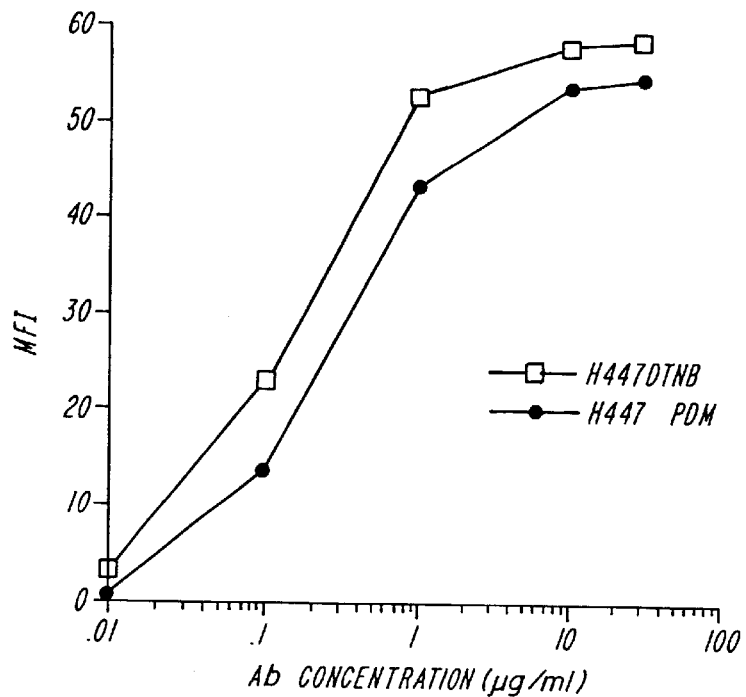
FIG. 14 is a graph, which plots the MFI of various concentrations of o-PDM and DTNB derived BsAb 447 to EGFR and FcγRI expressing A431 cells.

A BsAb was constructed where the single sulfhydryl form of H22 was linked to the Fab' fragment of H425, a humanized anti-EGFR mAb. The BsAb was generated using o-PDM as a linker by the method of Glennie et al. (Glennie, M. J. et al., (1987), Preparation and performance of bispecific F(ab' gamma)$^2$, antibody containing thioether-linked Fab' gamma fragments, *J. Immunol.*, 139:2367). The activity of this BsAb was compared to one generated by the DTNB method using Fab' fragments made from pepsin digestion and reduction of whole H22. To demonstrate that these BsAbs could bind FcγRI and EGFR simultaneously a bispecific FACS assay was devised. FIG. 14 shows that both the o-PDM-linked BsAb and the BsAb made by the DTNB method bound EGFR on A431 cells and soluble FcγRI simultaneously in a dose-dependent fashion.

Figure 15:
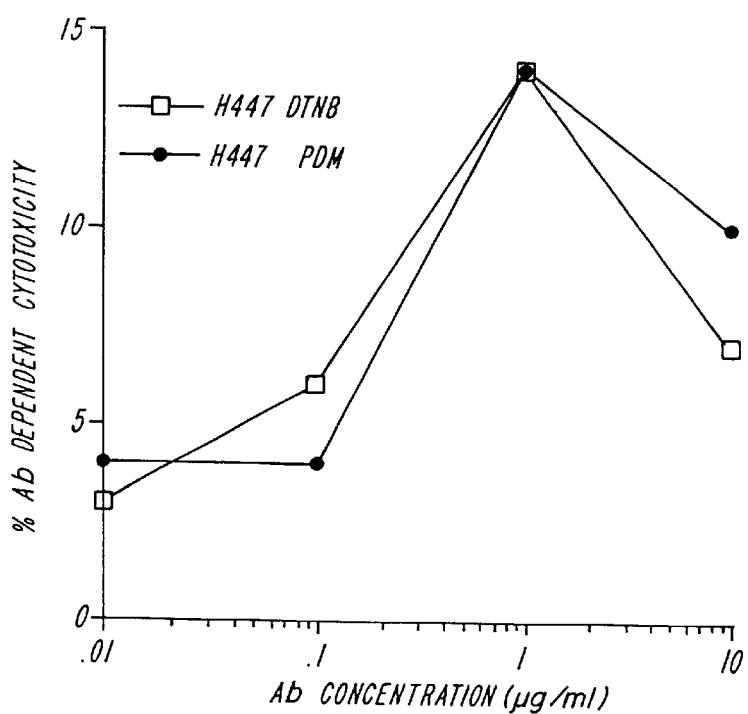
FIG. 15 is a graph, which plots the antibody dependent cytotoxicity resulting from the binding of o-PDM and DTNB derived BsAb 447 to A431 cells.

The ability of the two BsAbs to mediate ADCC was analyzed using A431 cells as targets. Human monocytes cultured for 24 hours in the presence of IFN-γ were used as effector cells. FIG. 15 demonstrates the two BsAbs mediated dose-dependent lysis of A431 cells in a comparable fashion. These results demonstrated that BsAb generated from the truncated, single sulfhydryl form of H22 was capable of killing EGFR-overexpressing cells in the presence of FcγRI-expressing effector cells.

Example 6

Production of Trivalent Antibodies

Materials and Methods

Cell Lines and Antibodies. M22, 520C9, H425. SKBR3 and A431

M22 and 520C9 were purified from hybridoma supernatant by ion exchange chromatography (Pharmacia, Piscataway, N.J.) and 520C9 was further purified by protein A affinity chromatography (Pharmacia, Piscataway, N.J.). H425 was purified from hybridoma supernatant by protein A affinity chromatography (Pharmacia, Piscataway, N.J.). The M22-and 520C9- producing murine hybridoma were described previously (Guyre et al., (1989) Monoclonal antibodies that bind to distinct epitopes on FcgRI are able to trigger receptor function, *J. Immunol.* 143:5, 1650–1655; Frankel et al., (1985) Tissue distribution of breast cancer-associated antigens defined by monoclonal antibodies, *J. Biol. Response Modifiers,* 4:273–286). The murine myeloma NS0 (ECACC 85110503) is a non-Ig synthesizing line and was used for the expression of the humanized mAb, H425 (Kettleborough et al., (1991) Humanization of a mouse monoclonal antibody by CDR-grafting: the importance of framework residues on loop conformation, *Protein Eng.,* 4:773). SKBR-3, (ATCC, Rockville, Md.) a human breast carcinoma cell line that overexpresses the HER2/neu protooncogene, and A431 (ATCC, Rockville, Md.), a human squamous carcinoma cell line that overexpresses EGFR (ATCC, Rockville, Md.) were cultivated in Iscove's Modified Dulbecco's Medium (IMDM, Gibco, Grand Island, N.Y.).

Neutrophil Preparation

Neutrophils are separated from mononuclear cells by ficoll hypaque (Pharmacia, Piscataway, N.J.) gradient separation. To up-regulate FcγRI, neutrophils are treated with cytokines. Neutrophils are cultured for 24–48hrs (37° C., 5% $CO_2$) in AIM V media (Gibco, Grand Island, N.Y.) containing 2.5% normal human serum type AB (Sigma, St. Louis, Mo.), 50 ng/ml G-CSF (Kindly provided br R. Repp, U. of Erlanger, Germany) and 100 IRU/ml IFN-γ.

Conjugation Method

BsAb were constructed using the method of Glennie et al (Glennie, M. J. et al., (1987), Preparation and performance of bispecific F(ab' gamma)$^2$, antibody containing thioether-linked Fab' gamma fragments, *J. Immunol.,* 139:2367). mAbs M22, 520C9 (anti-HER2/neu, 33), and H425 (anti-EGFR) antibodies were produced by in vitro cultivation of the respective hybridoma cells. The F(ab')$_2$ of each antibody were generated by limited pepsin proteolysis in 0.1 M citrate buffer, pH 3.5 and the F(ab')$_2$ purified by ion exchange chromatography. mAbs M22 and H425 were reduced to Fab' by addition of 20 mM mercaptoethanolamine (MEA) for 30 minutes at 30° C. The Fab' fragments were applied to a Sephadex G-25 column equilibrated in 5OmM Na Acetate, 0.5 mM EDTA, pH 5.3 (4° C.). Ortho-phenylenedimaleimide (o-PDM, 12 mM) dissolved in dimethyl formamide and chilled in a methanol/ice bath was added (one half volume) to the murine 22 Fab' and incubated for 30 minutes on ice. The Fab'-maleimide was then separated from free o-PDM on Sephadex G-25 equilibrated in 50 mM Na Acetate, 0.5 mM EDTA, pH 5.3 (4° C.). For preparation of the BsAbs, the M22 Fab'-maleimide was added to the H425 Fab' at a 1:1 molar ratio. The reactants were concentrated under nitrogen to the starting volume using a Diaflo membrane in an Amicon chamber (all at 4° C.). After 18 hours the pH was adjusted to 8.0 with 1M Tris-HCl, pH 8.0. The mixture was then reduced with 10 mM MEA (30 minutes, 30° C.) and alkylated with 25 mM iodoacetamide. The bispecific F(ab')$_2$ as separated from unreacted Fab's and other products by a Superdex 200 (Pharmacia, Piscataway, N.J.) column equilibrated in phosphate buffered saline (PBS). The BsAb M22×520C9 was made in a similar fashion except that 520C9 was used instead of H425.

Figure 16A:
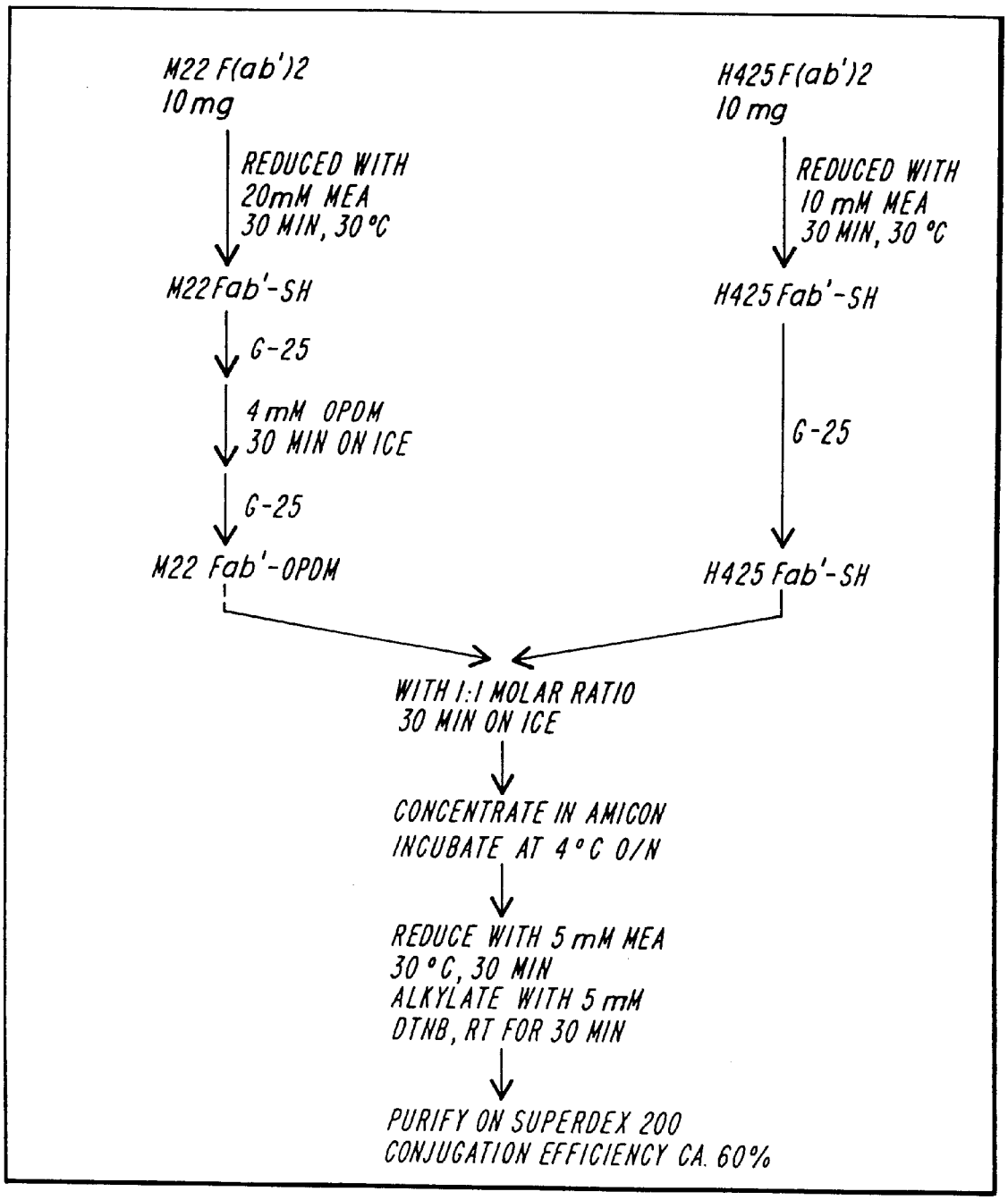
FIGS. 16(A–B) is a flow chart that depicts the construction of trispecific antibodies.
Figure 16B:
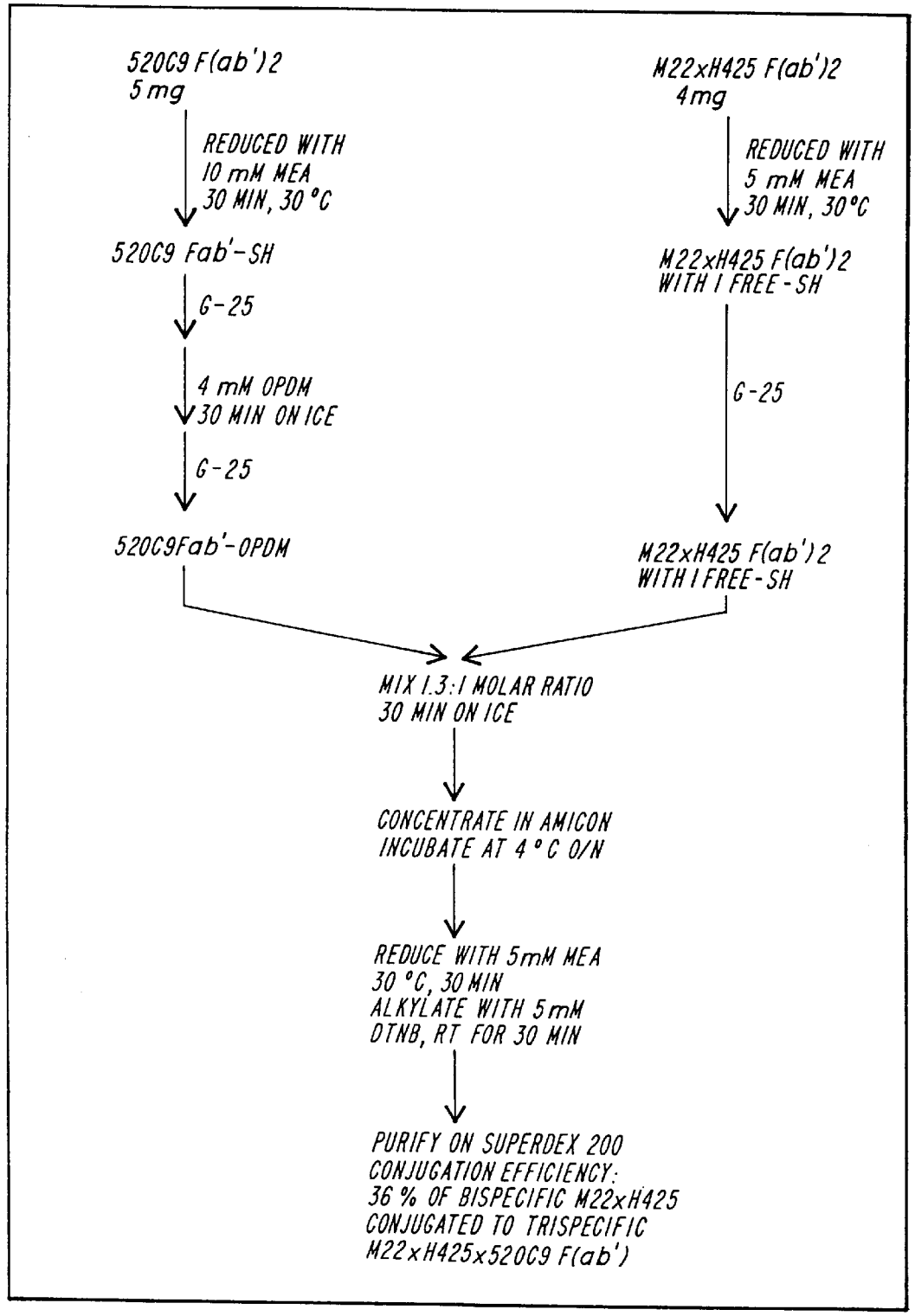

Trispecific antibody composed of M22×H425×520C9 was made in two stages (FIG. 16). In the first stage, M22 was linked to H425 as described above to create the M22×H425 BsAb except that rather than a final reduction and alkylation, the reactants were treated with DTNB to block the remaining free sulfhydryl groups. The bivalent BsAb was purified by gel filtration on a Superdex 200 column, reduced to F(ab')$_2$(SH) and mixed in a 1:1 molar ratio with o-PDM-treated 520C9. The resulting trispecific F(ab)3 was purified on a Superdex 200 column. The TsAb was analyzed by HPLC size exclusion chromatography using a TSK 3000 column (ToJo Haas, Japan). Using the same procedure as above another TsAb comprising m22 Fab'×32.2 Fab'×m22 Fab' has been constructed.

Bispecific Flow Cytometry

The TsAb can bind to EGFR and F$_{c\gamma}$RI simultaneously or to HER2/neu and F$_{c\gamma}$RI simultaneously. Either A431 cells (high EGFR-expressing cells) or SKBR-3 cells (high HER2/neu-expressing cells) were incubated with various concentrations of BsAbs (M22×520C9 or M22×H425) or with the TsAb, M22×H425×520C9. The cells were washed and then incubated with the soluble F$_{c\gamma}$RI. Soluble F$_{c\gamma}$RI binding was detected with mAb 32.2-FITC which binds F$_{c\gamma}$RI at a site that is distinct from the 22 binding site. The cells were then analyzed by FACSCAN.

ADCC

Either SKBR-3 cells or A431 cells were used as targets for lysis by cytokine activated neutrophils. Targets were labeled with 100 μCi of $^{51}$Cr for 1 hour prior to combining with neutrophils and antibodies in a U-bottom microtiter plate. After incubation for 16 hours at 37° C. supernatants were collected and analyzed for radioactivity. Cytotoxicity was calculated by the formula: % lysis=(experimental CPM−target leak CPM/detergent lysis CPM−target leak CPM)× 100%. Specific lysis=% lysis with antibody−% lysis without antibody. Assays were performed in triplicate.

FcγRI Modulation Assay

Figure 23A:
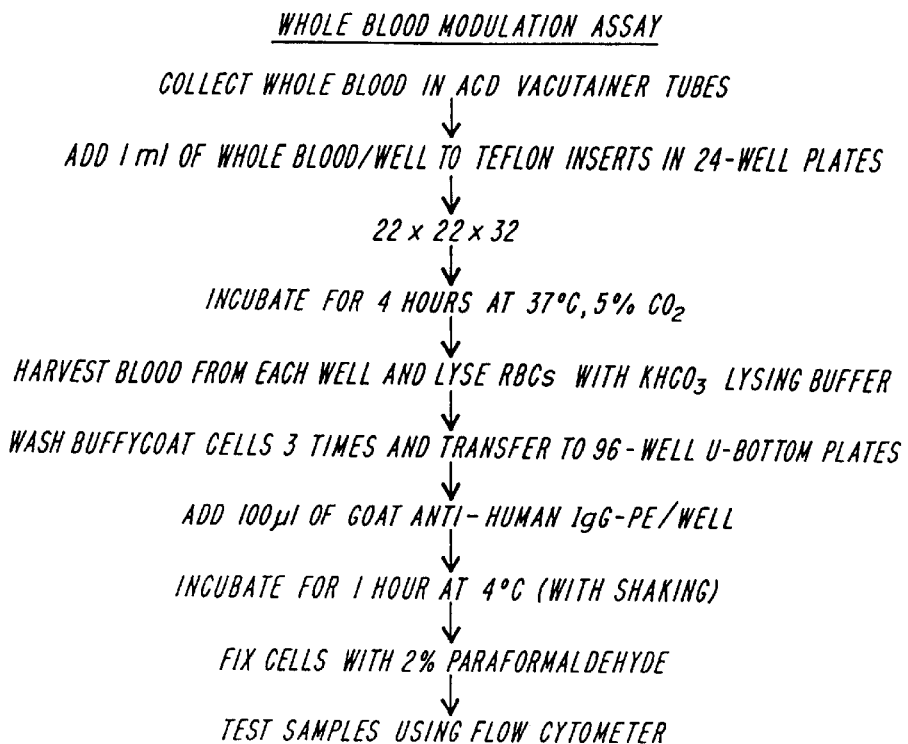
FIG. 23 is a flow chart for a whole blood modulation assay (panel A) and the results from the assay (panel B). This trivalent antibody rapidly modulates FcγRI from the surface of monocytes.
Figure 23B:
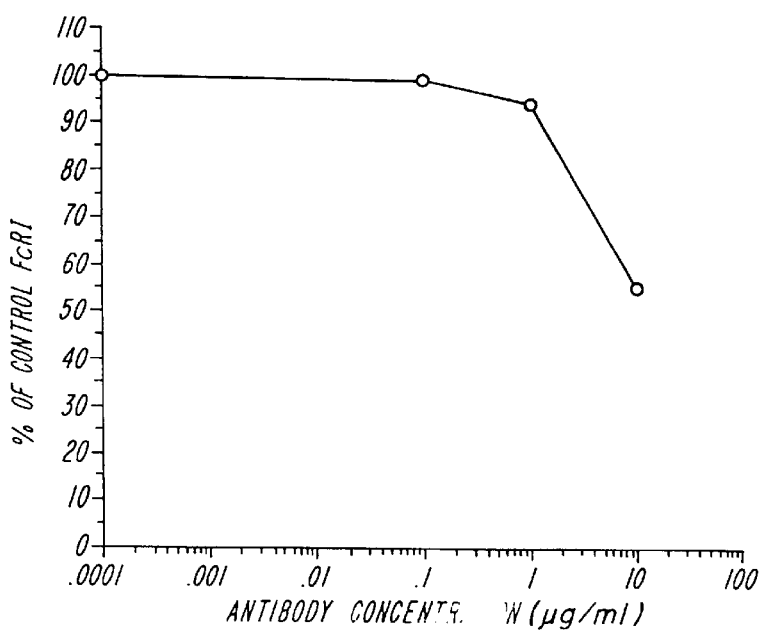
Figure 25A:
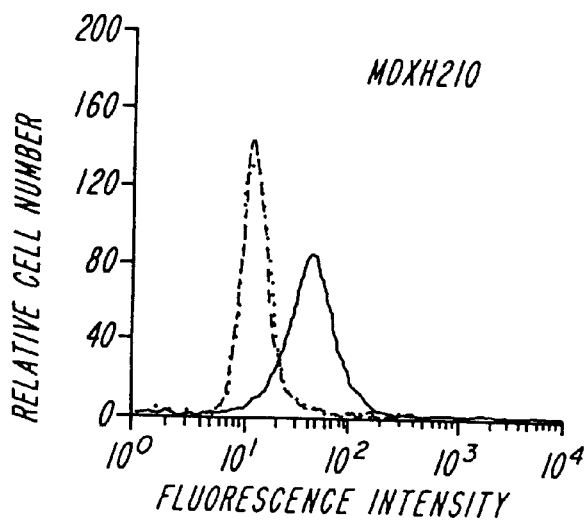
FIG. 25 panels A, B, and C represent flow cytometry analysis results showing binding of MDXH210, Fab22-TT830, and H22-TT833S to FcγRI positive U937 cells, respectively. The dashed lines represent negative controls, the solid lines denote staining with the fusion proteins, and the dotted lines respresent fusion protein binding blocked by murine mAb 22 F(ab')₂.
Figure 25B:
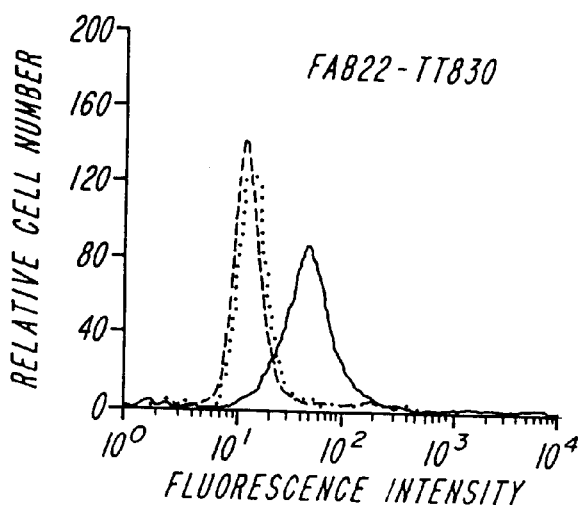
Figure 25C:
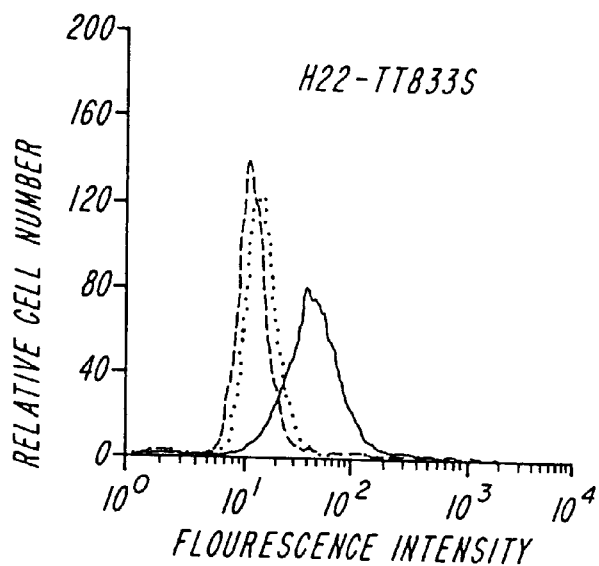

The M22×32.2×M22 BsAb was used for modulation of FcγRI on monocytes in whole blood. The assay procedure is shown in the enclosed flow chart (see FIG. 23A). FIG. 23B shows that treatment with 10 μg/mL of this BsAb decreased the FcγRI expression on monocytes to approximately 50% of the level prior to BsAb treatment.

Results

Construction and Biochemical Characterization of the TsAb

Figure 17:
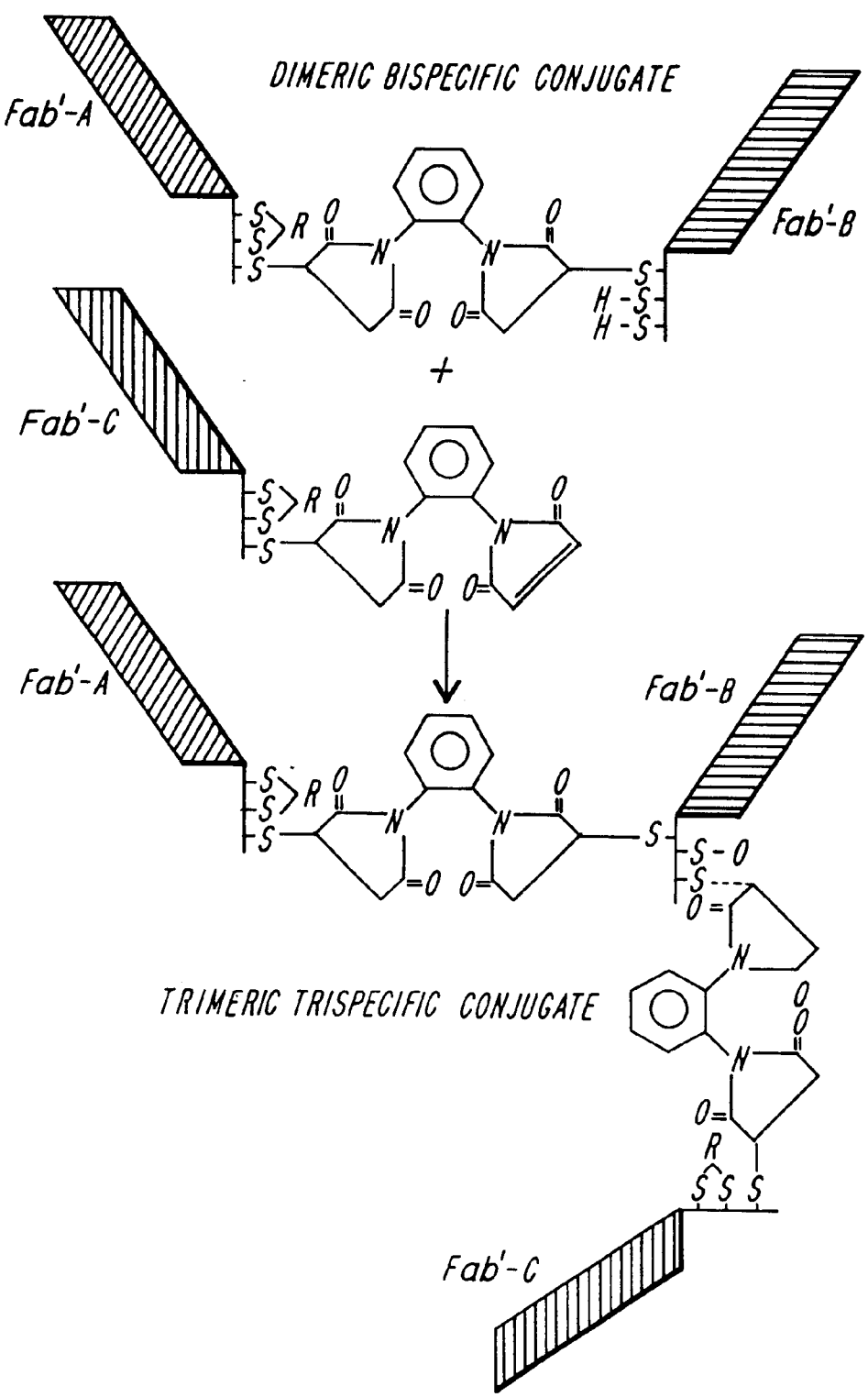
FIG. 17 depicts the transformation of a bivalent, bispecific antibody into a trivalent, bispecific antibody. The bivalent, bispecific conjugate is reduced and mixed with o-PDM-treated 520C9 Fab' resulting in the TsAb.

TsAb was made according to the flow chart depicted in FIG. 16. In the first stage of the procedure, M22 was coupled to H425, treated with DTNB, and the resulting bispecific F(ab')$_2$ purified by gel filtration. In the second stage, this bispecific F(ab')$_2$ was reduced and mixed with o-PDM-treated 520C9 Fab' resulting in the TsAb, M22×H425× 520C9. This TsAb is depicted schematically in FIG. 17. In this figure, Fab'-A represents M22, Fab'-B represents H425, and Fab'-C represents 520C9.

Binding (Bs FACS)

Figure 18A:
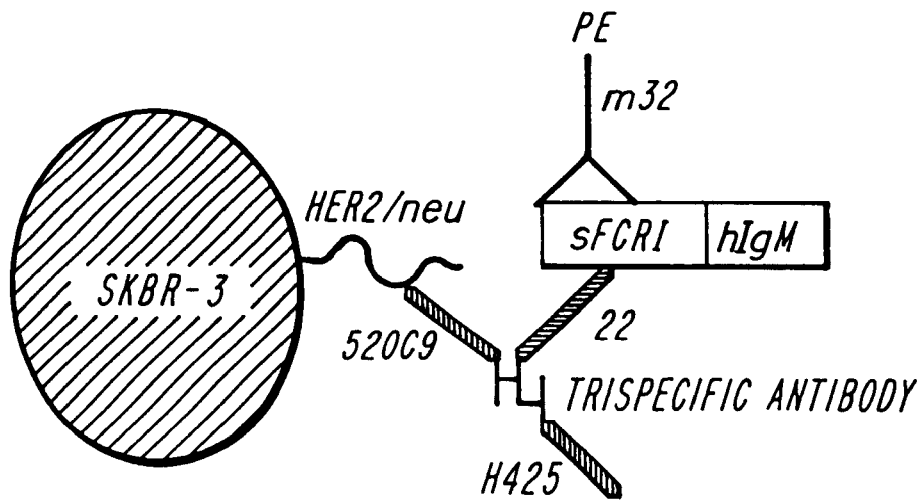
FIG. 18 depicts a bifunctional fluorescence-activated cell sorting assay for HER2/neu (panel A) and EGFR (panel B).
Figure 18B:
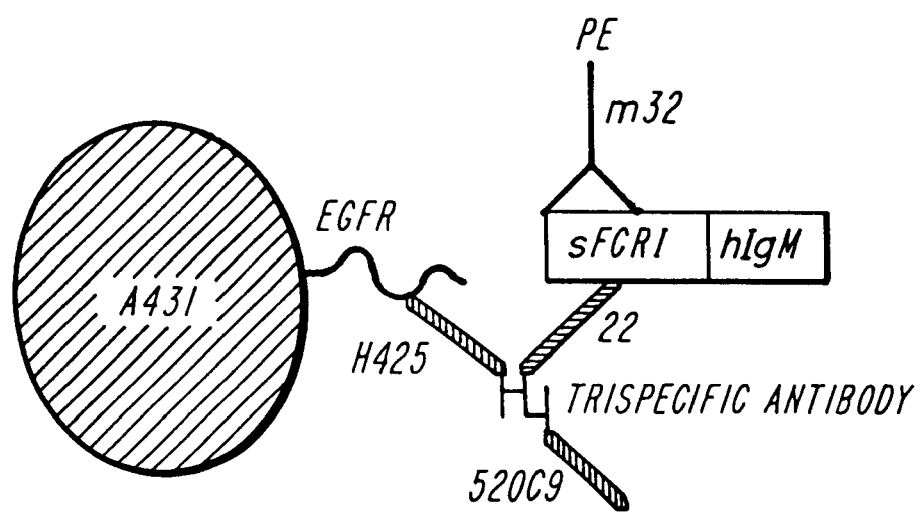
Figure 19:
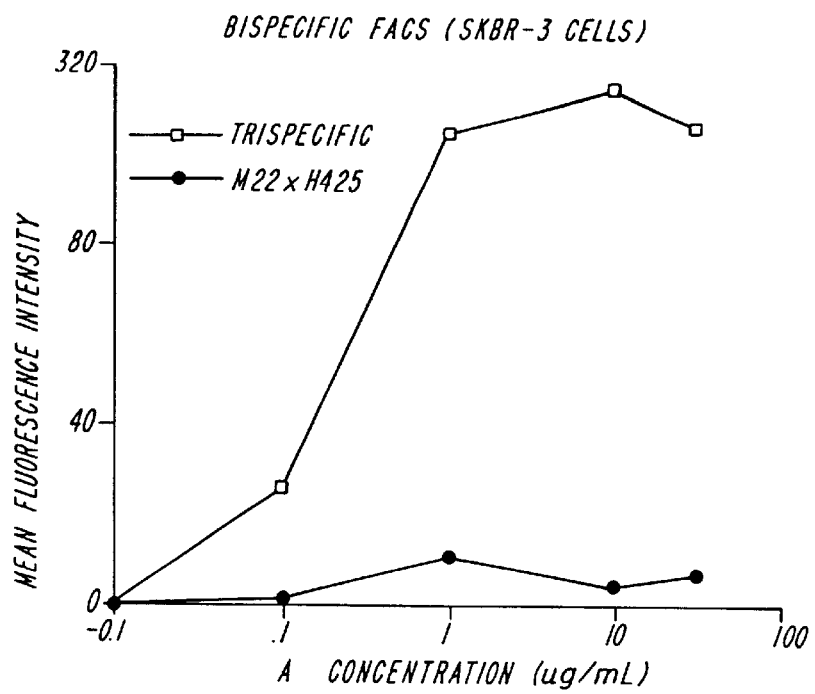
FIG. 19 is a graph which plots the binding of various concentrations of antibody, either BsAb or TsAb, to target cells. Mean Fluorescence Intensity (MFI) increases as Ab binding increases. It shows that the TsAb bound both HER2/neu on SKBr-3 cells and soluble FcγRI simultaneously in a dose-dependent fashion.
Figure 20:
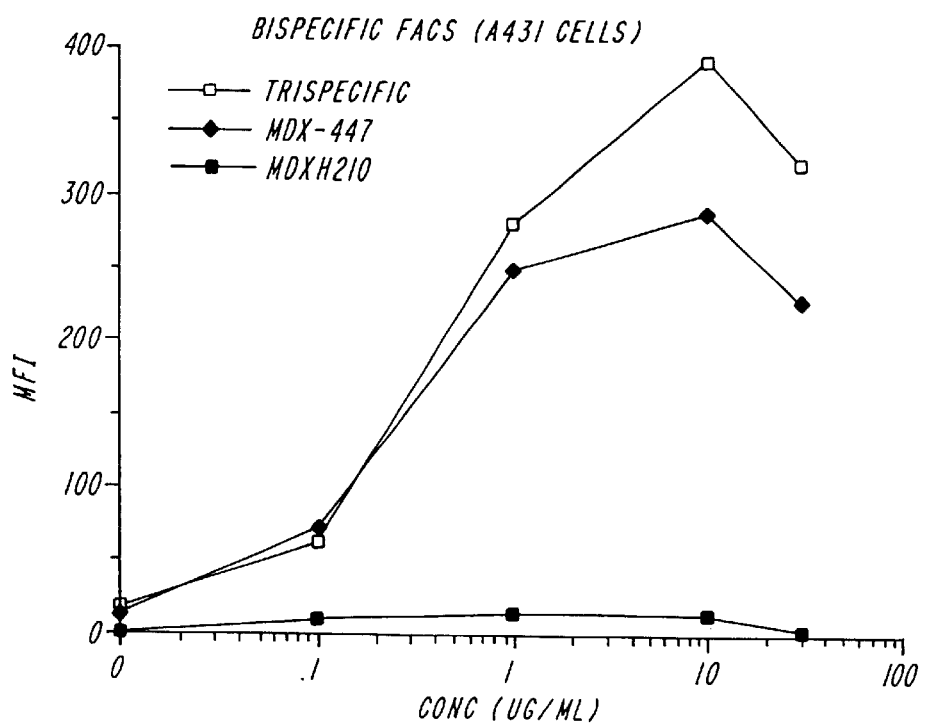
FIG. 20 is a graph that shows the TsAb bound both EGFR on A431 cells and soluble FcγRI simultaneously in a dose-dependent fashion. The assay is similar to that used in FIG. 19.

To demonstrate that the TsAb, M22×H425×520C9, could bind FcγRI and HER2/neu simultaneously a bispecific FACS assay was devised. This assay is depicted schematically in FIG. 18A. FIG. 19 shows that both the TsAb bound HER2/neu on SKBR-3 cells and soluble FcγRI simultaneously in a dose-dependent fashion. The BsAb, M22× H425, generated negligible signal in this assay over a wide range of concentrations. To demonstrate that the TsAb, M22×H425×520C9, could bind FcγRI and EGFR simultaneously a similar assay was devised using the EGFR-overexpressing cell line, A43 1, in the case. This assay is depicted schematically in FIG. 18B. FIG. 20 shows that both the TsAb and the BsAb, M22×H425, bound EGFR on A431 cells and soluble FcγRI simultaneously in a dose-dependent fashion. The BsAb, M22×520C9, generated negligible signal in this assay over a wide range of concentrations.

ADCC

Figure 21:
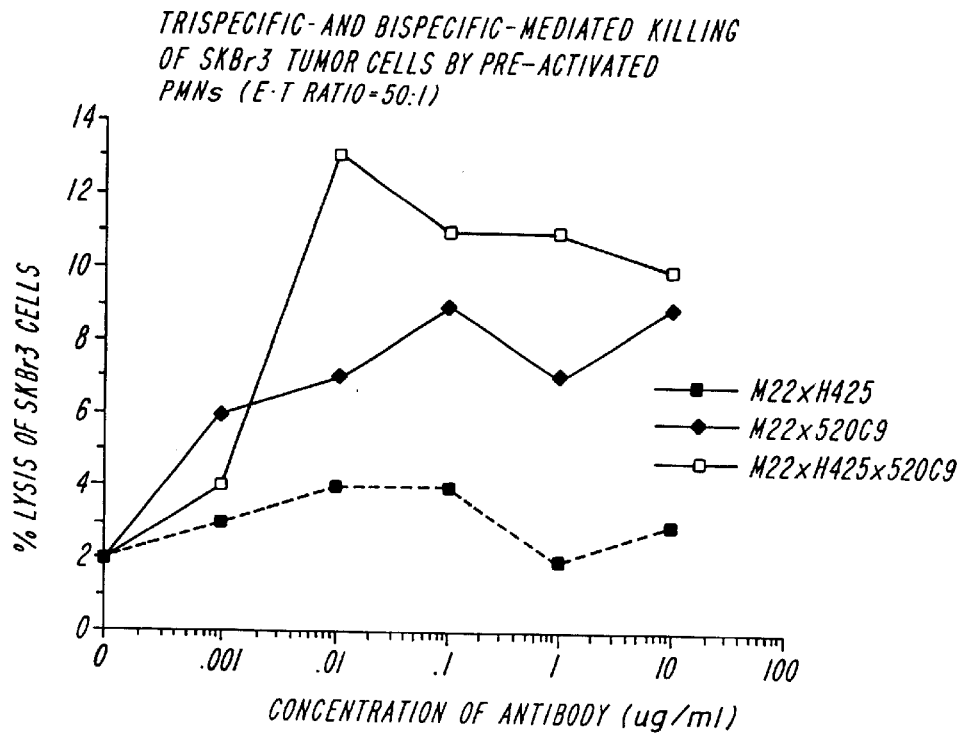
FIG. 21 is a graph that shows the TsAb, M22×H425×520C9, and the BsAb, M22×520C9 were capable of inducing ADCC of SKBR-3 cells but the BsAb, M22×H425, was not. Various concentrations of antibodies were incubated with SKBR-3 cells and pre-activated PMNs.
Figure 22:
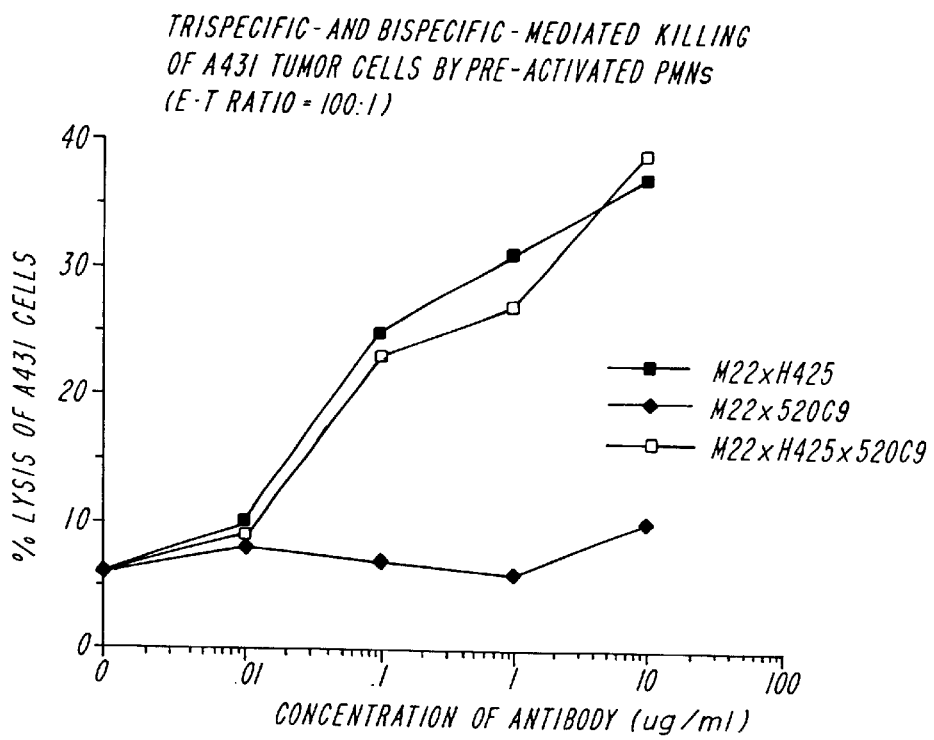
FIG. 22 is a graph that shows the TsAb, M22×H425×520C9, and the BsAb, M22×H425 were capable of inducing ADCC of A431 cells but the BsAb, M22×520C9, was not. The assay was performed in a similar manner as the assay in FIG. 21.

The ability of the TsAb to mediate ADCC was analyzed using either SKBR-3 or A431 cells as targets. Human neutrophils cultured for 24–48 hours in the presence of IFN-γ and G-SF were used as effector cells. FIG. 21 demonstrates the both the BsAb, M22×520C9, and the TsAb, M22×H425×520C9, mediated lysis of SKBR-3 cells, whereas the BsAb, M22×H425, did not. On the other hand, FIG. 22 demonstrates the BsAb, M22×H425, and the TsAb, mediated lysis of SKBR-3 cells, whereas the BsAb, M22× 520C9, did not. These results demonstrated that the TsAb was capable of killing both HER2/neu and EGFR-overexpressing cells in the presence of F$_{c\gamma}$RI-expressing effector cells.

The trispecific antibody described above included M22, the murine version of the anti-FcγRI mAb. Such a trispecific antibody could be constructed using the single-sulfhydryl form of the humanized anti-FcγRI mAb, H22. The only difference being that single-sulfhydryl form is secreted as a F(ab')$_2$ fragment of this antibody. The single-sulfhydryl form is purified from culture supernatants utilizing ion exchange chromatography using Q-Sepharose followed by SP-Sepharose (Pharmacia, Piscataway, N.J.). Once the single-sulfhydryl form of H22 is purified, the creation of a trispecific antibody using this reagent would be identical to that described above using the F(ab')$_2$ fragment of M22.

Example 7

Enhanced Antigen Presentation with H22-antigen Fusion Proteins

This example demonstrates that (a) antigenic peptides genetically grafted onto the constant region of an anti-FcγRI antibody are significantly more efficient in antigen presentation of the antigen and T cell stimulation compared to the antigen alone, and (b) that antagonistic peptides genetically grafted onto the constant region of an anti-FcγRI are significantly more efficient in inhibiting T cell stimulation compared to the antagonistic peptide alone. Thus, such fusion proteins will effectively increase the delivery of peptides to antigen presenting cells (APCs) in vivo and will be useful in various therapeutic methods.

Materials and Methods

Reagents

AIM V (GIBCO, Grand Island, N.Y.) was used as culture medium. Tetanus. Toxoid (TT) was purchased from ACCU-RACTE CHEMICAL CO. (Westbury, N.Y.). Sterile and low-endotoxin F(ab')$_2$ fragment of mouse anti-FcγRI mAb 22 and the bispecific Ab, MDXH210 (consisting of Fab' of humanized Ab 22 chemically linked to Fab' of anti-Her2/neu tumor Ag mAb 520C9) were provided by MEDAREX, INC. (Annandale, N.J.). The universal Th epitope of TT, TT830-

844 (QYIKANSKFIGITEL (SEQ ID NO:6), termed as TT830 hereafter) (Valmori D. et al. (1994) *J. Immunol.* 152:2921–29) and the mutant form of this epitope, TT833S (QYISANSKFIGITEL (SEQ ID NO:9), lysine at position 833 changed into serine) were synthesized and purified to >95% by PEPTIDOGENIC CO. (Livermore, Calif.). Another universal Th epitope of TT, TT947-967 (FNNFTVSF WLRVPKVSASHLE (SEQ ID NO:12), referred to as TT947 hereafter), (>80% pure) (Valmori D. supra) was used as a control peptide in this study. Commercially available human IgG for intravenous injection (IVI) was used in blocking experiments.

Cells

The monocytic cell line, U937, which expresses Fc$\gamma$RI, was obtained from the ATCC. The method of generating CD4$^+$, peptide TT830-specific T cells was modified from a previously described protocol for TT-specific T cell lines (Gosselin E. J. (1992) *J. Immunol.* 149:3477–81). Briefly, mononuclear cells were isolated from peripheral blood using Ficoll Hypaque. 150×10$^6$ mononuclear cells were stimulated in 50 ml of AIM V medium with 10 $\mu$M TT830. After three days' incubation at 37° C. in a 5% CO$_2$ incubator, non-attached (mostly non-specific cells) were removed by washing the flask 1X with 10 ml of HEPES-buffered RPMI 1640; specific T cell colonies together with adherent monocytes remained in the flask. Fifty ml of AIM V plus 20 U/ml of human IL-2 (IMMUNEX, Seattle Wash.), and 1 ml (2%, final concentration) pooled human serum were added back to the flask. After 10–14 days of total incubation time, T cells were harvested and dead cells were pelleted through Ficoll Hypaque, yielding a highly enriched population (95–98%) of viable CD4$^+$, Ag-specific T cells. The T cells were confirmed to be specific for TT830 peptide as shown in FIG. 3. Large quantities of monocytes were purified from leukophoresis packs using the cold aggregation method (Mentzer S. J. et al. (1986) *Cell. Immunol.* 101:132) which resulted in 80–90% purity. Both monocytes and T cells were frozen in aliquots for future use and were shown to function normally after being thawed.

Ag Presentation Assay

In proliferation assays, T cells (5×10$^4$), irradiated monocytes (3000 rad, 10$^5$/well), and various concentrations of peptide TT830 fusion protein Fab22-TT830 were incubated together in a final volume of 200 $\mu$l/well in flat-bottom 96-well tissue culture plates for 2 days. 10 $\mu$l (1 $\mu$Ci/well) $^3$H-thymidine was then added to each well. After incubating overnight, plates were harvested and counted in a liquid scintillation counter. T cell proliferation was expressed as the mean counts/min (CPM) of three replicates±SD. Background CPM (T cells and monocytes without Ag) was subtracted from all the data points. Experiments with APL were done according to similar protocols reported by Sette et al. (De Magistris (1992) *Cell* 68:625). Briefly, for inhibition assays, irradiated monocytes were treated with various concentrations of TT 833S or Fab22-TT833S overnight. 20 nM TT830 and T cells were then added. After a further 2 days incubation, T cell proliferation was measured as described above. In "pre-pulsing" experiments, irradiated monocytes were pulsed with 20 nM TT830 4 h prior to the addition of 10 $\mu$M TT 833S or 0.$\mu$M Fab22-TT833S. After overnight incubation, T cells were then added. After a further 2 days incubation, T cells were stimulated with irradiated monocytes and TT833S or Fab22-TT833S for 1 day, recovered after centrifugation over Ficoll Hypaque, and restimulated with monocytes and various concentrations of TT830 for 2 days. T cell proliferation was then measured by the incorporation of $^3$H-thymidine and the average CPM of three replicates was plotted. In some cases, the percentage of inhibition was calculated by the formula: % inhibition= (CPM$_{no\ inhibitor}$-CPM$_{inhibitor}$)/CPM$_{no\ inhibitor}$33 100. All experiments were repeated at least three times.

Staining and Flow Cytometry

Staining procedures were adapted from those previously described (Gosselin E. J. et al. (1990) *J. Immunol.* 144–1817–22). Briefly, to individual wells of a 96-well plate at 4° C., 30 $\mu$l of RPMI+1 mg/ml BSA containing one of the proteins Fab22-TT830, Fab22-TT833S, or the BsAb MDXH210 at varying concentrations. After 1 h incubation at 4° C., plates were centrifuged, the supernatants discarded, and the cells washed three times with PBS/BSA at 4° C. Cells were then incubated for 1 h with 40 $\mu$l /well of FITC-labeled F(ab')$_2$ goat anti-human IgG (JACKSON IMMUNORESEARCH LABORATORIES, INC. West Grove, Pa.) followed by three washes with PBS/BSA and resuspended in PBS/BSA containing 1% paraformaldehyde (KODAK, Rochester, N.Y.). Cells were then examined by FACScan (BECTON DICKINSON & CO., Mountain View, Calif.), and mean fluorescence intensity (MFI) was measured.

Cytokine Measurement

Supernatants were collected from the 96-well plates of Ag presentation assays after 2 days stimulation and frozen until used. The levels of IFN-$\gamma$ and IL-4 from these samples were measured by specific ELISA. Ab pairs for the IFN-$\gamma$ and IL-4-specific ELISA were purchased from PHARMINGEN (San Diego, Calif.). ELISA assays were performed according to the protocol provided by the manufacturer.

Generation of H22- TT Peptide Fusion Proteins

In order to generate fusion proteins Fab22-TT830 and Fab22-TT833S, synthetic oligonucleotides encoding each peptide were separately engineered into the hinge region in the heavy chain of humanized anti-Fc$\gamma$RI mAb 22 (H22) according to the method set forth below.

Expression and Cloning Vectors mAb 22 has been humanized by grafting its CDR regions into a human IgG1 framework (see above and Graziano R. F. et al. (1995) *J. Immunol.* 155:4996–5002). The expression vector for the genomic clone of the heavy chain (pSVgpt) of H22 was modified to allow incorporation of the coding sequence for other molecules, in this case, the TT peptides. The BamHI fragment of this vector containing CH1, hinge, and newly engineered XhoI and NotI cloning sites (see FIG. 2) was inserted into the BamHI site of pUC 19 to generate the vector pUC19/H22CH1(X+N). This vector was used to clone oligonucleotide sequences encoding TT peptides, as described below.

The oligonucleotide sequences encoding the tetanus toxin (TT) peptides were designed to have a XhoI site on the N-terminus and a NotI site on the C-terminus of the coding region (FIG. 24A). These oligonucleotides were synthesized and purified by GENOSYS Biotechnologies (The Woodlands, Tex.). The synthetic oligonucleotides were then annealed and ligated into the cloning vector pUC19/ H22CH1(X+N). Clones which had incorporated the coding sequences for TT peptides were screened by restriction mapping. The BamHI fragment containing CH1, hinge, and TT830 or TT833S was then cut out of pUC 19 and inserted into the expression vector which already contained VH. The final expression construct of H22 heavy chain fused with TT peptides is shown in FIG. 24B.

Expression of the H22- TT Fusion Proteins

The murine myeloma NSO (ECACC 85110503) is a non-Ig synthesizing line and was used for expression of the H22-TT fusion proteins. First, NSO cells were transfected with the pSVhyg vector containing the H22 light chain coding sequence. The H22 light chain expressing NSO cells were then transfected with the expression vector construct containing the H22 H-chain Fd sequence fused in frame to the TT coding sequences (FIG. 24B). A BioRad Gene Pulser electroporation apparatus was used to carry out the transfection employing 200 v and 960 $\mu$Farad. One or two days after transfection, mycophenolic acid (0.8 $\mu$g/ml; SIGMA) and xanthine (2.5 $\mu$g/ml; SIGMA) were added to the media to select transfectants which had successfully taken up the expression vectors. Individual colonies were isolated based on the binding activity of the culture supernatants to Fc$\gamma$RI on U937 cells as demonstrated by flow cytometry. The positive colonies were subcloned by limiting dilution.

Purification of the Fab22-TT Fusion Proteins

Clone pW5 expressing the Fab22-TT830 fusion protein and clone pM4 expressing the Fab22-TT833S fusion protein were expanded in roller bottle cultures. The supernatants were clarified and concentrated. Small scale purification was performed by affinity chromatography on an anti-H22 affinity column. SDS-PAGE analysis of a 5–10% acrylamide gradient gel under non-reducing conditions showed that fusion proteins were >90% pure and had a molecular weight of 50 kDa as expected. Protein concentration was determined by absorbance at 280 nm using the extinction coefficient of IgG Fab'=1.53.

Results

H22Fd-TT Fusion Proteins Bind to U937 Cells

The ability of the H22 fusion proteins, Fab22-TT830 and Fab22-TT833S, to bind to Fc$\gamma$RI was examined first. A previously described bispecific Ab, MDXH210, which contains the same Fc$\gamma$RI-binding component (Fab' of humanized mAb 22) (Valone F. H. et al. (1995) *J. Clin. Oncol.* 13:2281–92), was used as a positive control. Binding of fusion proteins and MDXH210 to U937 cells, which constitutively express Fc$\gamma$RI, was measured by staining with FITC-labeled goat Ab specific for human IgG and flow cytometry. As indicated in FIGS. 24A and 24B, fusion proteins Fab22-TT830 and Fab22-TT833S bound to U937 cells in a dose-dependent manner similar to MDXH210. The binding of fusion proteins was completely blocked by murine anti-human Fc$\gamma$RI mAb 22 F(ab')$_2$, demonstrating the specificity of fusion proteins for Fc$\gamma$RI.

H22Fd-TT Fusion Protein Enhances Presentation of TT Peptide by 100–1000 Fold.

Figure 26:
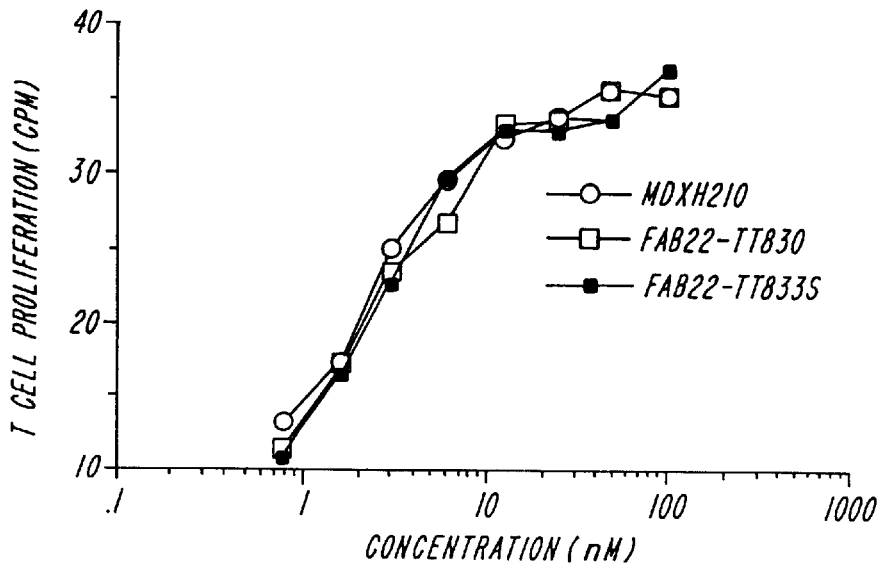
FIG. 26 is a schematic diagram showing the mean fluorescence intensity resulting from incubation of various amounts of the fusion proteins MDXH210, FAb22-TT830, and Fab22-TT833S to FcγRI positive U937 cells.

The fusion protein, Fab22-TT830 was used in Ag presentation assays to determine whether the Th epitope, TT830, when expressed in the constant region of H22, could be effectively presented by monocytes to autologous T cells. As shown in FIG. 26, about 1,000-fold less Fab22-TT830 was required than TT830 peptide alone to achieve the same level of T cell proliferation. In addition, FIG. 26 shows that the presentation of Fab22-TT830 was about 10,000-fold more efficient than the presentation of the intact TT, suggesting that the enhanced presentation of Fab22-TT830 did not merely result from higher molecular weight nor increased stability of Fab22-TT830 as opposed to TT830 peptide. Another antigenic TT epitope, TT947, failed to stimulate the T cells, confirming that the T cells were specific for TT830 peptide. These results thus provide clear evidence that Th epitopes expressed in the constant region of H22 can be effectively and specifically presented.

Figure 27:
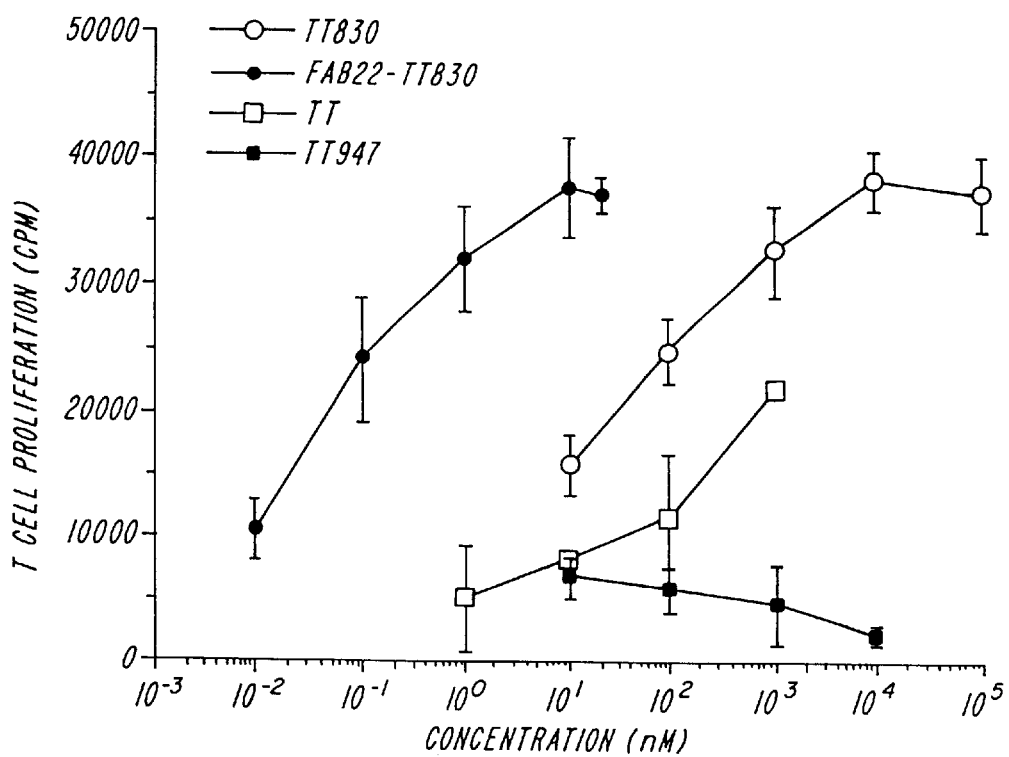
FIG. 27 is a graphic representation of the proliferation of T cells incubated with irradiated monocytes and various concentrations of TT830, Fab22-TT830, TT, or TT947, showing that the fusion protein Fab22-TT830 enhances the presentation of the Th epitope by about 1000 fold as compared to TT830.

Blockade of Fc$\gamma$RI on Monocytes Abrogates the Enhancement of Ag Presentation by the H22Fd-TT Fusion Protein To directly determine whether the enhancement of peptide presentation through the use of the fusion protein is Fc$\gamma$RI-mediated, binding of Fab22-TT830 to Fc$\gamma$RI on Ag-presenting monocytes was blocked by treating monocytes with mAb 22 F(ab')$_2$ for 1 h prior to the addition of Fab22-TT830 or TT830 peptides. Enhancement of peptide presentation by the fusion protein was abrogated by mAb 22 F(ab')$_2$, whereas presentation of TT830 was unaffected (FIG. 27). The fact that the binding of mAb 22 F(ab')$_2$ to Fc$\gamma$RI did not lead to an enhancement of the presentation of free peptides implies that binding of mAb 22 to Fc$\gamma$RI alone did not alter the functional state of monocytes in a way that enhanced Ag presentation. Therefore, linkage of the peptide to anti-Fc$\gamma$RI Ab 22 appears to be necessary for the observed enhancing effects on Ag presentation, suggesting that the enhanced presentation is probably a result of efficient Ag capture through Fc$\gamma$RI.

Figure 28:
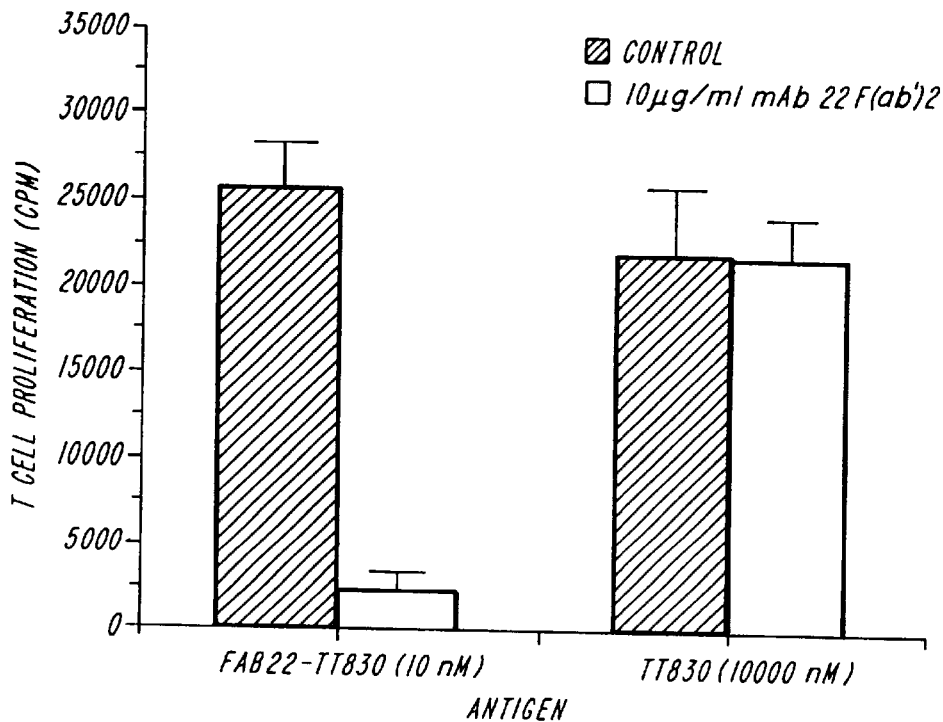
FIG. 28 represents a histogram showing the proliferation of T cells incubated with TT830 at 1000 nM or FAb22-TT830 at 10 nM and monocytes, preincubated or not with saturating amounts of mAb 22 F(ab')2 prior to addition of the T cells and the antigen.
Figure 29:
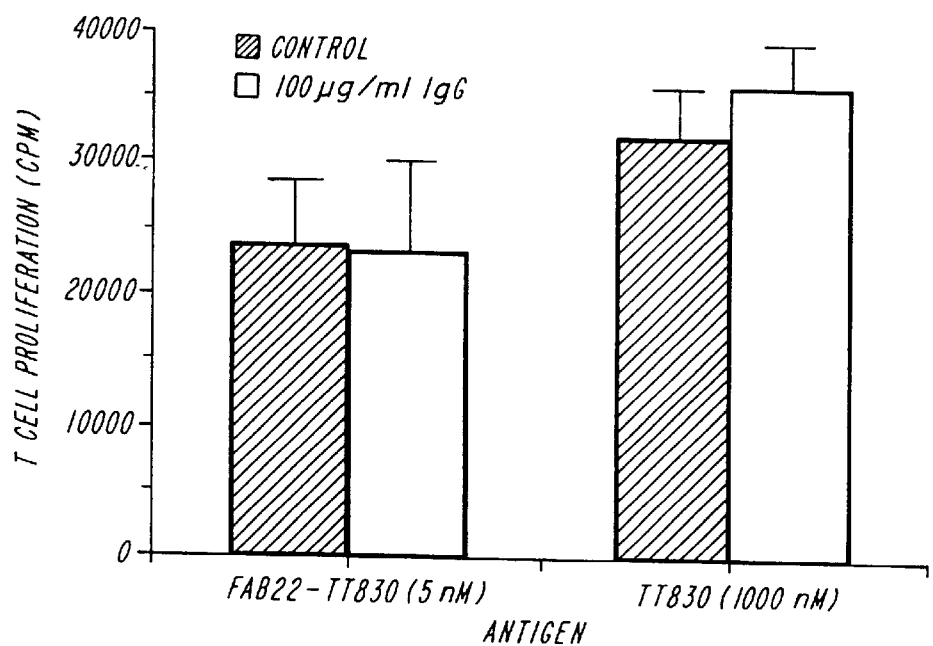
FIG. 29 represents a histogram showing the proliferation of T cells incubated with monocytes and Fab22-TT830 at 5 nM or TT830 at 1000 nM in the absence (control) or presence of IgG.

Enhancement of Peptide Presentation by H22 is not Affected by the Presence of Human IgG Under physiological conditions, the ligand-binding domain of Fc$\gamma$RI is saturated by IgG which blocks efficient targeting of AgAb to this receptor. A unique advantage for using derivatives of mAb 22 to trigger Fc$\gamma$RI function is that Ab 22 binds to an epitope outside the ligand binding domain. Therefore, functions triggered by mAb 22, such as ADCC, phagocytosis and Ag presentation are not inhibited by physiological levels of IgG (Gosselin E. J., supra, Guyre P. M. (1989) *J. Immunol.* 143–1650–55). Similarly, the enhanced presentation of the TT830 peptide using the fusion protein Fab22-TT830 was not inhibited by IgG (FIG. 28), suggesting that H22-based fusion proteins is also an effective way to target peptide Ags to Fc$\gamma$RI in vivo.

IFN-$\gamma$ and IL-4 Production is Increased Following H22Fd-TT Fusion Protein-enhanced Ag Presentation Upon activation, T cells not only undergo clonal expansion through proliferation, but also produce cytokines such as IFN-$\gamma$ and IL-4 to exert their effector function of B cell differentiation and monocyte activation (Paul W. E. and Seder, R. A. (1994) *Cell* 76:241–251). Therefore, the production of IFN-$\gamma$ and IL-4 following H22 fusion protein-enhanced Ag presentation was examined. As shown in FIGS. 28A and 28B, both IFN-$\gamma$ and IL-4 production levels were enhanced by Fab22-TT830, especially at suboptimal Ag concentrations. However, in these experiments, the enhancement for cytokine production (about 20-fold) was less than that for T cell proliferation (about 600-fold).

Thus, Th epitopes expressed in the constant region of anti-Fc$\gamma$RI mAb H22 can be effectively processed and presented by human monocytes, leading to enhanced T cell activation and cytokine production.

Presentation of APL, TT833S and Fab22-TT833S Fails to Stimulate T Cell Proliferation Peptides containing one or two amino acid changes from native T cell epitopes, termed Altered Peptide Ligands (APL) by Allen and coworkers, have been shown to be agonists, partial agonists, or antagonists for T cell activation (Sette et al. (1994) *Ann. Rev. Immunol.* 12:413 and Evavold et al. (1993) *Immunol. Today* 14:602). Recognition of APL by specific T cells through TCR in some cases triggered partial signal transduction and resulted in (i) inhibition of T cell stimulation by superantigen (Evavlold et al. (1994) *Proc. Natl. Acad. Sci. U.S.A.* 91:2300), T cell anergy (Sloan-Lancaster et al. (1993) *Nature* 363:156 and Sloan-Lancaster et al. (1994) *J. Exp. Med.* 185:1195), or (iii) modulation of Th1/Th2 differentiation (Nicholson et al. (1995) *Immunity* 3:397; Pfeiffer et al. (1995) *J. Exp. Med.* 181:1569; and Windhagen et al. (1995) *Immunity* 2:373). Partial agonists have been shown to stimulate some T cell functions such as IL-4 production by T cells, but not others such as T cell proliferation (Evabold et al. (1991) *Science* 252:1308). Partial agonists also can induce anergy. Certain APL do not trigger any detectable signaling events upon interaction with TCR, but can function as TCR antagonists to inhibit T cell proliferation in response to wild-type peptide antigen and are thus called TCR antagonists (De Magistris et al. (1992) *Cell* 68:625 and Ruppert et al. (1993) Proc. Natl. Acad. Sci. USA 90:2671.

Figure 30A:
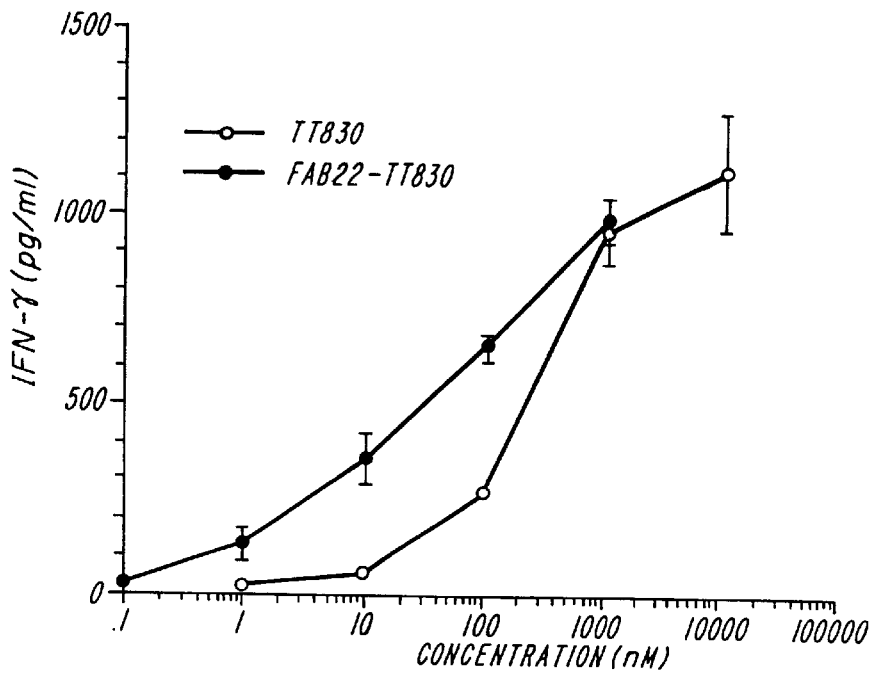
FIG. 30, panels A and B, are graphic representations showing the concentration of IFN-γ (panel A) and IL-4 (panel B) in the supernatant of T cells cultured for 2 days with monocytes and various concentrations of TT830 or Fab22-TT830.
Figure 30B:
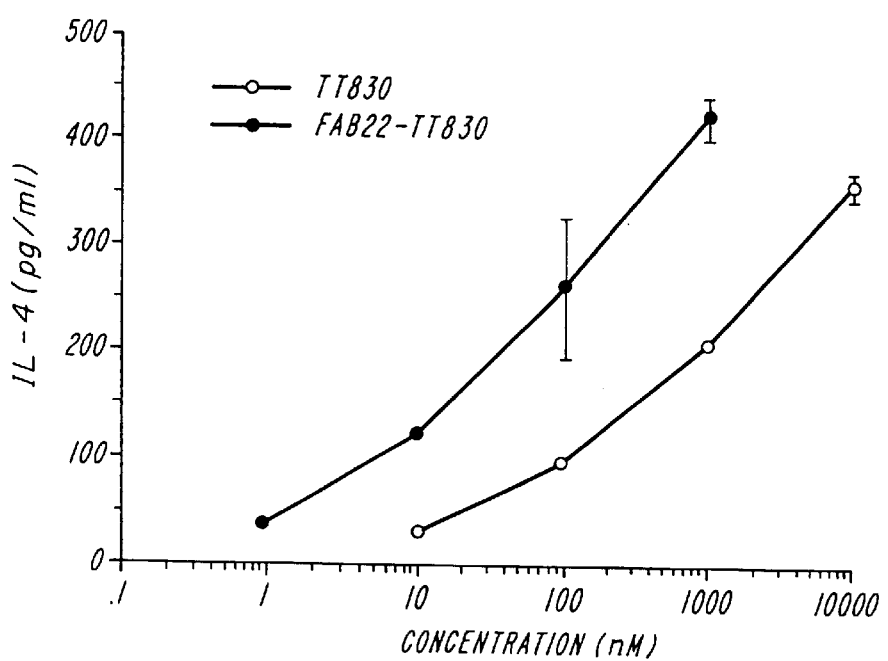
Figure 31:
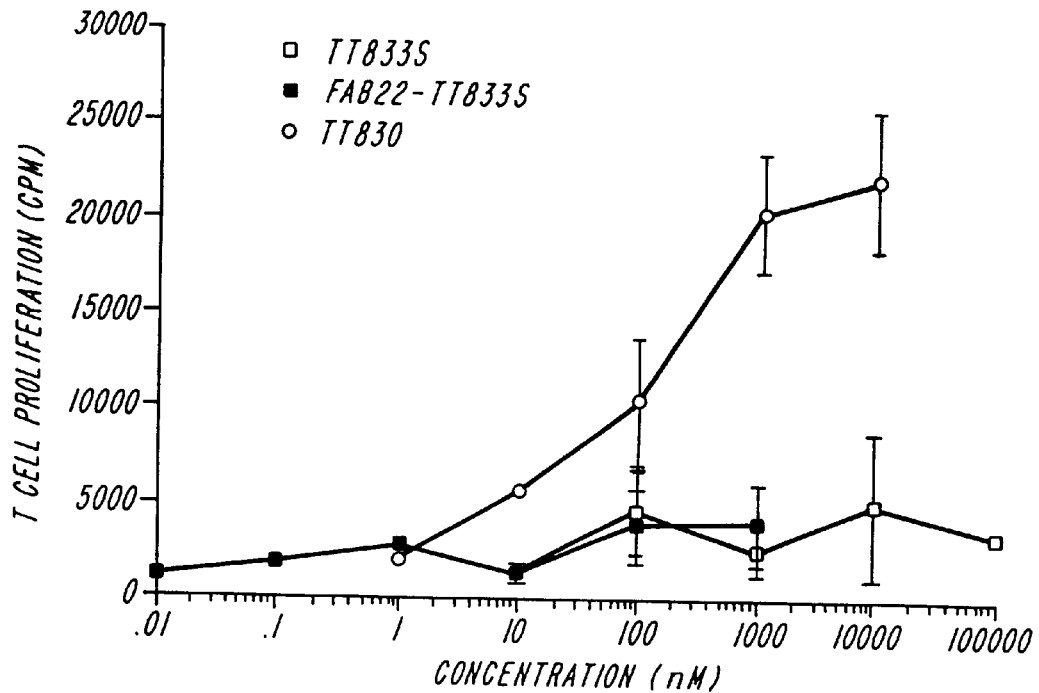
FIG. 31 is a graphic representation depicting the proliferation of T cells incubated with monocytes and various concentrations of TT833S, Fab22-TT833S, or TT830.
Figure 32:
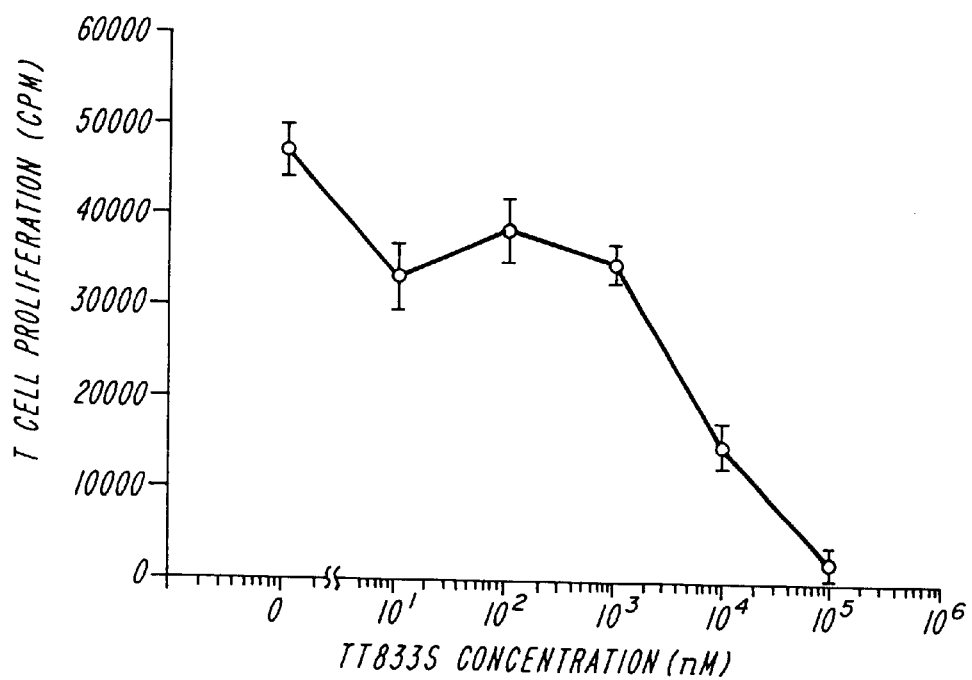
FIG. 32 is a graphic representation of the proliferation of T cells incubated for 2 days with TT830 and monocytes, preincubed overnight with various concentrations of TT833S.
Figure 33:
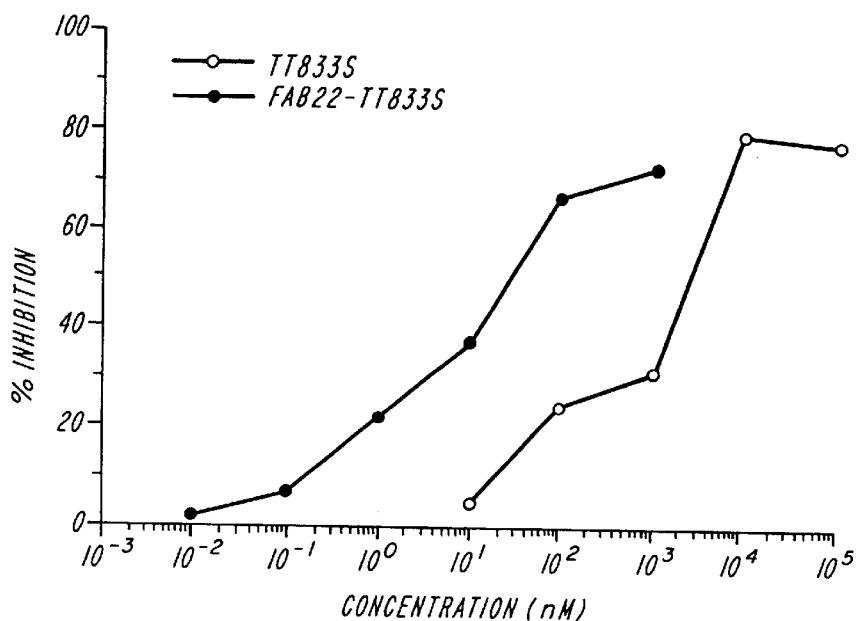
FIG. 33 is a graphic representation of the percent inhibition of proliferation of T cells incubated for 2 days with TT830 and monocytes, preincubed overnight with various concentrations of TT833S or FAb22-TT833S.
Figure 34:
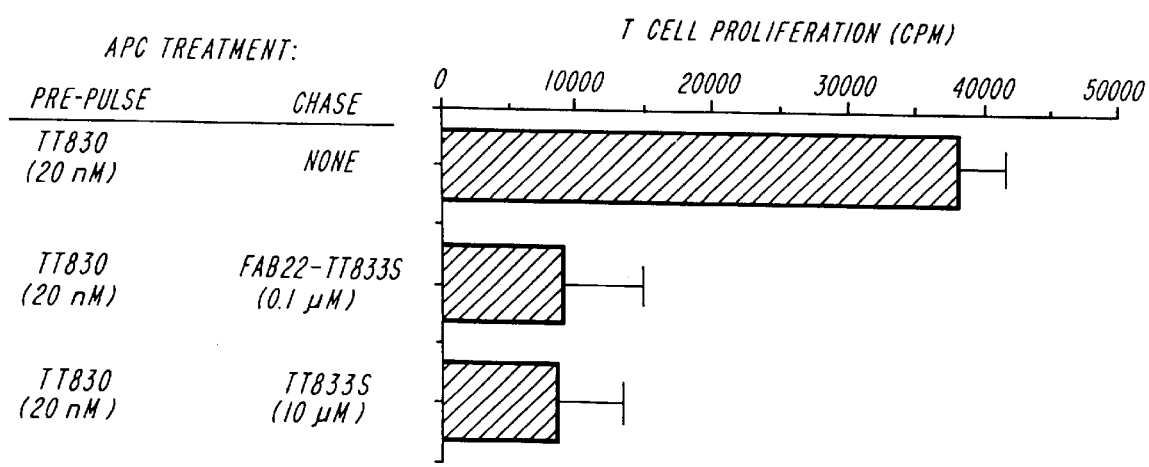
FIG. 34 is a histogram representing the proliferation of T cells incubated for 2 days with monocytes, which were first incubated with TT830 for 4 hours (Pre-pulse) and then incubated overnight with 10 $\mu$M TT833S or 0.1 $\mu$M Fab22-TT833S (Chase) prior to addition of the T cells.
Figure 35:
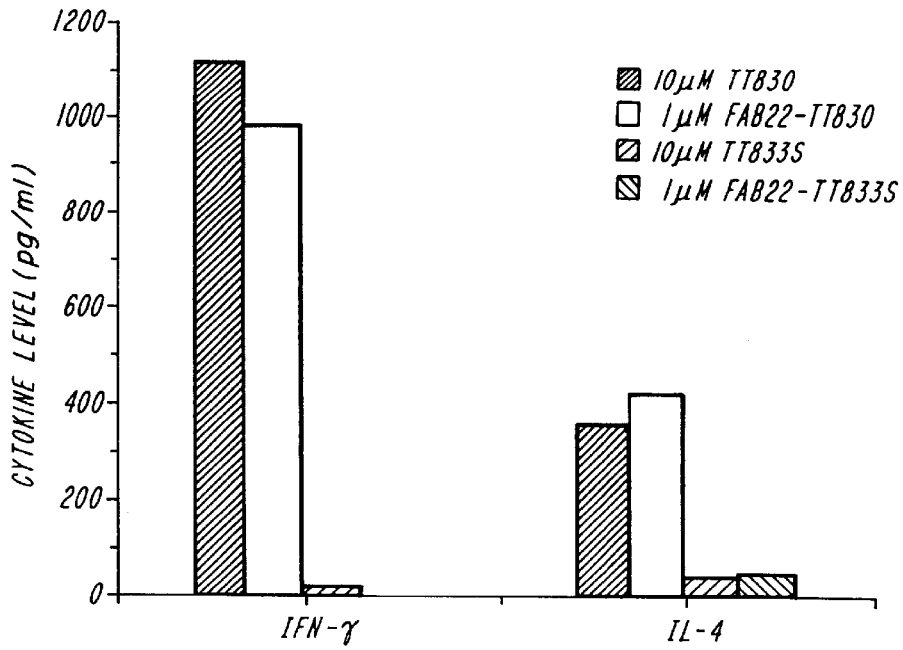
FIG. 35 is a histogram representing the concentration of interferon-$\gamma$ (IFN-$\gamma$) and IL-4 in the supernatant of T cells cultured with monocytes and TT830, FAb22-TT830, TT833S, and Fab22-TT833S.
Figure 36:
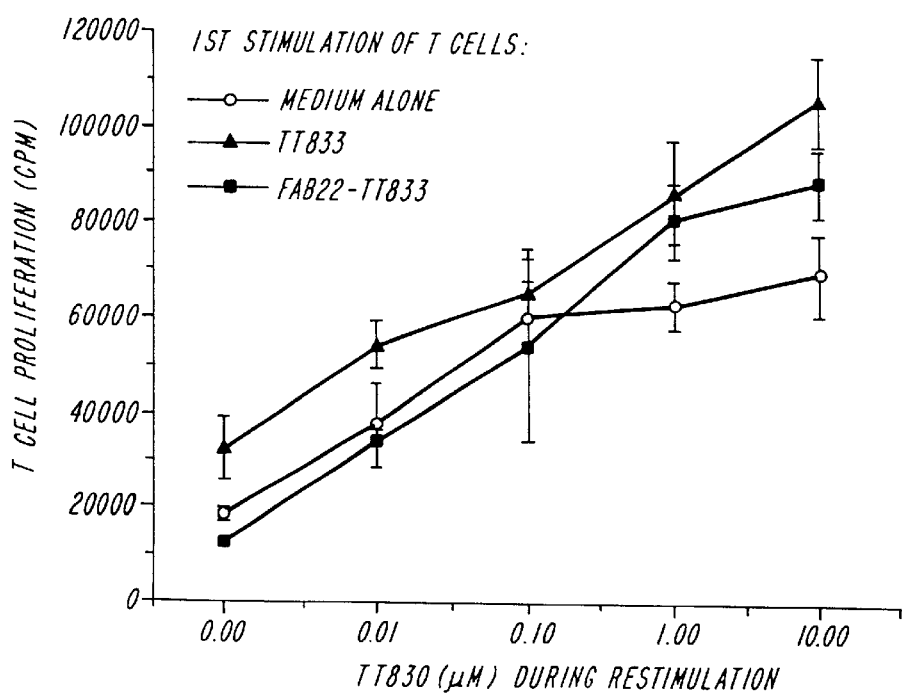
FIG. 36 is a graphic representation of the proliferation of T cells stimulated for one day with monocytes in medium alone, with TT833S, or with Fab22-TT833S and then restimulated with monocytes and various concentrations of TT830 for two days, indicating that TT833S and Fab22-TT833S do not lead to T cell anergy.

This example demonstrates that the peptide TT833S, an antagonist peptide for T cell epitope TT830 of tetanus toxin and Fab22-TT833S fail to stimulate T cell proliferation. As shown in FIG. 30, even at doses as high as 100 μM for TT833S and 1 μM for Fab22-TT833S, no significant proliferation of TT830-specific T cells was observed. This indicates that changing lysine to serine at position 833 of the TT830 peptide eliminated T cell reactivity of this T cell epitope. Additionally, when peptides TT830 and TT833S were simultaneously presented to TT830-specific T cells, T cell proliferation in response to TT830 was inhibited by TT833S in a dose-dependent fashion, showing that TT833S can function as an antagonist for TT830-specific T cells (FIG. 31).

Fab22-TT833S is at least 100 Times More Effective Than TT833S in Inhibiting T Cell Activation This example compares the relative efficiency of TT833S and Fab22-TT833S in inhibiting T cell proliferation in response to TT830. As shown in FIG. 32, Fab22-TT833S was about 100 times more effective than TT833S in inhibiting TT830-stimulated T cell proliferation. This suggests that the APL, TT833S, when expressed in the constant region of mAb H22, can be correctly and effectively presented by APC. The increased antagonistic efficacy of fusion protein Fab22-TT833S on T cell proliferation probably reflects more efficient Ag capture mediated by FcγRI as compared to free peptides.

Inhibition of T Cell Activation is Mediated by Competition for T Cell Receptor Binding Rather Than for MHC Class II Binding.

The antagonist effects of APL TT833S and fusion protein Fab22-TT833S might be through competition at the level of MHC-binding or TCR-binding, or both. To gain insight into the mechanisms involved, "pre-pulsing" experiments, first described by Sette and co-workers (DeMagistris, M. T. et al. (1992) Cell 68:625–634), were performed. This experimental setting allows agonist (TT830) to bind to MHC Class II in the absence of competition from the inhibitor (TT833S) and thus, only TCR antagonists but not pure MHC blockers would be effective in inhibiting agonist-stimulated T cell proliferation. Ag-presenting monocytes were pulsed with suboptimal (20 nM) TT830 for 4 h to allow TT830 to bind with MHC Class II in the absence of competition from TT833S. The APL, TT833S or Fab22-TT833S, was then incubated with the pre-pulsed monocytes for an additional 16 h. Responding T cells were added and their proliferation was measured as described above. Even under such conditions where MHC blockade plays a minimal role, T cell proliferation was still inhibited (FIG. 33). Thus, the inhibition appears to be a result of competition for T cell receptor rather than for MHC Class II binding.

Presentation of TT833S and Fab22-TT833S Fails to Stimulate the Production of IL-4 and IFN-γ by T Cells In some circumstances, APL can stimulate T cell cytokine production but not proliferation (Evavold B. D. and Allen P. M. (1991) *Science* 252:1308–1310). To deterine if presentation of TT833S simulates the production of cytokines, the level of IL-4 and IFN-γ in supernatants obtained from Ag presentation assays was determined. As shown in FIG. 34, both TT833S and Fab22-TT833S were ineffective in stimulating IFN-γ and IL-4 production by T cells.

Presentation of TT833S and Fab22-TT833S Does not Lead to T Cell Anergy

Allen and co-workers reported that interaction of TCR with some APL-MHC Class II complexes led to T cell anergy (Sloan-Lancaster J. et al. (1993) *Nature* 363:156–159, Sloan-Lancaster J. et al. (1994) *J. Exp. Med.* 180:1195–1205). An experimental scheme similar to theirs was used to determine whether presentation of TT833S could also cause T cell anergy. As shown in FIG. 35, when T cells were recovered after incubation with APC and TT833S or Fab22-TT833S for 1 day, 2 days, or 4 days, they responded to subsequent antigenic challenge as well as T cells which had been incubated with APC alone. Therefore, the antagonist, presented via the use of either peptide alone or Fab22-TT833S, did not cause T cell anergy. Furthermore, the same percentage of viable T cells (about 50%) was recovered from cultures with no peptides, TT833S or Fab22-TT833S, suggesting that presentation of TT833S also did not increase T cell death.

The observation that immunogenicity is increased by about 1000 fold by targeting antigenic peptides to FcγRI using an anti-FcγRI mAb 22-based fusion protein indicates that such fusion proteins will be useful for peptide-based vaccines for, e.g., infectious diseases and cancer. Engineering peptides into the constant domains of human mAb that are specific for particular APC surface molecules represent a general approach to increase the antigenic potency for peptide-based vaccines.

Moreover, the observation that the FcγRI-targeted antagonistic peptide inhibited proliferation of TT830-specific T cells even when APCs were first pulsed with native peptide, a situation comparable to that which would be encountered in vivo when attempting to ameliorate an autoimmune response show that targeted presentation of antagonistic peptides can be used as Ag-specific therapies for disorders, e.g., T cell-mediated autoimmune diseases. APL-based treatment will provide an antigen-specific immunotherapy for T cell mediated autoimmune diseases such as rheumatoid arthritis and multiple sclerosis. Furthermore, the use of a fusion protein having one binding specificity to an FcγRI and a peptide which is a partial agonist of an antigen involved in immune disorders characterized by excessive immune responses will be useful in treating such immune disorders by inducing antigen-specific anergy. Thus, the invention provides methods for treating various immunological disorders, by providing a method allowing for increased antigen presentation of antigens, which either stimulate T cells, block T cell proliferation and/or cytokine secretion, or which induce anergy in the T cells.

Example 8

Functional Single Chain anti-FcγRI-anti-CEA Bispecific Molecules

This example demonstrates that a recombinant bispecific single chain molecule comprising a humanized anti-FcγRI antibody fused to an anti-carcinoembryonic (anti-CEA) antibody is capable of binding to FcγRI and to CEA.

Figure 37:
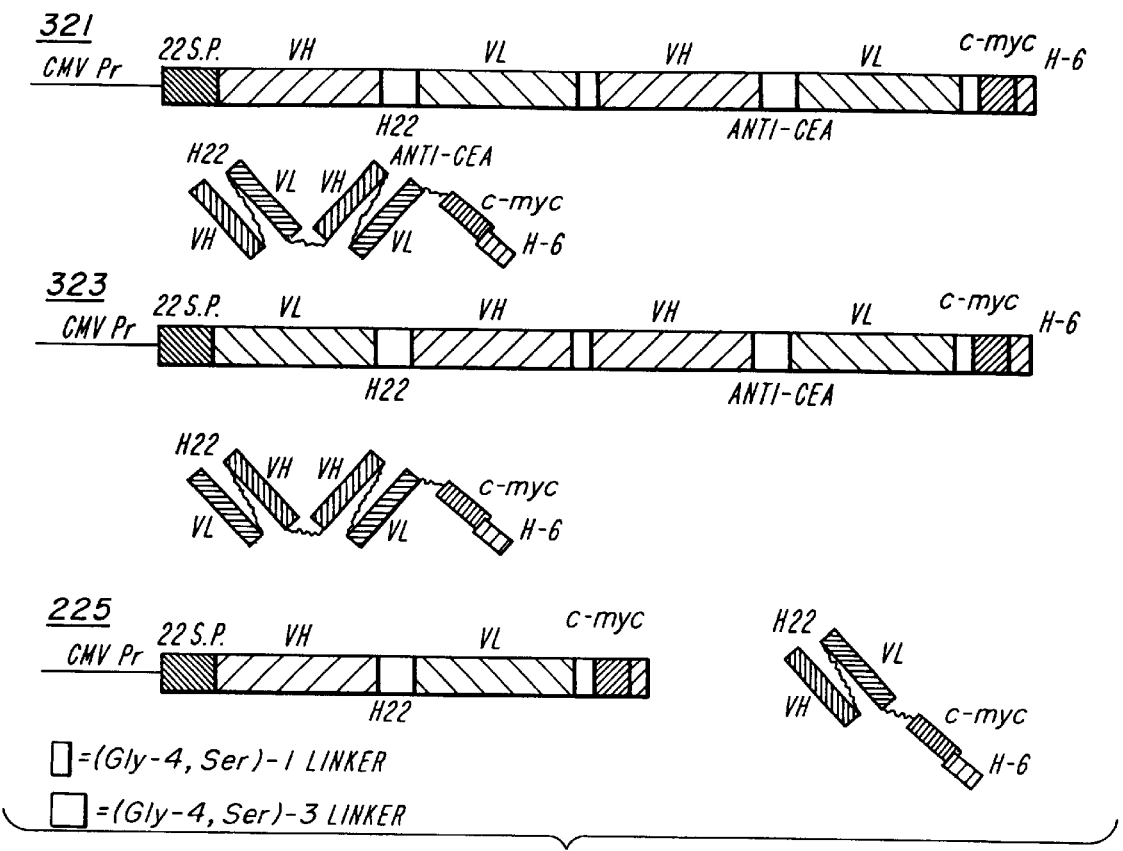
FIG. 37 is a graphic representation of two expression constructs encoding single chain bispecific molecules having one binding specificity for an Fc$\gamma$RI (H22) and one binding specificity for a carcinoembryonic antigen (CEA) (constructs 321 adn 323) and one expression construct encoding a single chain antibody having one binding specificity for an Fc$\gamma$RI. The coding regions are under the control of the CMV promoter (CMV Pr). In addition to the variable regions from the heavy (VH) and light chains (VL) of the antibodies, the proteins encoded by these constructs are fused to a peptide from c-myc (c-myc) and to a hexa-histidine peptide (H-6).

FIG. 37 is a schematic representation of mammalian expression constructs encoding bispecific single chain molecules (constructs 321 and 323) having one binding specificity for the FcγRI and one binding specificity for carcinoembryonic antigen (CEA) that were prepared. The amino acid sequence of the bispecific single chain molecule H22-anti-CEA encoded by construct 321 (SEQ ID NO:16) and the nucleic acid encoding this fusion protein (SEQ ID NO:15) are shown in FIG. 40. The bispecific single chain molecule H22anti-CEA encoded by construct 323 differs from the fusion protein encoded by construct 321 -only in that the VH and VL chains of H22 were switched.

A mammalian expression construct encoding a single chain antibody having one binding specificity for the FcγRI (construct 225) was also prepared. The amino acid sequence of the single chain antibody H22 encoded by construct 225 (SEQ ID NO:14) and the nucleic acid encoding this single chain antibody (SEQ ID NO:13) are shown in FIG. 39.

Each of these constructs were cloned into the Hind III and XbaI sites of pcDNA3 (InVitrogen), from which expression is driven from the CMV promoter. Each of these constructs also contain a nucleic acid sequence encoding a peptide from c-myc and a hexa-histidine peptide, which were used for purification of the recombinant protein from the cell culture. The c-myc tag corresponds to amino acids 410 to 420 of human c-myc (Evan et al. (1985) *Mol. Cell. Biol.* 5:3610). The anti-CEA single chain antibody, termed MFE-23, is further described in Casey et al. (1994) *J. Immunol. Methods* 179:105 and Chester et al. (1994) Lancet 343:455.

The single chain bispecific molecules H22-anti-CEA and the single chain H22 antibody were used in binding assays, performed as follows. ELISA plates are coated with CEA and the blocked with 5% PBA. Supernatants of the cells transfected with the constructs encoding the single chain molecules (transfectomas) were added to the plates, soluble FcγRI/IgM-μ (supernatant from COS transfected cells, described above) was added and binding was detected by incubation of the plates with alkaline-phosphatase (AP) conjugated goat anti-human IgM, development with PNPP, and reading of the plate at 405–650 nm.

Figure 38:
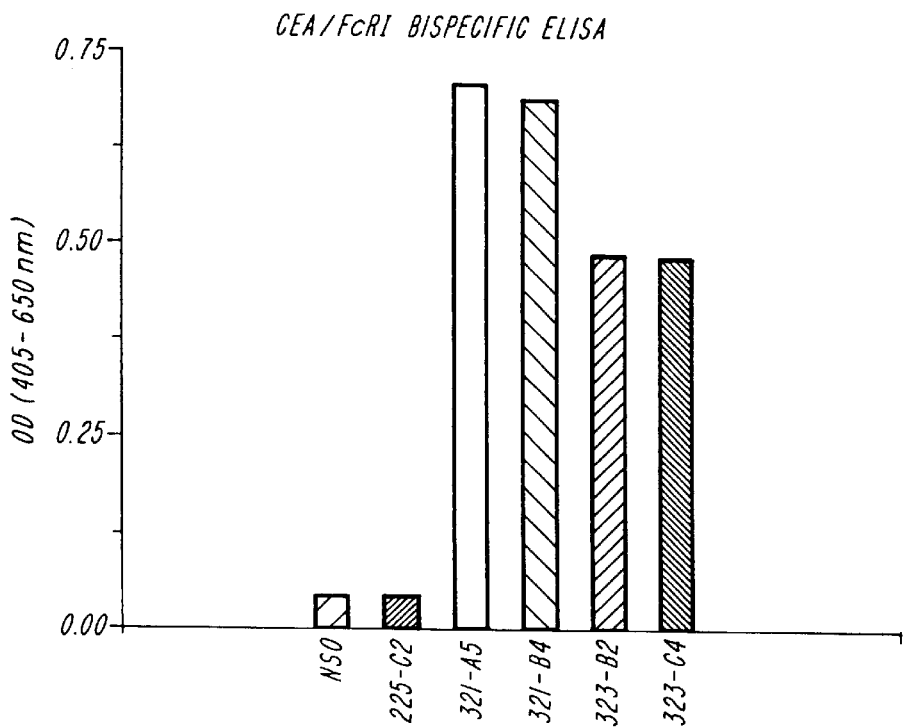
FIG. 38 shows a histogram indicating the level of binding of the single chain bispecific molecules H22-anti-CEA encoded by the expression constructs 321 (321-A5 and 321-B4) and 323 (323-B2 and 323-C4) and the single chain H22 antibody encoded by the construct 225 (225-C2) as measured by bispecific ELISA.

The results are presented in FIG. 38. The results indicate that the single chain bispecific H22-anti-CEA molecules encoded by constructs 321 and 323 bind both FcγRI and CEA. On the other hand, the single chain H22 antibody (encoded by construct 225) does not bind both Fcγrl and CEA, as expected.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of inducing killing of a tumor cell which expresses HER 2/neu or EGFR comprising contacting the tumor cell with a multispecific protein molecule comprising:

a component which binds to an Fc receptor (FcR);

a component which binds to HER 2/neu; and a component which binds to EGFR.

2. The method of claim 1, wherein at least one of said components is produced recombinantly.

3. The method of claim 1, wherein at least one of said components is an antibody or antigen binding fragment thereof.

4. The method of claim 3, wherein said antibody or an antigen binding fragment thereof is humanized.

5. The method of claim 1, wherein said component which binds to an Fc receptor binds the Fc receptor at a site which is not bound by an endogenous immunoglobulin.

6. The method of claim 1, wherein the FcR is an Fcγ receptor.

7. The method of claim 6, wherein the Fcγ receptor is a Fcγ RI receptor.

8. The method of claim 1, wherein said component which binds to HER 2/neu is antibody 520C9 produced by the hybridoma having ATCC Accession Number HB 8696 or an antigen binding fragment thereof.

9. The method of claim 1, wherein said tumor cell is from a cancer selected from the group consisting of breast cancer, sarcoma, carcinoma, and ovarian cancer.

* * * * *